United States Patent
Ellman et al.

(10) Patent No.: US 7,119,105 B2
(45) Date of Patent: Oct. 10, 2006

(54) METHODS FOR TREATING NEURODEGENERATIVE DISORDERS USING ASPARTYL PROTEASE INHIBITORS

(75) Inventors: Jonathan A. Ellman, Oakland, CA (US); Gary Lynch, Irvine, CA (US); Irwin D. Kuntz, Greenbrae, CA (US); Xiaoning Bi, Irvine, CA (US); Christina E. Lee, San Francisco, CA (US); A. Geoffrey Skillman, San Francisco, CA (US); Tasir Haque, Wilmington, DE (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/774,262

(22) Filed: Feb. 5, 2004

(65) Prior Publication Data

US 2004/0157896 A1 Aug. 12, 2004

Related U.S. Application Data

(63) Continuation of application No. 09/534,706, filed on Mar. 24, 2000, now abandoned, which is a continuation-in-part of application No. 09/018,226, filed on Feb. 3, 1998, now Pat. No. 6,150,416.

(60) Provisional application No. 60/125,958, filed on Mar. 24, 1999, provisional application No. 60/036,903, filed on Feb. 4, 1997.

(51) Int. Cl.
*A99Z 99/00* (2006.01)

(52) U.S. Cl. .................. 514/321; 514/323; 514/330; 514/375; 514/414; 514/417; 514/616

(58) Field of Classification Search ................ 514/321, 514/323, 330, 375, 414, 417, 616
See application file for complete search history.

(56) References Cited

U.S. PATENT DOCUMENTS 5,492,812 A 2/1996 Vooheis
5,872,101 A 2/1999 Munoz et al.

FOREIGN PATENT DOCUMENTS

WO WO 98/33795 8/1998

OTHER PUBLICATIONS

Christos Ntais et al, Am J Epidemiol 2004, 159:527-536.*
Kim, W. et al, Expert Opinion on Therapeutic Patents (Ashley Publications), 2002, vol. 12, No. 3, pp. 419-432.*
Jaana Tyynelä et al, The EMBO Journal (2000) 19, 2786-2792.*
Agarwal et al., *J. Med. Chem.*, 29:2519-2524 (1986).
Augelli-Szafran et al., *Ann. Reports Med. Chem.*, 34:21-30 (1999).
Austen et al., *Biomed. Pept. Proteins Nucleic Acids*, 1:243-246 (1995).
Bahr et al., *Experimental Neurology*, 129:81-94 (1994).
Baldwin et al., *Proc. Natl. Acad. Sci. USA*, 90:6796-6800 (1993).
Bednarski et al., *J. Neurochem.*, 67(5):1845-1855 (1996).
Bednarski et al., *J. Neurosci.*, 17(11):4006-4021 (1997).
Bednarski et al., *NeuroReport*, 9:2089-2094 (1998).
Bi et al., *Exp. Neurol.*, 158:312-327 (1999).
Bi et al., *J. Comp. Neuro.*, 401:382-394 (1998).
Braak et al., *Acta Neuropathol.*, 46:79-83 (1979).
Cataldo et al., *Journal of Neuropathology and Experimental Neurology*, 55(6):704-715 (1996).
Cataldo et al., *Proc. Natl. Acad. Sci. USA*, 87:3861-3865 (1990).
Cataldo et al., *Medical Sciences*, 88:10998-11002 (1991).
Cataldo et al., *Brain Research*, 513:181-192 (1990).
Chevallier et al., *Brain Res.*, 750:11-19 (1997).
Crawford et al., *Neurosci. Lett.*, 289(1):61-65 (2000), Medline Abstract 10899409.
Dreyer et al., *Eur. J. Biochem.*, 224:265-271 (1994).
Estus et al., *Ann. N.Y. Acad. Sci.*, 674:138-148 (1992).
Goode et al., *J. Cell Biol.*, 124:769-782 (1994).
Haque et al., *J. Med. Chem.*, 42:1428-1440 (1999).
Hawley et al., "The Condensed Chemical Dictionary," 1977, Van Nostrand, New York, p. 822.
Hoffman et al., *Neuroscience Letters*, 250:75-78 (1998).
II et al., *Virchows Archiv A Pathol Anat*, 423:185-194 (1993).
Isahara et al., *Neuroscience*, 91(1):233-249 (1999).

| NAME | STRUCTURES | MOLECULAR WEIGHT | Ki (nM) |
|---|---|---|---|
| CEL5-A | 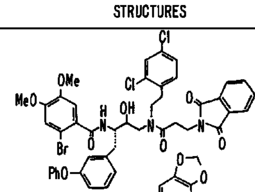 | 839.6 | 0.7 |
| CEL5-G | 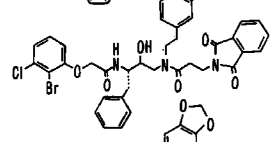 | 697.2 | 15 |
| EA-1 | | 650 | 1.9 |

Jupp et al., *Biochem. J.*, 265:871-878 (1990).
Kenessey et al., *J. Neurochem.*, 69(5):2026-2038 (1997).
Kick et al., *Chemistry & Biology*, 4(4):297-307 (1997).
Kick et al., *J. Med. Chem.*, 38:1427-1430 (1995).
Kosik et al., *Proc. Natl. Acad. Sci. USA*, 83:4044-4088 (1986).
Kowall et al., *Proc. Natl. Acad. Sci. USA*, 88:7247-7251 (1991).
Krafft et al., *Methods Enzymol.*, 241:70-86 (1994).
Kreutzberg, *Arzneim.-Forsch./Drug Res.* 45(I), Nr. 3a, 357-360 (1995).
Lamb et al., *Nature Genet.*, 5:22-29 (1993).
Lee et al., *J. Am. Chem. Soc.*, 120:9735-9747 (1998).
Lee et al., *Science*, 251:675-678 (1991).
Levy-Strumpf et al., *Oncogene*, 17:3331-3340 (1998).
Lindwall et al., *J. Biol. Chem.*, 259(19):12241-12245 (1984).
MacKay et al., *Eur. J. Biochem.*, 244:414-425 (1997).
Mann et al., *Neuropathol. Appl. Neurobiol.*, 13:123-139 (1987).
Mateo et al., *Am. J. Med. Genet.*, 114(1):31-33 (2002), Medline Abstract PMID 11840502.
Matsui et al., *Ann. Neurol.*, 49(4):544-545 (2001), Medline Abstract PMID 11310638.
Matsuo et al., *Neuron*, 13:989-1002 (1994).
Menzer et al., *Am. J. Med. Genet.*, 105(2):179-182 (2001), Medline Abstract PMID 11304834.
Mullan et al., *Nature Genet.*, 1:345-347 (1992).
Murphy et al., *J. Biol. Chem.*, 274(17):11914-11923 (1999).
Nakamura et al., *Neurosci. Lett.*, 97:215-220 (1989).
Nakanishi et al., *Exp. Neurol.*, 126:119-128 (1994).
Nakanishi et al., *J. Neurochem.*, 68:739749 (1997).
Nieto et al., *J. Neurosci.*, 37(1):163-170 (1990).
Ohsawa et al., *Arch. Histol. Cytol.*, 61(5):395-403 (1998).
Olson et al., "Annual Reports Med. Chem.," 35:31-40 (2000).
Pearson et al., *Proc. Natl. Acad. Sci. USA*, 90:10578-10582 (1993).
Purpura et al., *Brain Res.*, 116:1-21 (1976).
Roberg et al., *Am. J. Pathol.*, 152(5):1151-1156 (1988).
Selkoe, *TINS*, 16(10):403-409 (1993).
Wagner et al., *J. Clinical Invest.*, 104:1329-1332 (1999).
Weingarten et al., *Proc. Natl. Acad. Sci. USA*, 72(5):1858-1862 (1975).
Wiley et al., *Med. Res. Rev.*, 13(3):327-384 (1993).
Williams, Jr. et al., *Biochemistry*, 18:2499-2503 (1979).
Wischik et al., *Proc. Natl. Acad. Sci. USA*, 85:4506-4510 (1988).
Yong et al., *Exp. Neurol.*, 157:150-160 (1999).
"Webster's New World Dictionary, College Ed.," no author listed, World Publishing, p. 946 (1962).
"Developments in the Treatment of Parkinson's Disease," *Drug and Ther. Bull.*, 35:36-40 (1997).

\* cited by examiner

*Primary Examiner*—Thomas C. McKenzie

(74) *Attorney, Agent, or Firm*—Townsend & Townsend & Crew LLP

(57) ABSTRACT

The present invention relates to () non-peptide aspartyl protease inhibitors; (ii) methods for modulating the processing of an amyloid precursor protein (APP); (iii) methods for modulating the processing of a tau protein (τ-protein); and (iv) methods for treating neurodegenerative diseases. For instance, in one embodiment, the present invention provides a method for modulating the processing of an amyloid precursor protein (APP), the method comprising contacting a composition containing the APP with an aspartyl protease inhibitor having the formula:

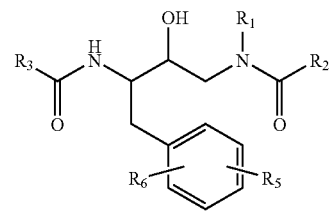

wherein:

$R_1$, $R_2$ and $R_3$ are members independently selected from the group consisting of alkyl, substituted alkyl, aryl, substituted aryl, arylalkyl, substituted arylalkyl, aryloxyalkyl, substituted aryloxyalkyl, heteroaryl, substituted heteroaryl, heteroarylalkyl, substituted heteroarylalkyl, heterocycles, substituted heterocycles, heterocyclicalkyl and substituted heterocyclicalkyl; and $R_5$ and $R_6$ are independently selected from the group consisting of hydrogen, halogen, alkyl, substituted alkyl, aryl, substituted aryl, arylalkyl, substituted arylalkyl, aryloxyalkyl and substituted aryloxyalkyl; or $R_5$ and $R_6$ and the carbons to which they are bound join to form an optionally substituted carbocyclic or heterocyclic fused ring system having a total of 9- or 10-ring atoms within the fused ring system.

35 Claims, 22 Drawing Sheets

INTERMEDIATE OF PEPTIDE HYDROLYSIS

HYDROXYETHYLAMINE-BASED INHIBITORS

R2 SUBSTITUENT

F

H

| NAME | STRUCTURES | MOLECULAR WEIGHT | Ki (nM) |
|---|---|---|---|
| CEL5-A | 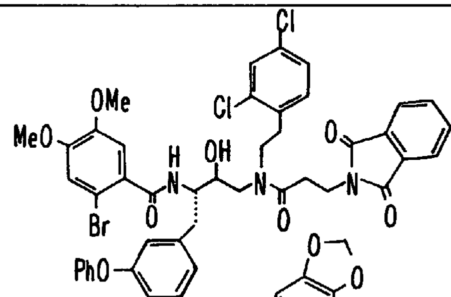 | 839.6 | 0.7 |
| CEL5-G | 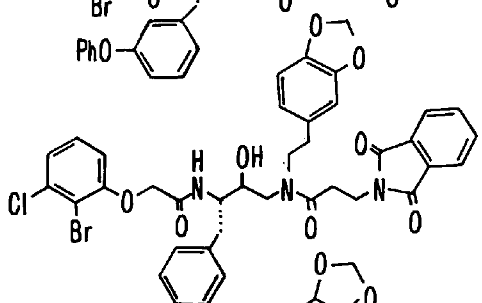 | 697.2 | 15 |
| EA-1 | 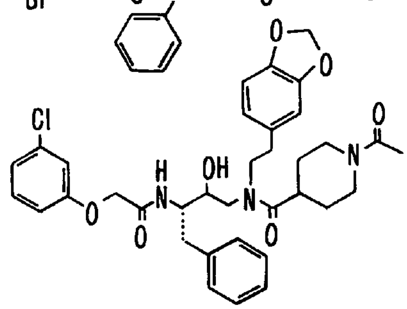 | 650 | 1.9 |

METHODS FOR TREATING NEURODEGENERATIVE DISORDERS USING ASPARTYL PROTEASE INHIBITORS

CROSS-REFERENCES TO RELATED APPLICATIONS

This application is a continuation of U.S. patent application Ser. No. 09/534,706, filed Mar. 24, 2000, now abandoned, which is a continuation-in-part of U.S. patent application Ser. No. 09/018,226, filed Feb. 3, 1998 now U.S. Pat. No. 6,150,416, issued Nov. 21, 2000, and claims the benefit of these applications, U.S. Provisional Application No. 60/125,958, filed Mar. 24, 1999, and U.S. Provisional Application No. 60/036,903, filed Feb. 4, 1997, the disclosures of which are incorporated by reference.

GOVERNMENT RIGHTS

This invention was made with Government support under Grant (Contract) Nos. RO1 GM53696 and RO1 GM50353 awarded by the National Institutes of Health. The Government has certain rights in this invention.

BACKGROUND OF THE INVENTION

Alzheimer's disease (AD) is the most common form of both senile and presenile dementia in the world and is recognized clinically as relentlessly progressive dementia that presents with increasing loss of memory, intellectual function and disturbances in speech (Merritt, 1979, *A Textbook of Neurology*, 6th edition, 484–489 Lea & Febiger, Philadelphia). The disease itself usually has a slow and insidious progress that affects both sexes equally, worldwide. It begins with mildly inappropriate behavior, uncritical statements, irritability, a tendency towards grandiosity, euphoria and deteriorating performance at work; it progresses through deterioration in operational judgement, loss of insight, depression and loss of recent memory; it ends in severe disorientation and confusion, apraxia of gait, generalized rigidity and incontinence (Gilroy and Meyer, 1979, *Medical Neurology*, 175–179 MacMillan Publishing Co.). Alzheimer's disease afflicts an estimated 4 million human beings in the United States alone at a cost of 35 billion dollars a year (Hay and Ernst, *Am. J. Public Health*, 77:1169–1175 (1987)). It is found in 10% of the population over the age of 65 and 47% of the population over the age of 85 (Evans, et al., *JAMA*, 262:2551–2556 (1989)). In addition, the disease is found at much lower levels in the younger age groups, usually beginning at about 30 years of age and even rarely in late childhood (Adams and Victor, *Principles of Neurology*, 401–407 (1977)).

Proteases and, in particular, aspartyl proteases have been implicated in diseases, such as Alzheimer's Disease, that are characterized by the accumulation of amyloid plaques. Amyloidogenic Aβ peptides (Aβ) are the principle component of the amyloid plaques that accumulate intracellularly and extracellularly in the neuritic plaques in the brain in AD. Aβ is a 4.5 kD protein, about 40–42 amino acids long, that is derived from the C-terminus of amyloid precursor protein (APP). APP is a membrane-spanning glycoprotein that, in the normal processing pathway, is cleaved inside the Aβ protein to produce α-sAPP, a secreted form of APP. Formation of alpha α-sAPP precludes formation of Aβ. It has been proposed that Aβ accumulates by virtue of abnormal processing of APP, so that compounds that inhibit the activity of the enzymes responsible for Aβ production are desirable (see, e.g., Wagner, et al., *Biotech. Report*, 106–107 (1994/1995); and Selkoe, *TINS*, 16:403–409 (1993)).

In addition to the accumulation of amyloid plaques, neurons in AD brains exhibit specific alterations in τ, a family of phosphoproteins that bind tubulin (Weingarten, et al., *Proc. Natl. Acad. Sci. USA*, 72:1858–1862 (1975); and Williams and Detrich, *Biochemistry*, 18:2499–2503 (1979)), and stabilize microtubules (Goode and Feinstein, *J. Cell Biol.*, 124:769–782 (1994)). In these brains, τ proteins adopt an altered form and comprise the dominant component of abnormal cytosketal fibers known as paired helical filaments (PHFs) (see, Kosik, et al., *Proc. Natl. Acad. Sci. USA*, 83:4044–4088 (1986); Lee, et al., *Science*, 251:675–678 (1991); and Mann, et al., *Neuropathol. Appl. Neurobiol.*, 13:123–139 (1987)). Molecular dissection of PHFs has revealed two specific alterations in τ. First, PHF-τ proteins maintain an excessively phosphorylated state throughout postmortem intervals (Matsuo, et al., *Neuron*, 13:989–1002 (1994)). Second, after treatment of PHFs with reducing agents and detergents, the remaining filaments contain truncated forms of τ (Nieto, et al., *Biochem. Biophys. Res. Commun.*, 154:660–667 (1988); Nieto, et al., *J. Neurosci.*, 37:163–170 (1990); and Wischik, et al., *Proc. Natl. Acad. Sci. USA*, 85:4506–4510 (1988)). These results suggest that modifications in the posttranslational processing of τ contribute to the formation of PHFs. It has been proposed that τ-fragments accumulate by virture of abnormal processing of τ by proteases (see, Bednarski and Lynch, *J. Neurochem.*, 67(5):1845–1855 (1996)). As such, compounds that inhibit the acitivity of the enzymes responsible for τ-fragment production are desirable.

Because proteases are implicated in Alzheimer's Disease and in numerous other disorders, there remains a need in the art for the development of potent and specific inhibitors of these enzymes. Quite surprisingly, the present invention fulfills this and other need.

SUMMARY OF THE INVENTION

The present invention relates to (i) non-peptide aspartyl protease inhibitors; (ii) methods for modulating the processing of an amyloid precursor protein (APP); (iii) methods for modulating the processing of a tau protein (τ-protein); and (iv) methods for treating neurodegenerative diseases.

In one aspect, the present invention provides a method for modulating the processing of an amyloid precursor protein (APP), the method comprising contacting a composition containing the APP with an aspartyl protease inhibitor having the general formula:

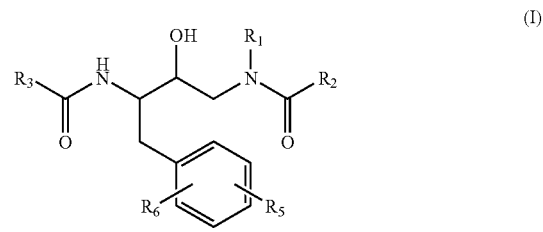

(I)

In Formula I, $R_1$, $R_2$ and $R_3$ are members independently selected from the group consisting of alkyl, substituted alkyl, aryl, substituted aryl, arylalkyl, substituted arylalkyl, aryloxyalkyl, substituted aryloxyalkyl, heteroaryl, substituted heteroaryl, heteroarylalkyl, substituted heteroarylalkyl, heterocycles, substituted heterocycles, heterocyclicalkyl and substituted heterocyclicalkyl.

In Formula I, $R_5$ and $R_6$ are independently selected from the group consisting of hydrogen, halogen, alkyl, substituted alkyl, aryl, substituted aryl, arylalkyl, substituted arylalkyl, aryloxyalkyl and substituted aryloxyalkyl. In an alternative embodiment, $R^5$ and $R^6$ and the carbons to which they are bound, join to form an optionally substituted 9- or 10-ring atom carbocyclic or heterocyclic fused ring system. Typical 9- or 10-atom fused ring systems include, but are not limited to, napthalyl, 1,3-benzodioxolyl, 2,3-benzofuranyl, 1,4-benzodioxanyl, benzimidazoyl, benzothiazolyl etc.

Within the scope of the above Formula I, certain embodiments are preferred. In Formula I, one preferred embodiment is that in which $R_1$ is a functional group including, but not limited to, substituted arylalkyl, substituted aryl, substituted alkyl and substituted heterocyclic groups. Examples of such functional groups include, but are not limited to, the following:

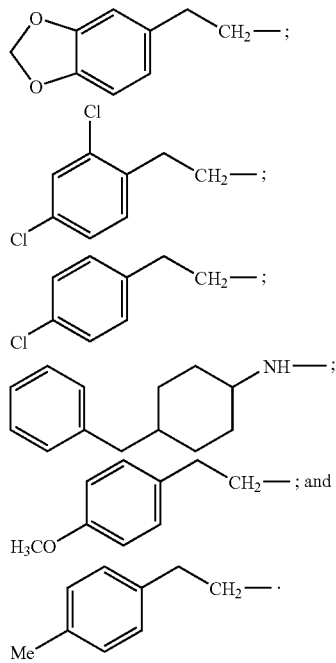

Another preferred embodiment is that in which $R_2$ is a functional group including, but not limited to, substituted alkyl, heterocyclic and substituted heterocyclic groups. Examples of such functional groups include, but are not limited to, the following:

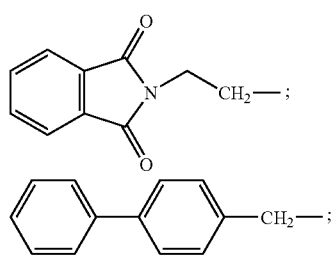

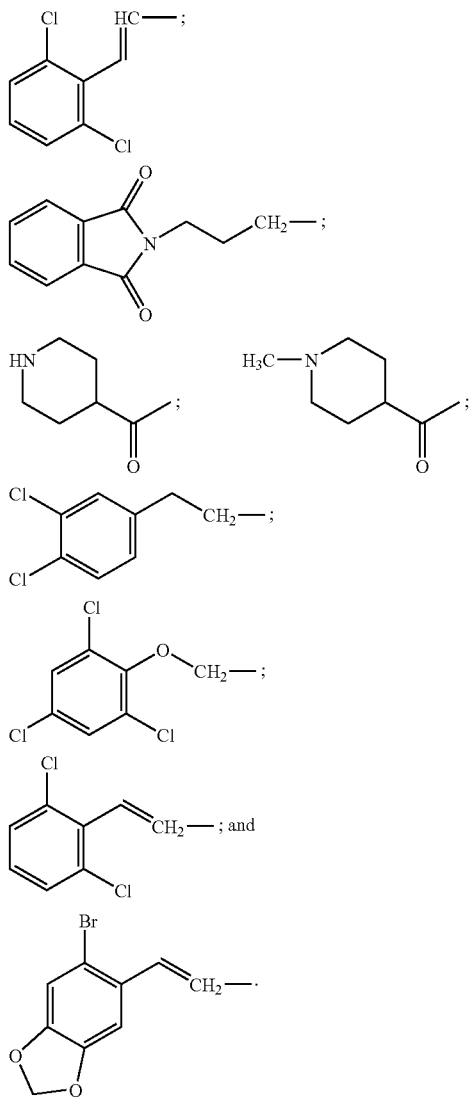

In one embodiment, $R_2$ is a functional group other than a nitrogen-bonded cyclic α-amino acid or ester thereof.

Also preferred is the embodiment in which $R_3$ is a functional group including, but not limited to, substituted alkyl and substituted aryl groups. Examples of such functional groups include, but are not limited to, the following:

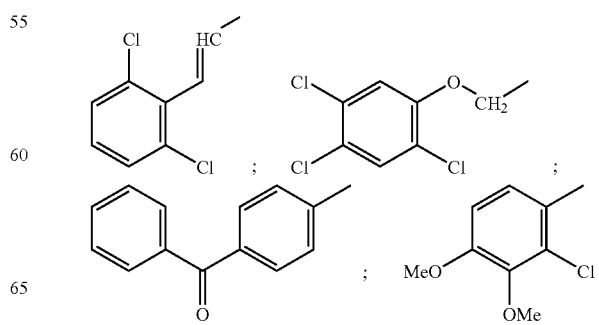

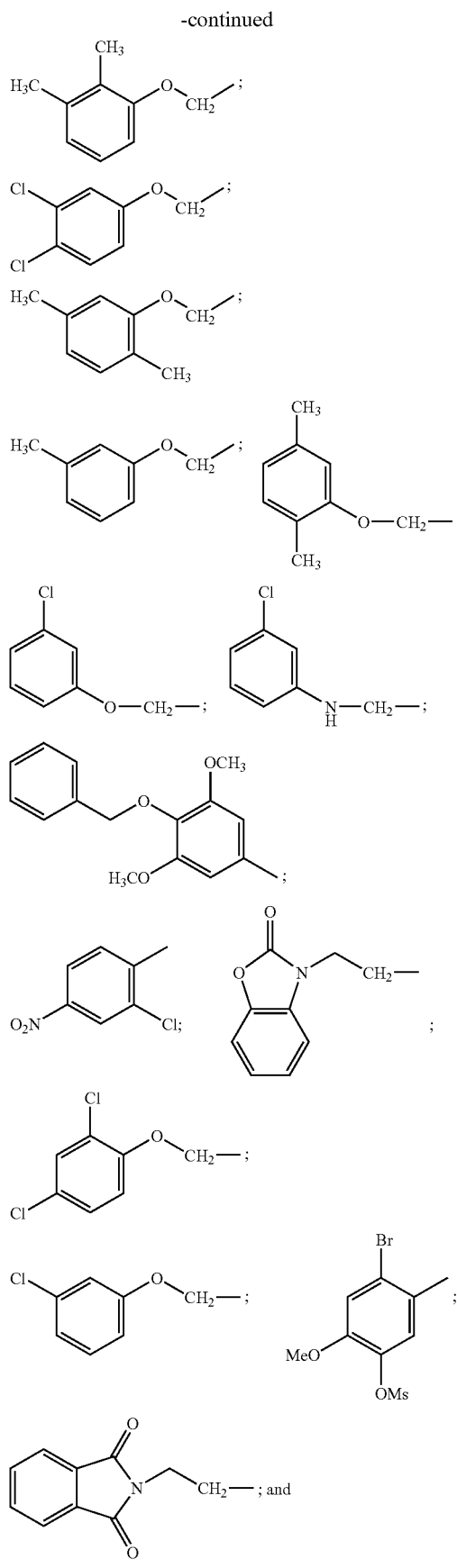

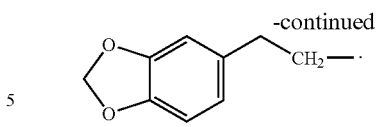

In another preferred embodiment, $R^5$ and $R^6$ and the carbons to which they are bound join to form an optionally substituted napthalene ring. In other preferred embodiments, $R_5$ and $R_6$ are both hydrogen or $R_5$ is hydrogen and $R_6$ is a meta or para substituent.

In a particularly preferred embodiment, the aspartyl protease inhibitor is selected from the group consisting of:

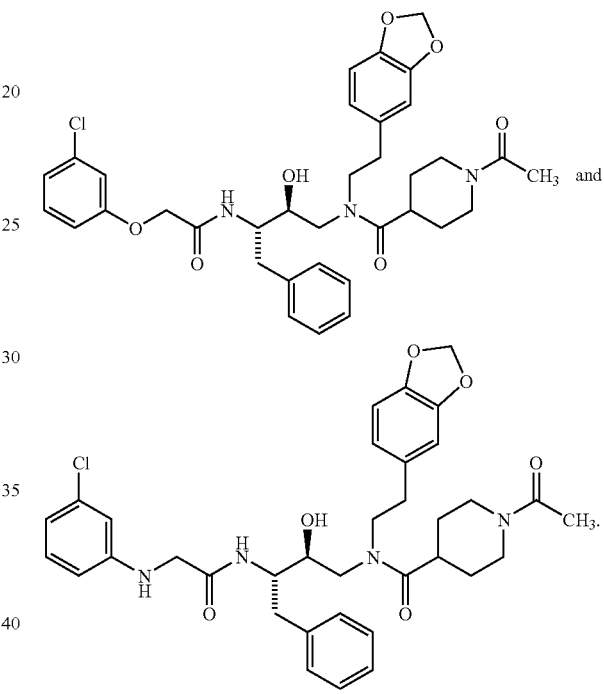

The modulation of APP can be demonstrated in a variety of ways. For example, aspartyl protease inhibitors can be evaluated for the ability to modulate generation of Aβ or α-sAPP. In one preferred embodiment, the formation of Aβ is decreased compared to the amount formed in the absence of the aspartyl protease inhibitor. In another preferred embodiment, formation of α-sAPP is increased compared to the amount formed in the absence of the asparty protease inhibitor. In one embodiment, the composition is a body fluid. In a preferred embodiment, the body fluid is cerebral spinal fluid (CSF).

In another aspect, the present invention provides a method for modulating the processing of a tau-protein (τ-protein), the method comprising contacting a composition containing the τ-protein with an aspartyl protease inhibitor of Formula I. The modulation of τ-protein can be demonstrated in a variety of ways. For example, aspartyl protease inhibitors can be evaluated for the ability to modulate generation of τ-fragments. In one preferred embodiment, the formation of τ-fragments is decreased compared to the amount formed in the absence of the aspartyl protease inhibitor. In one embodiment, the composition is a body fluid. In a preferred embodiment, the body fluid is cerebral spinal fluid (CSF).

In yet another aspect, the present invention provides a method of treating a neurodegenerative disorder, the method comprising: administering to a mammal a therapeutically effective amount of an aspartyl protease inhibitor of Formula I and a pharmaceutically acceptable carrier or excipient. In one embodiment, the neurodegenerative disorder is characterized by the accumulation of amyloid plaques. In another embodiment, the neurodegenerative disorder is characterized by the accumulation of τ-fragments. As such, the aspartyl protease inhibitors of the present invention can be used to treat all amyloid-pathology related diseases and all tau pathology-related diseases. Examples of such neurodegenerative diseases include, but are not limited to, the following: Alzheimer's disease, Parkinson's disease, cognition deficits, Downs Syndrome, cerebral hemorrhage with amyloidosis, dementia (e.g., dementia pugilistica) and head trauma.

Other features, objects and advantages of the invention and its preferred embodiments will become apparent from the detailed description which follows.

BRIEF DESCRIPTION OF THE DRAWINGS

In FIG. 5A, the t-butyl ester of $R_1$=i was used in the coupling reaction. In FIG. 5C, the Boc protected amine of $R_3$=d was used in the coupling reaction. These protecting groups are removed during TFA:$H_2O$ cleavage.

DETAILED DESCRIPTION OF THE INVNETION AND PREFERRED EMBODIMENTS

Figure 1:
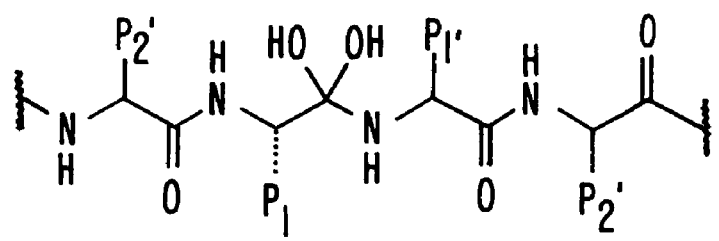
FIG. 1 illustrate isostere-based inhibitor design.
Figure 1:
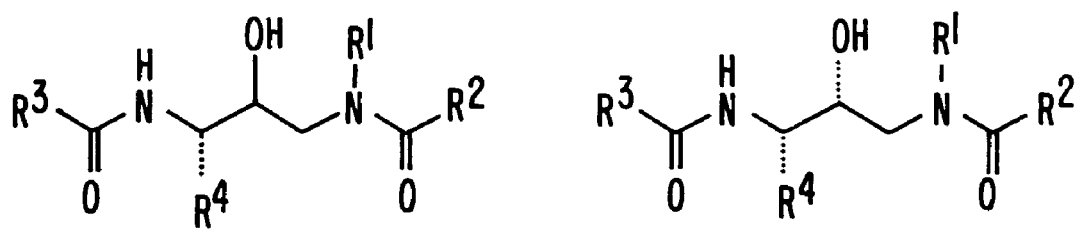

The present invention relates to (i) non-peptide aspartyl protease inhibitors; (ii) methods for modulating the processing of an amyloid precursor protein (APP); (iii) methods for modulating the processing of a tau protein (τ-protein); and (iv) methods for treating neurodegenerative diseases.

A. Definitions

The term "independently selected" is used herein to indicate that the three R groups, i.e., $R_1$, $R_2$ and $R_3$, can be identical or different (e.g., $R_1$, $R_2$ and $R_3$ may all be substituted alkyls or $R_1$ and $R_2$ may be a substituted alkyl and $R_3$ may be an aryl, etc.).

The term "alkyl" is used herein to refer to a branched or unbranched, saturated or unsaturated, monovalent hydrocarbon radical having from 1–12 carbons and preferably, from 1–6 carbons. When the alkyl group has from 1–6 carbon atoms, it is referred to as a "lower alkyl." Suitable alkyl radicals include, for example, methyl, ethyl, n-propyl, i-propyl, 2-propenyl (or allyl), n-butyl, t-butyl, i-butyl (or 2-methylpropyl), etc. As used herein, the term encompasses "substituted alkyls."

"Substituted alkyl" refers to alkyl as just described including one or more functional groups: lower alkyl, aryl, substituted aryl, acyl, halogen (i.e., alkylhalos, e.g., CF3), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon of the alkyl moiety. Additionally, these groups may be pendent from, or integral to, the alkyl chain.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, naphthyl, biphenyl, diphenylmethyl and benzophenone among others. The term "aryl" encompasses "arylalkyl."

The term "arylalkyl" is used herein to refer to a subset of "aryl" in which the aryl group is attached to the nucleus shown in Formula 1 by an alkyl group as defined herein.

"Substituted aryl" refers to aryl as just described including one or more of the following functional groups: lower alkyl, acyl, halogen, alkylhalos (e.g., CF3), hydroxy, amino, alkoxy, alkylamino, acylamino, acyloxy, phenoxy, mercapto and both saturated and unsaturated cyclic hydrocarbons, optionally substituted with one or more heteroatoms, which are fused to the aromatic ring(s), linked covalently or linked to a common group such as a methylene or ethylene moiety. The linking group may also be a carbonyl such as in cyclohexyl phenyl ketone. The term "substituted aryl" encompasses "substituted arylalkyl."

"Substituted arylalkyl" defines a subset of "substituted aryl" wherein the substituted aryl group is attached to the nucleus shown in Formula 1 by an alkyl group as defined herein.

The term "acyl" is used to describe a ketone substituent, —C(O)R, where R is alkyl or substituted alkyl, aryl or substituted aryl as defined herein.

The term "halogen" is used herein to refer to fluorine, bromine, chlorine and iodine atoms.

The term "hydroxy" is used herein to refer to the group —OH.

The term "amino" is used to describe primary amines, R—NH$_2$.

The term "alkoxy" is used herein to refer to the —OR group, where R is a lower alkyl, substituted lower alkyl, aryl, substituted aryl, arylalkyl or substituted arylalkyl wherein the alkyl, aryl, substituted aryl, arylalkyl and substituted arylalkyl groups are as described herein. Suitable alkoxy radicals include, for example, methoxy, ethoxy, phenoxy, substituted phenoxy, benzyloxy, phenethyloxy, t-butoxy, etc.

The term "alkylamino" denotes secondary and tertiary amines wherein the alkyl groups may be either the same or different and are as described herein for "alkyl groups."

As used herein, the term "acylamino" describes substituents of the general formula RC(O)NR', wherein R' is a lower alkyl group and R represents the nucleus shown in Formula 1 or an alkyl group, as defined herein, attached to the nucleus.

The term "acyloxy" is used herein to describe an organic radical derived from an organic acid by the removal of the acidic hydrogen. Simple acyloxy groups include, for example, acetoxy, and higher homologues derived from carboxylic acids such as ethanoic, propanoic, butanoic, etc. The acyloxy moiety may be oriented as either a forward or reverse ester (i.e., RC(O)OR' or R'OC(O)R, respectively, wherein R comprises the portion of the ester attached either directly or through an intermediate hydrocarbon chain to the nucleus shown in claim 1).

As used herein, the term "aryloxy" denotes aromatic groups which are linked to the nucleus shown in FIG. 1 directly through an oxygen atom. This term encompasses "substituted aryloxy" moieties in which the aromatic group is substituted as described above for "substituted aryl."

As used herein "aryloxyalkyl" defines aromatic groups attached, through an oxygen atom to an alkyl group, as defined herein. The alkyl group is attached to the nucleus shown in FIG. 1. The term "aryloxyalkyl" encompasses "substituted aryloxyalkyl" moieties in which the aromatic group is substituted as described for "substituted aryl."

As used herein, the term "mercapto" defines moieties of the general structure R—S—R' wherein R and R' are the same or different and are alkyl, aryl or heterocyclic as described herein.

The term "saturated cyclic hydrocarbon" denotes groups such as the cyclopropyl, cyclobutyl, cyclopentyl, etc., and substituted analogues of these structures. These cyclic hydrocarbons can be single- or multi-ring structures.

The term "unsaturated cyclic hydrocarbon" is used to describe a monovalent non-aromatic group with at least one double bond, such as cyclopentene, cyclohexene, etc. and substituted analogues thereof. These cyclic hydrocarbons can be single- or multi-ring structures.

The term "heteroaryl" as used herein refers to aromatic rings in which one or more carbon atoms of the aromatic ring(s) are substituted by a heteroatom such as nitrogen, oxygen or sulfur. Heteroaryl refers to structures which may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Heteroarylalkyl" defines a subset of "heteroaryl" wherein an alkyl group, as defined herein, links the heteroaryl group to the nucleus shown in FIG. 1.

"Substituted heteroaryl" refers to heteroaryl as just described wherein the heteroaryl nucleus is substituted with one or more of the following functional groups: lower alkyl, acyl, halogen, alkylhalos (e.g., CF3), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are defined by the term "substituted heteroaryl."

"Substituted heteroarylalkyl" refers to a subset of "substituted heteroaryl" as described above in which an alkyl group, as defined herein, links the heteroaryl group to the nucleus shown in FIG. 1.

The term "heterocyclic" is used herein to describe a monovalent saturated or unsaturated non-aromatic group having a single ring or multiple condensed rings from 1–12 carbon atoms and from 1–4 heteroatoms selected from nitrogen, sulfur or oxygen within the ring. Such heterocycles are, for example, tetrahydrofuran, morpholine, piperidine, pyrrolidine, etc.

The term "substituted heterocyclic" as used herein describes a subset of "heterocyclic" wherein the heterocycle nucleus is substituted with one or more functional groups such as lower alkyl, acyl, halogen, alkylhalos (e.g., $CF_3$), hydroxy, amino, alkoxy, alkylamino, acylamino, acyloxy, mercapto, etc.

The term "heterocyclicalkyl" defines a subset of "heterocyclic" wherein an alkyl group, as defined herein, links the heterocyclic group to the nucleus shown in FIG. 1.

The term "optionally substituted napthylene ring" describes a naphthalene ring which may be unsubstituted or may be substituted with one or more functional groups including lower alkyl, halogen, acyl, hydroxy, amino, alkoxy, alkylamino, acylamino, acyloxy or aryl.

The term "substituted heterocyclicalkyl" defines a subset of "heterocyclic alkyl" wherein the heterocyclic nucleus is substituted with one or more functional groups such as lower alkyl, acyl, halogen, alkylhalos (e.g., $CF_3$), hydroxy, amino, alkoxy, alkylamino, acylamino, acyloxy, mercapto, etc.

The term "amyloid precursor protein" or "APP" is used herein to refer to the progenitor of deposited amyloidogenic Aβ peptides (Aβ) found in senile plaques in patients with diseases, such as Alzheimer's disease (AD), that are characterized by such deposition. α-sAPP is an alternative cleavage product of APP; its formation precludes formation of Aβ.

The term "contacting" is used herein interchangeably with the following: combined with, added to, mixed with, passed over, incubated with, flowed over, etc. Moreover, the aspartyl protease inhibitors of present invention can be "administered" by any conventional method such as, for example, parenteral, oral, topical and inhalation routes as described herein.

"An amount sufficient" or "an effective amount" is that amount of a given aspartyl protease inhibitor which exhibits the binding/inhibitory activity of interest or, which provides either a subjective relief of a symptom(s) or an objectively identifiable improvement as noted by the clinician or other qualified observer.

B. Non-Peptide Aspartyl Protease Inhibitors

Figure 2:
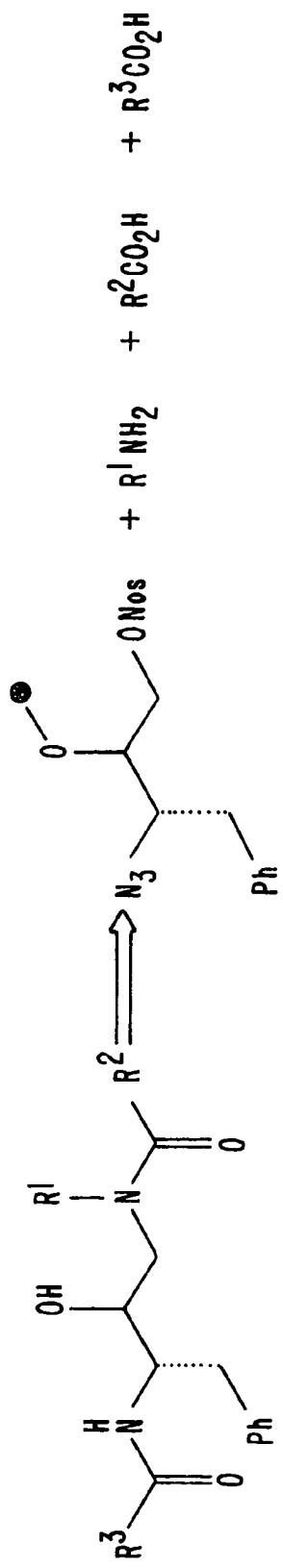
FIG. 2 illustrates components employed to prepare the libraries targeting cathepsin D. The same disconnections provide scaffold 2. Isocyanates and sulfonyl chlorides, which can be used to incorporate $R_2$ and $R_3$, provide ureas and sulfonamides, respectively.

The present invention relates to the identification of a number of small-molecule compounds which are capable of binding to and inhibiting aspartyl proteases and, in particular, cathepsin D employing a combined combinatorial library (see, e.g., Thompson, et al.; *Chemical Reviews*, 96, 555–600 (1996)) and structure based design approach (see, e.g., Kuntz, I. D., *Science*, 257, 1078–1082 (1992)). The libraries of potential aspartyl protease inhibitors (e.g., cathepsin D inhibitors) were based upon the display of functionality about the hydroxyethylamine scaffold illustrated in FIG. 1. For the initial libraries, the $P_1$ sidechain ($R^4$) was held constant as a benzyl substituent based upon X-ray crystallographic data of cathepsin D complexed with the peptide-based natural product pepstatin as reported by Erickson (Baldwin, et al., *Proc. Natl. Acad. Sci. USA*, 90, 6796–6800 (1993)). As illustrated in FIG. 2, diversity was introduced at three positions: a primary amine introduced the $R_1$ substituent, and acylating agents serve to introduce the $R_2$ and $R_3$ substituents. Once prepared, the libraries were screened to identify compounds capable of binding to and inhibiting aspartyl proteases and, in particular, cathepsin D. Thereafter, a second generation library was prepared in an effort to further explore variants of the most active compounds. Thus, by combining a structure-based design and a combinatorial library approach, non-peptidic compounds capable of inhibiting aspartyl proteases and, in particular, cathepsin D have now been identified.

Accordingly, in one embodiment, the present invention provides compounds having the general formula:

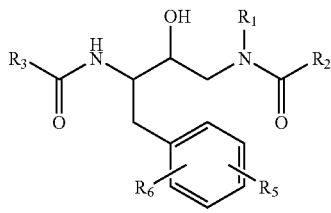

In Formula I, $R_1$, $R_2$ and $R_3$ are members independently selected from the group consisting of alkyl, substituted alkyl, aryl, substituted aryl, arylalkyl, substituted arylalkyl, aryloxyalkyl, substituted aryloxyalkyl, heteroaryl, substituted heteroaryl, heteroarylalkyl, substituted heteroarylalkyl, heterocycles, substituted heterocycles, heterocyclicalkyl and substituted heterocyclicalkyl.

In Formula I, $R_5$ and $R_6$ are independently selected from the group consisting of hydrogen, halogen, alkyl, substituted alkyl, aryl, substituted aryl, arylalkyl, substituted arylalkyl, aryloxyalkyl and substituted aryloxyalkyl. In an alternative embodiment, $R^5$ and $R^6$ and the carbons to which they are bound, join to form an optionally substituted 9- or 10-ring atom carbocyclic or heterocyclic fused ring system. Typical 9- or 10-atom fused ring systems include, but are not limited to, napthalyl, 1,3-benzodioxolyl, 2,3-benzofuranyl, 1,4-benzodioxanyl, benzimidazoyl, benzothiazolyl etc.

Within the scope of the above Formula I, certain embodiments are preferred. In Formula I, one preferred embodiment is that in which $R_1$ is a functional group including, but not limited to, substituted arylalkyl, substituted aryl, substituted alkyl and substituted heterocyclic groups. Examples of such functional groups include, but are not limited to, the following:

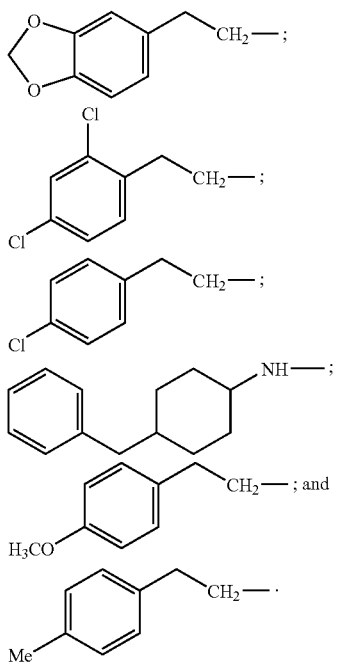

Another preferred embodiment is that in which $R_2$ is a functional group including, but not limited to, substituted alkyl, heterocyclic and substituted heterocyclic groups. Examples of such functional groups include, but are not limited to, the following:

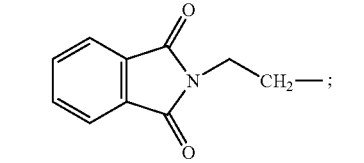

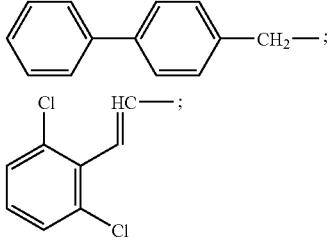

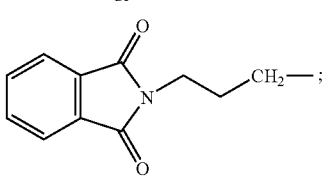

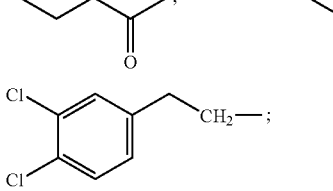

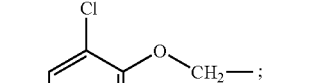

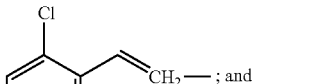

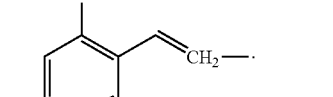

In one embodiment, $R_2$ is a functional group other than a nitrogen-bonded cyclic α-amino acid or ester thereof.

Also preferred is the embodiment in which $R_3$ is a functional group including, but not limited to, substituted alkyl and substituted aryl groups. Examples of such functional groups include, but are not limited to, the following:

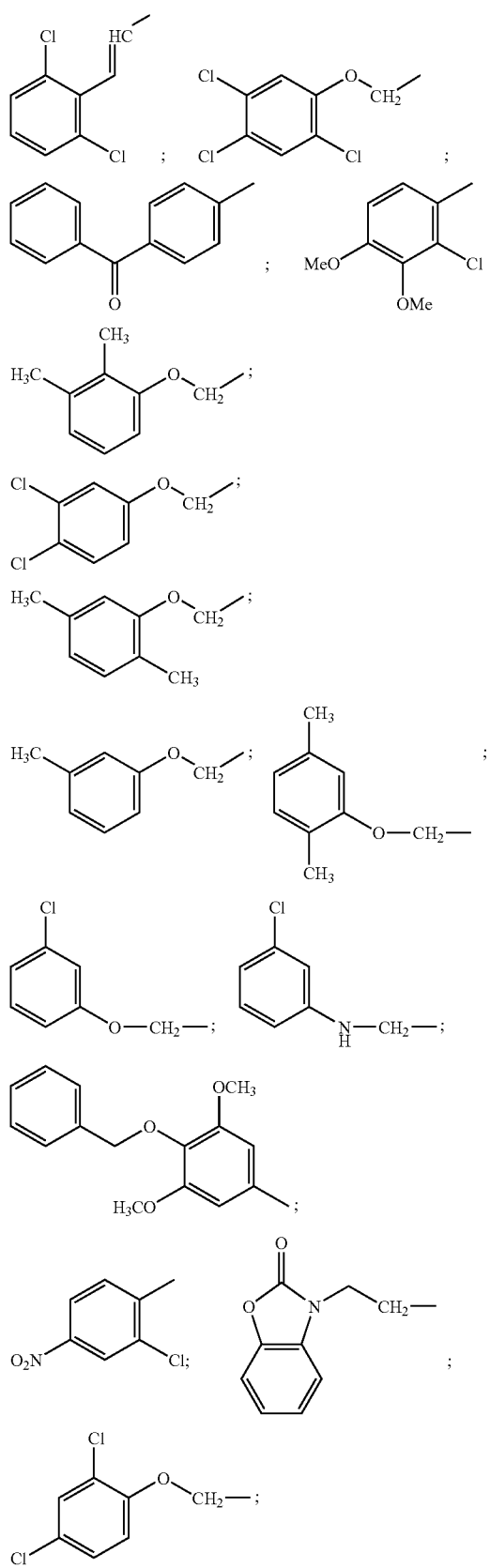

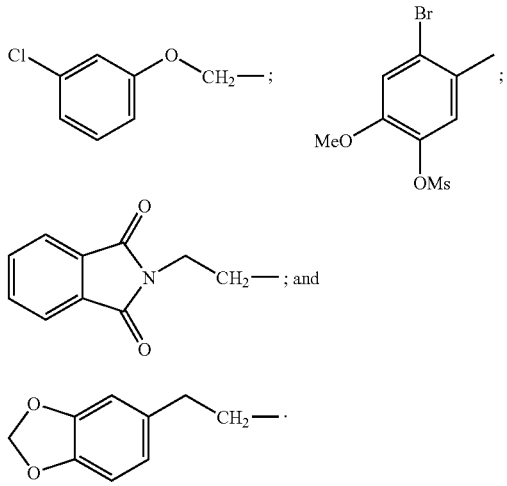

In another preferred embodiment, $R^5$ and $R^6$ and the carbons to which they are bound join to form an optionally substituted napthalene ring. In other preferred embodiments, $R_5$ and $R_6$ are both hydrogen or $R_5$ is hydrogen and $R_6$ is a meta or para substituent.

In Formula I, the benzyl ring may be replaced by the substituent $R_4$ (see below). In this embodiment, $R_4$ can be a member selected from the group consisting of alkyl, substituted alkyl, aryl, substituted aryl, arylalkyl, substituted arylalkyl, aryloxyalkyl, substituted aryloxyalkyl, heteroaryl, substituted heteroaryl, heteroarylalkyl, substituted heteroarylalkyl, heterocycles, substituted heterocycles, heterocyclicalkyl and substituted heterocyclicalkyl.

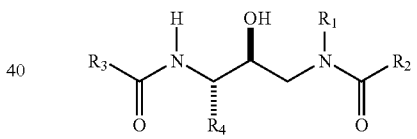

It will be readily apparent to those of skill in the art that depending on the substituents, the compounds of Formula I can be a racemic mixture (mixtures of diastereomers or enantiomers) or as stereochemically distinct compounds. However, in a preferred embodiment, the compounds of the present invention have the following stereochemistry:

Formula I

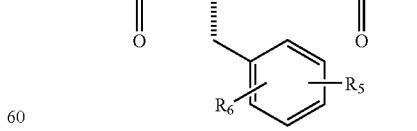

Tables I and II set forth compounds in accordance with the present invention that are particularly preferred. The compounds in Table I and throughout this specification are often referred to by code numbers, which are used for convenience only, and are strictly arbitrary for purposes of this invention.

TABLE I
Exemplar Aspartyl Protease Inhibitors
| Compound Code No. | Protease Binding Compounds Formula |
|---|---|
| EAA | 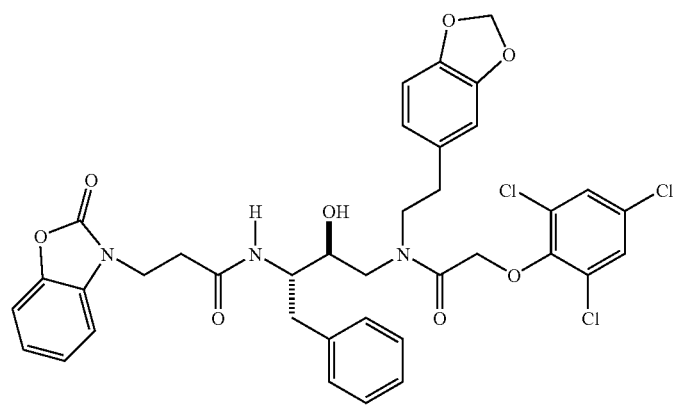 |
| EFA | 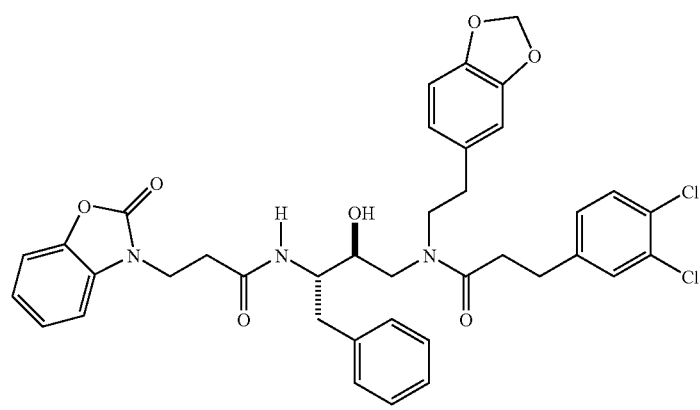 |
| EHA | 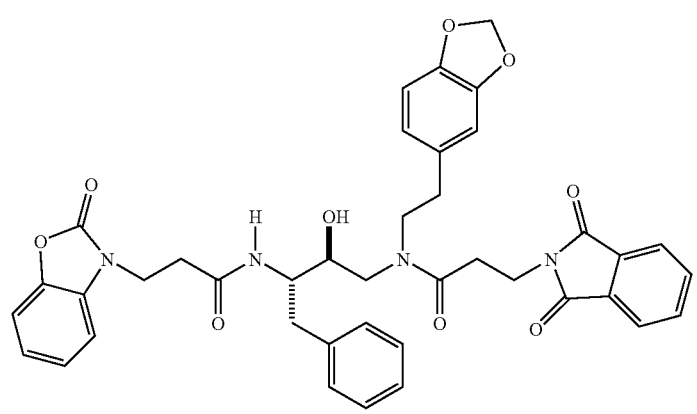 |

TABLE I-continued
Exemplar Aspartyl Protease Inhibitors
| Compound Code No. | Protease Binding Compounds Formula |
|---|---|
| FAA | 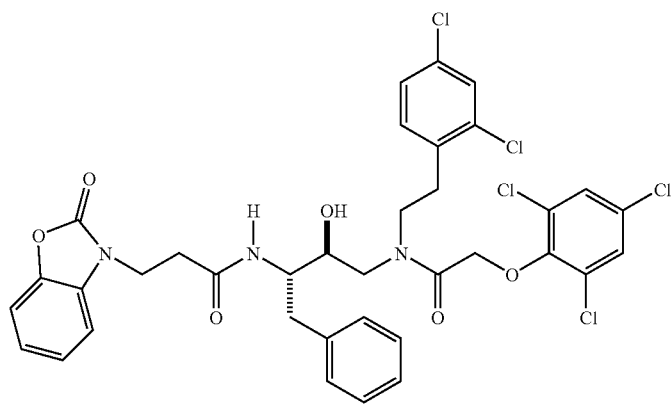 |
| FFA | 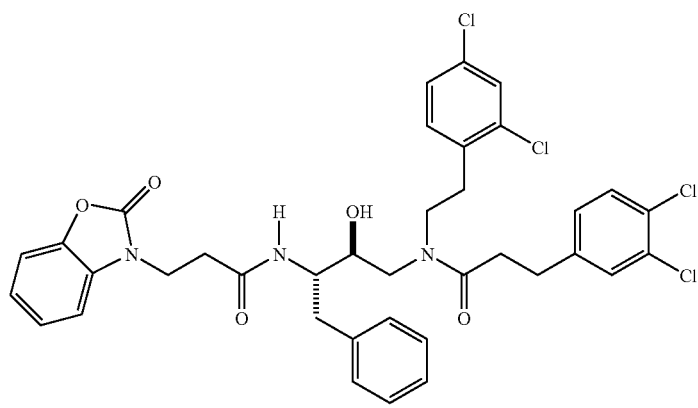 |
| FHA | 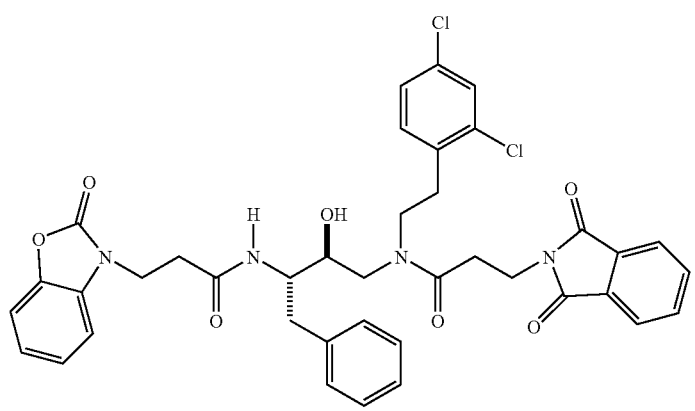 |

TABLE I-continued
Exemplar Aspartyl Protease Inhibitors
| Compound Code No. | Protease Binding Compounds Formula |
|---|---|
| EHB | 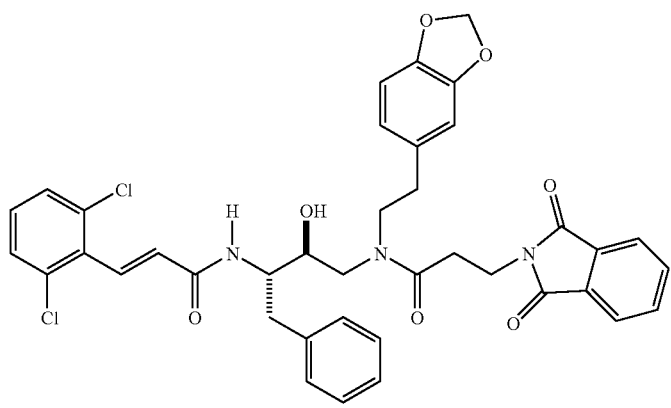 |
| EFD | 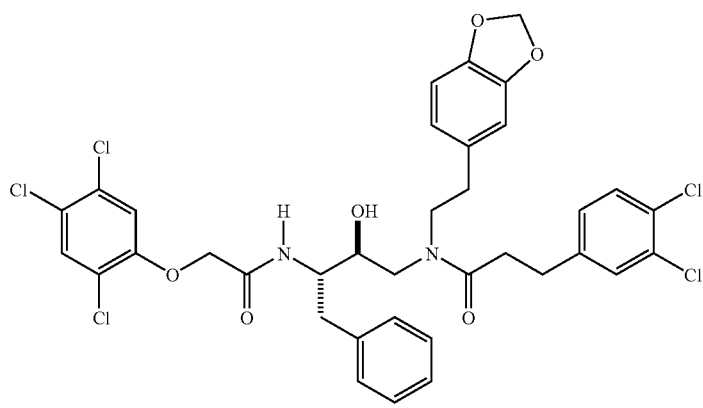 |
| EHD | 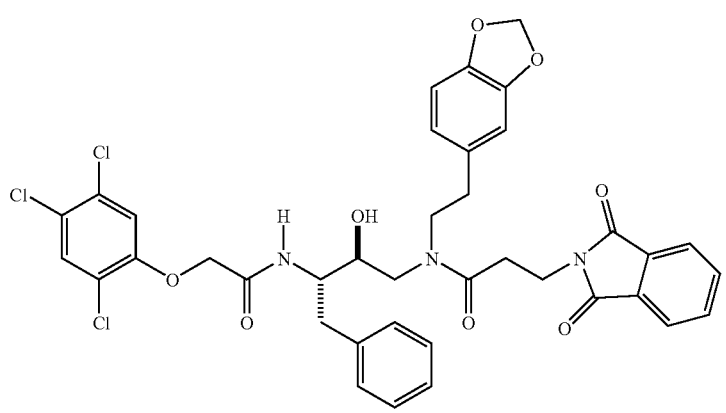 |

TABLE I-continued
Exemplar Aspartyl Protease Inhibitors
| Compound Code No. | Protease Binding Compounds Formula |
|---|---|
| EEF | 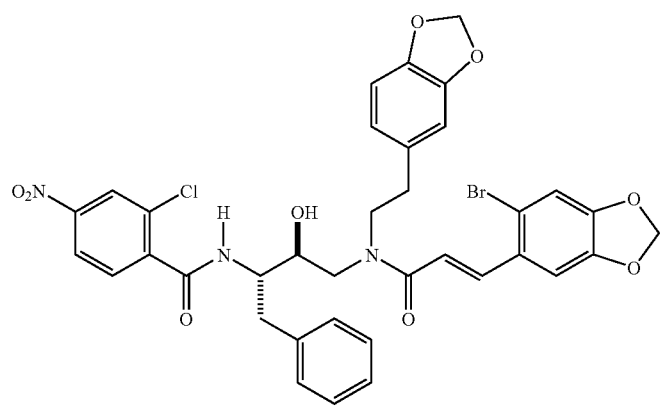 |
| EHF | 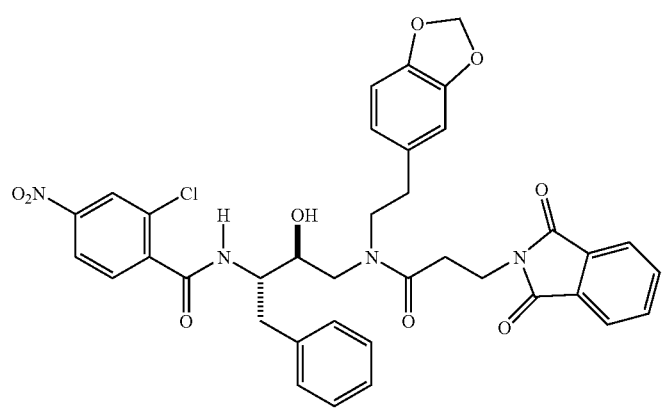 |
| FHF | 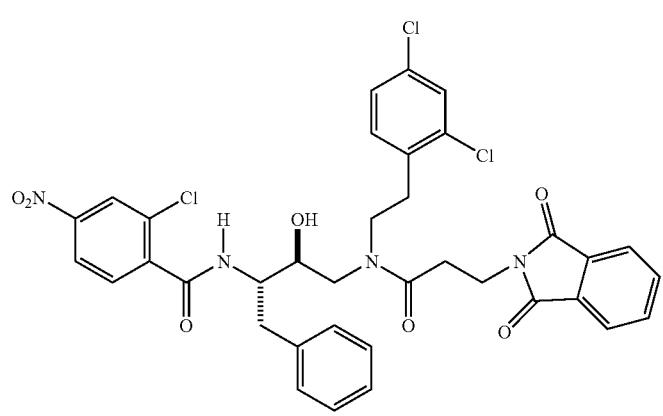 |

TABLE I-continued
Exemplar Aspartyl Protease Inhibitors
| Compound Code No. | Protease Binding Compounds Formula |
|---|---|
| EFH | 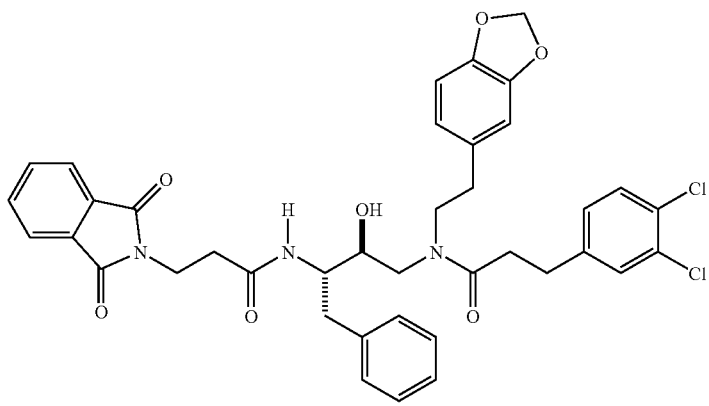 |
| EHH | 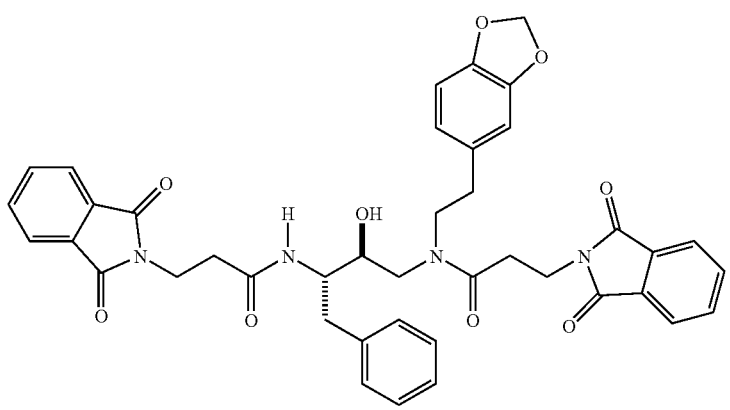 |
| FFH | 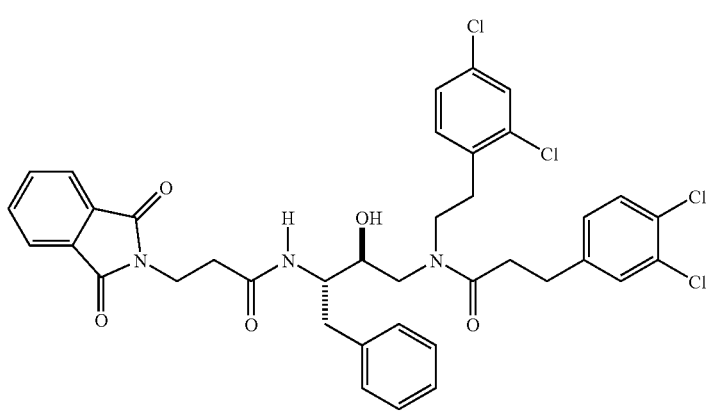 |

TABLE I-continued
Exemplar Aspartyl Protease Inhibitors
| Compound Code No. | Protease Binding Compounds Formula |
|---|---|
| FAH | 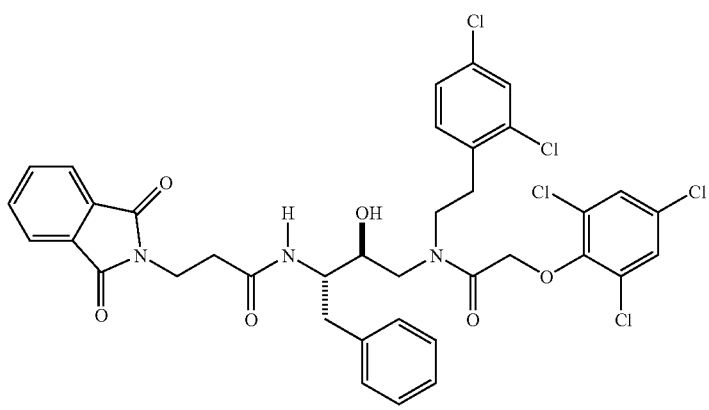 |
| EFI | 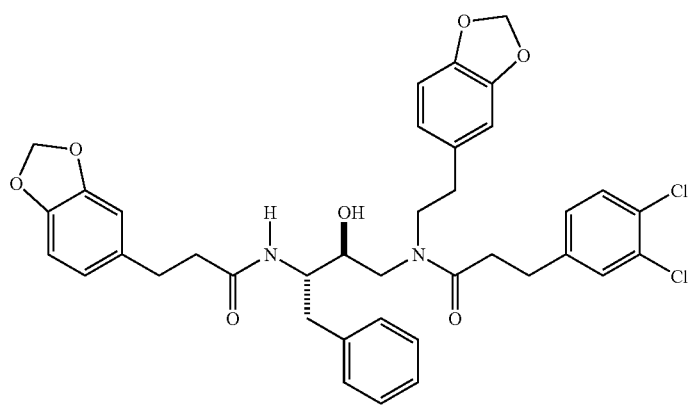 |
| EHI | 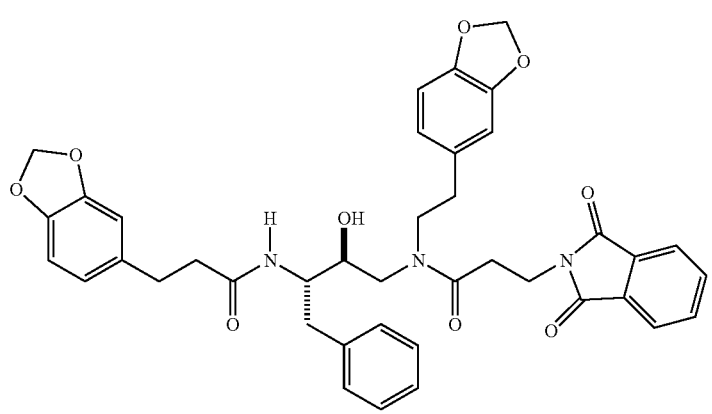 |

TABLE I-continued
Exemplar Aspartyl Protease Inhibitors
| Compound Code No. | Protease Binding Compounds Formula |
|---|---|
| EAJ | 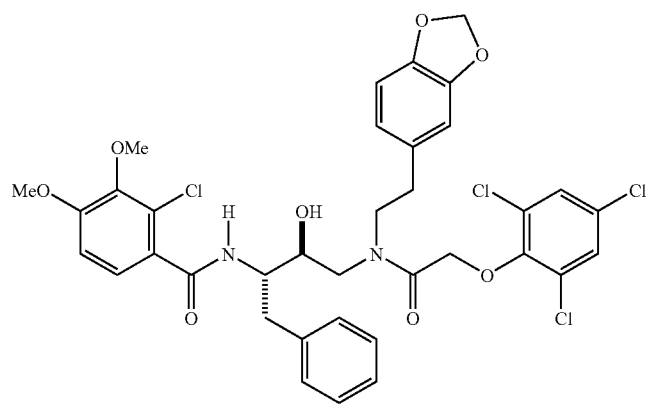 |
| EFJ | 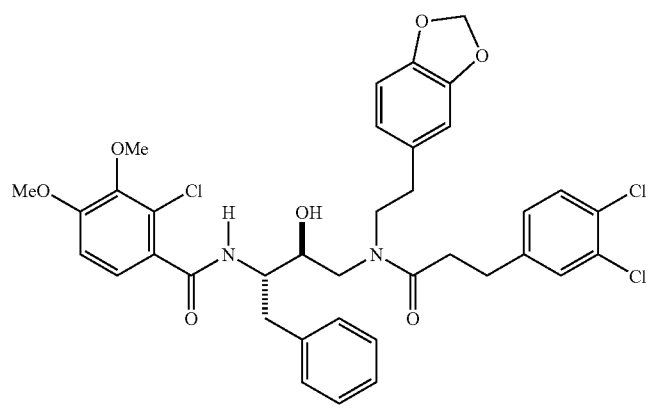 |
| EGJ | 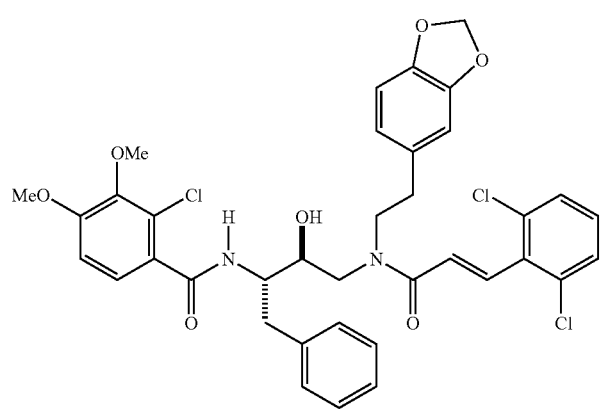 |

TABLE I-continued
Exemplar Aspartyl Protease Inhibitors
| Compound Code No. | Protease Binding Compounds Formula |
|---|---|
| EHJ | 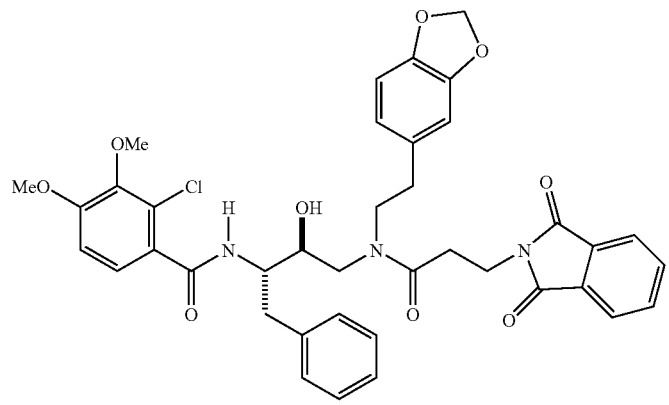 |
| FHJ | 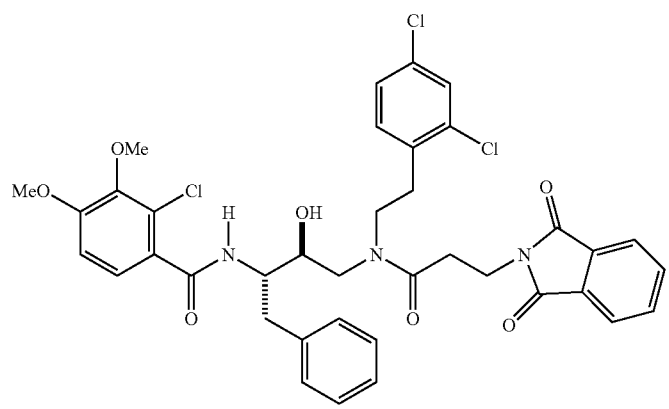 |
| EHO | 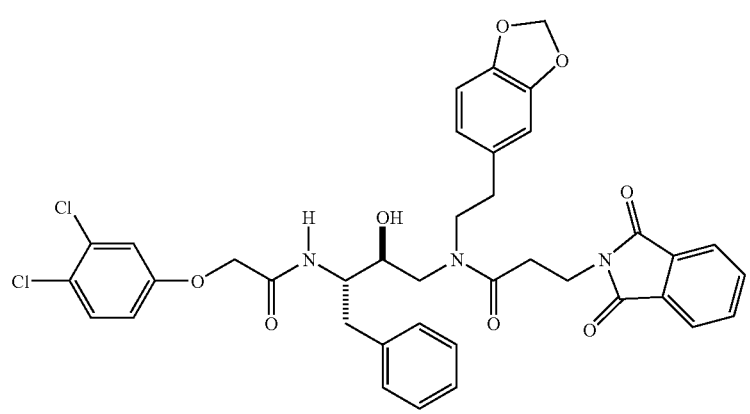 |

TABLE I-continued
Exemplar Aspartyl Protease Inhibitors
| Compound Code No. | Protease Binding Compounds Formula |
|---|---|
FHO
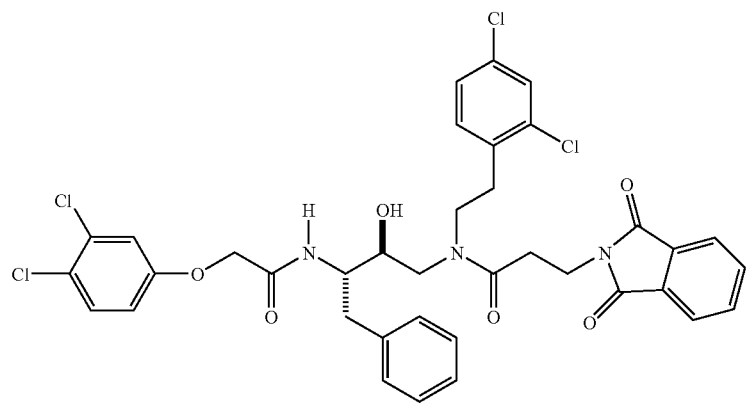
EHM
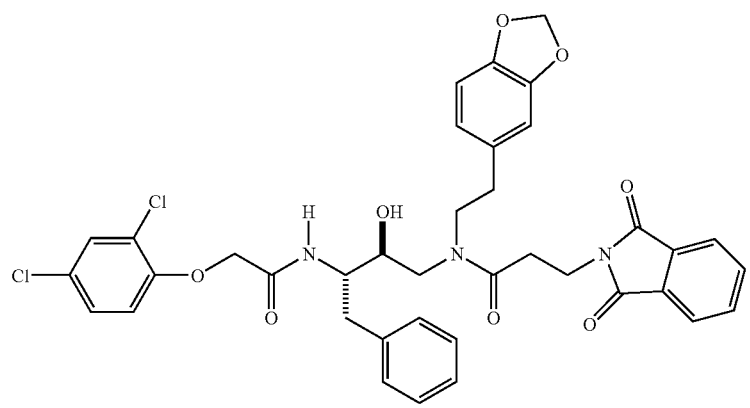
EHR
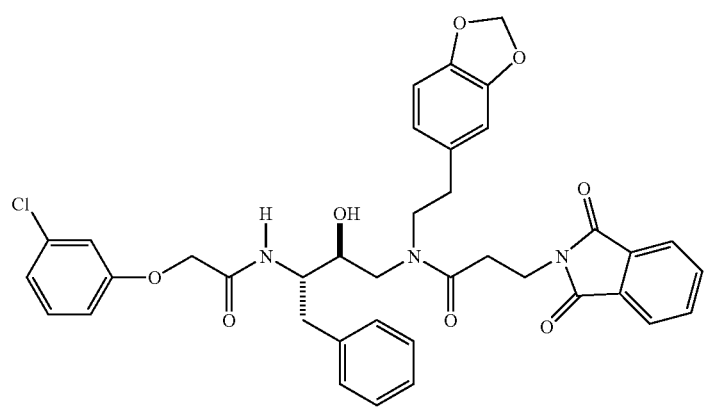

TABLE I-continued
Exemplar Aspartyl Protease Inhibitors
| Compound Code No. | Protease Binding Compounds Formula |
|---|---|
| EHS | 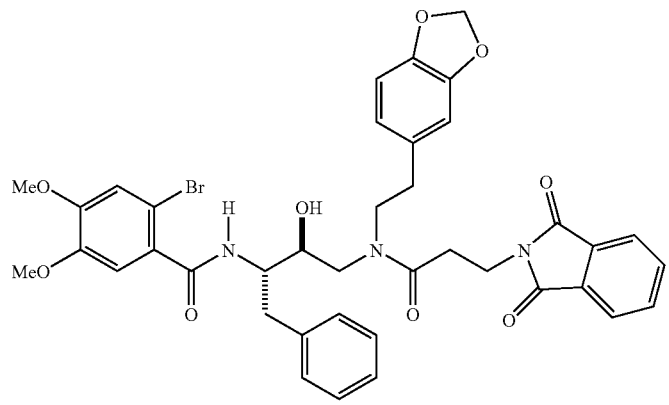 |
| UHD | 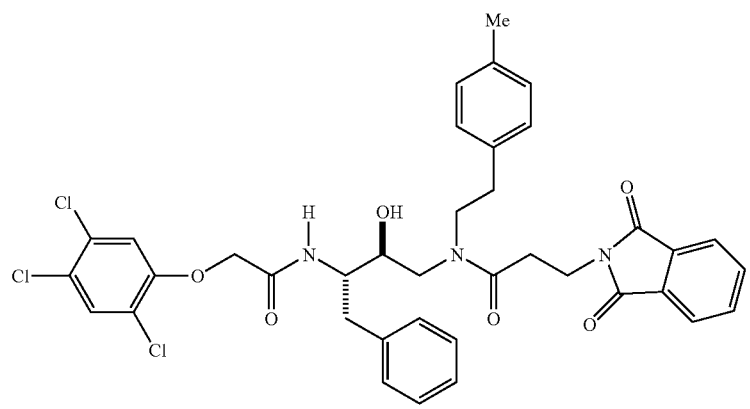 |
TABLE II
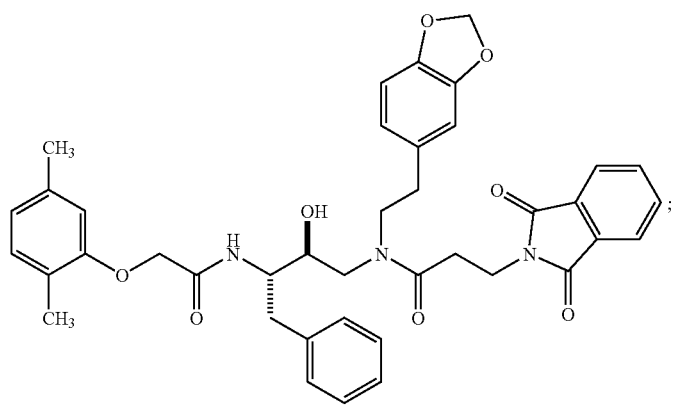

TABLE II-continued
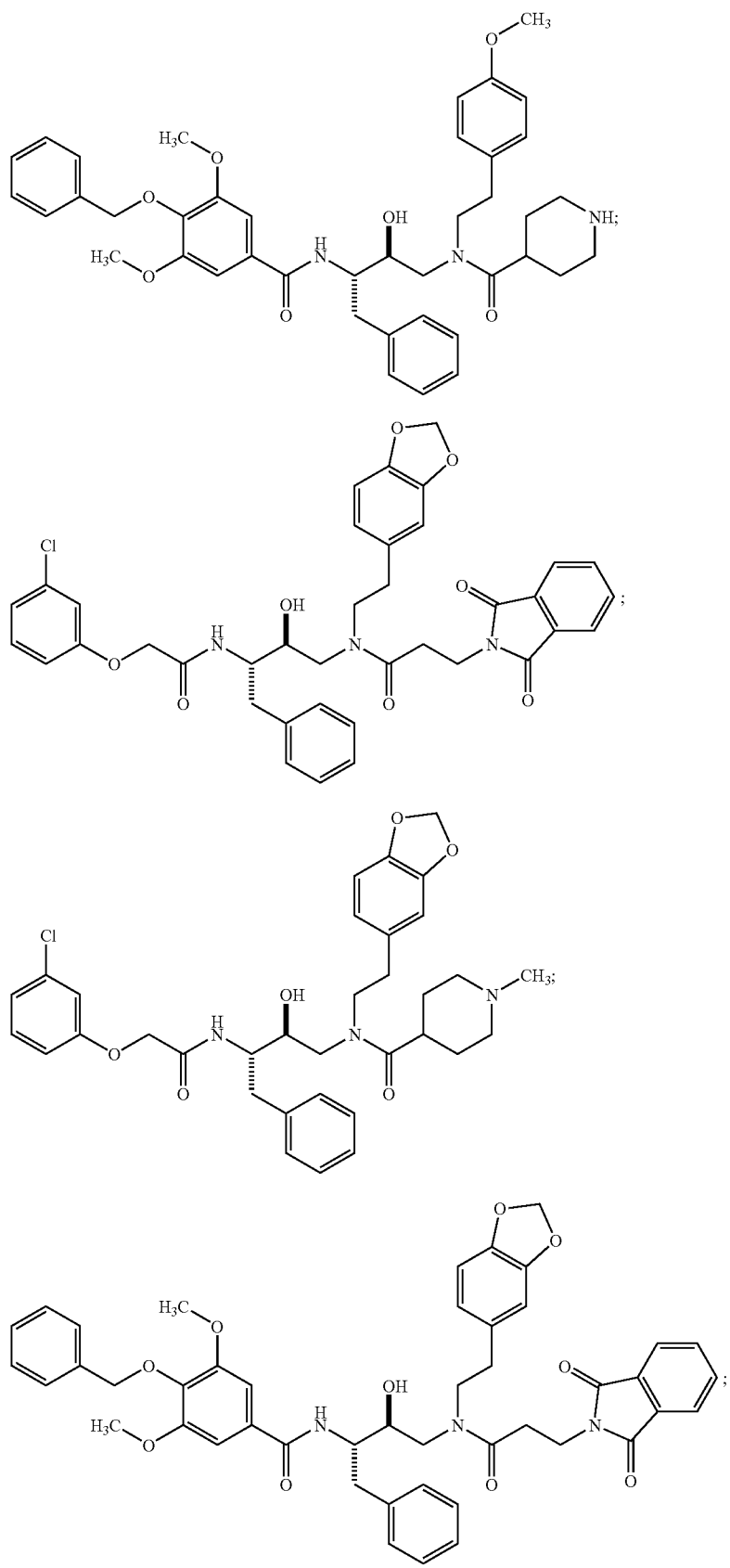

TABLE II-continued
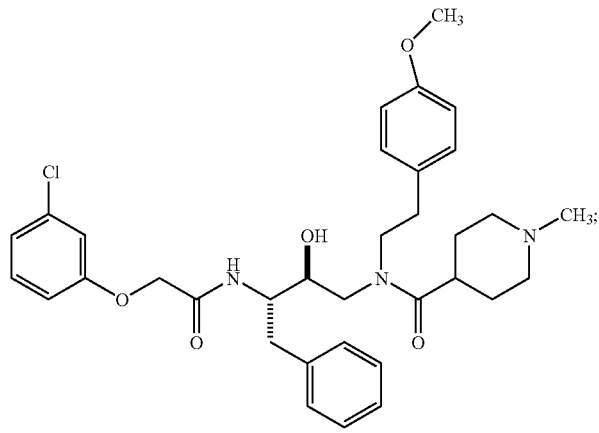
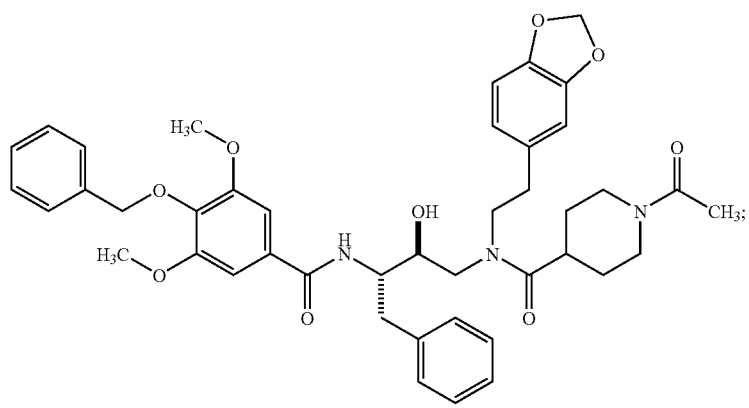
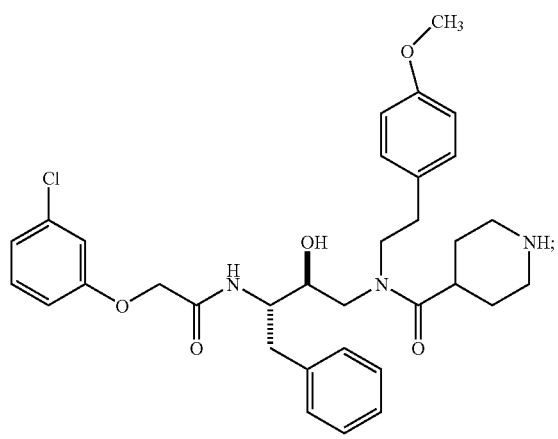

TABLE II-continued

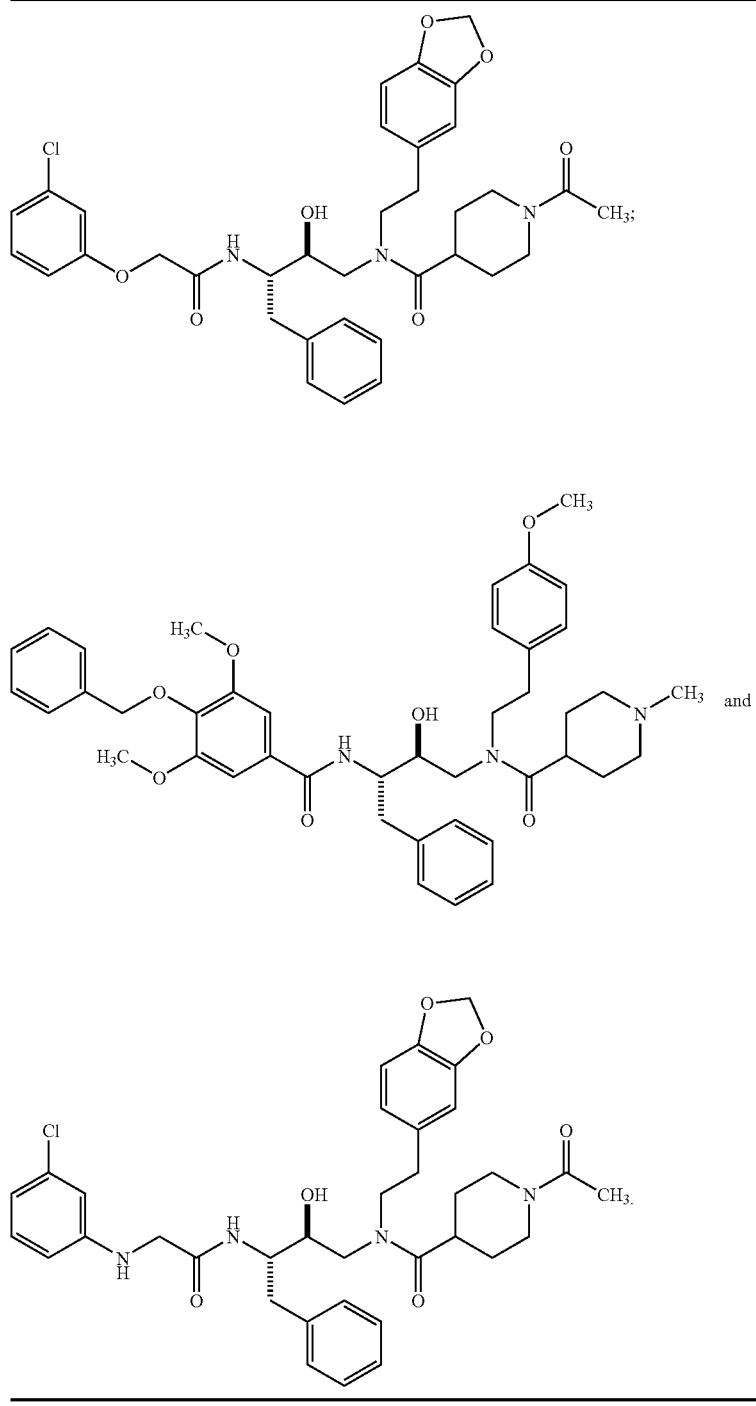

The compounds of the present invention can be synthesized in a variety of ways, using conventional synthetic chemistry techniques. Typically, the compounds of the present invention are prepared according to the reaction scheme set forth in FIG. 2, wherein $R_1$, $R_2$ and $R_3$ are as defined above. The use of appropriate organic solvents, temperature and time conditions for running the reactions are within the level of skill in the art. Reactions of this type are generally described by E. K. Kick and J. A. Ellman, *J. Med. Chem.* 38, 1427–1430 (1995), the teachings of which are hereby incorporated by reference.

C. Uses For the Aspartyl Protease Inhibitors

The compounds of the present invention have been found to be potent inhibitors of aspartyl proteases and, in particular, cathepsin D. As such, the present invention contemplates using the compounds of the present invention to inhibit cathepsin D, either in vivo or in vitro. In one embodiment, the present invention provides a method of inhibiting cathepsin D, the method comprising contacting cathepsin D with an aspartyl protease inhibitor having the general formula:

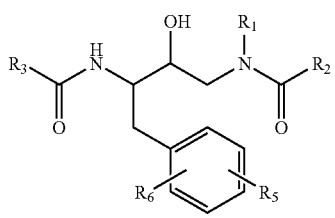

In the above formula, $R_1$, $R_2$ and $R_3$ are members independently selected from the group consisting of alkyl, substituted alkyl, aryl, substituted aryl, arylalkyl, substituted arylalkyl, aryloxyalkyl, substituted aryloxyalkyl, heteroaryl, substituted heteroaryl, heteroarylalkyl, substituted heteroarylalkyl, heterocycles, substituted heterocycles, heterocyclicalkyl and substituted heterocyclicalkyl. The prior discussions pertaining to $R_1$, $R_2$ and $R_3$ and their preferred embodiments are fully applicable to the aspartyl protease inhibitors used in this method of the present invention and, thus, will not be repeated with respect to this particular method. $R_5$ and $R_6$ are as defined above.

In another embodiment, the present invention provides a method of inhibiting protein processing by cathepsin D in living cells, the method comprising contacting the cells with an effective amount of a compound having the general formula:

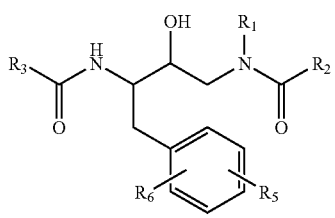

The prior discussions pertaining to $R_1$, $R_2$, $R_3$, $R_5$ and $R_6$ and their preferred embodiments are fully applicable to the aspartyl protease inhibitors used in this method of the present invention and, thus, will not be repeated with respect to this particular method.

Compounds capable of inhibiting cathepsin D can readily be identified using the assays described herein which measure a change in the hydrolysis of a peptide substrate. More particularly, a fluorometric high through-put assay for activity toward human liver cathepsin D (Calbiochem) can be used to screen the compounds of the present invention for their ability to inhibit cathepsin D. This assay was previously described by G. A. Kraft, et al., *Methods Enzymol.* 241, 70–86 (1994), the teachings of which are incorporated herein by reference. Moreover, the peptide substrate (Ac-Glu-Glu(Edans)-Lys-Pro-Ile-Cys-Phe-Phe-Arg-Leu-Gly-Lys(Methyl Red)-Glu-NH$_2$) used in the assay has been previously reported ($K_m$=6 µM) (E. T. Baldwin, et al., *Proc. Natl. Acad. Sci., U.S.A.* 90, 6796–6800 (1993)). Generally, the reactants are mixed, the reaction is allowed to proceed for a specific period of time and the fluorescence of the reaction products is monitored to determine the extent to which the peptide substrate has been cleaved. Compounds found to exhibit inhibitory activity towards cathepsin D using the foregoing assay can be synthesized on a larger scale and a more detailed kinetic analaysis can be carried out using an assay similar to that set forth in Table IV, infra, and described in greater detail by G. A. Kraft, et al., *Methods Enzmol.* 241, 70–86 (1994). As such, following the methods of the present invention, compounds can be readily synthesized and screened to identify compounds that inhibit cathepsin D.

As explained above, the aspartyl protease inhibitors of the present invention modulate the processing of numerous proteins, such as amyloid precursor protein (APP), involved in diseases. In a presently preferred embodiment, the aspartyl proteases of the present invention are used to modulate the processing of APP. As such, in yet another embodiment, the present invention provides a method for modulating the processing of an amyloid precursor protein (APP), the method comprising contacting a composition containing the APP with an aspartyl protease inhibitor having the general formula:

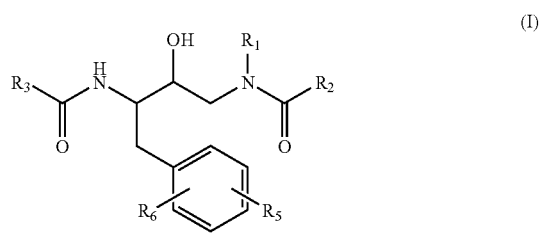

The prior discussions pertaining to $R_1$, $R_2$, $R_3$, $R_5$ and $R_6$ and their preferred embodiments are fully applicable to the aspartyl protease inhibitors used in this method of the present invention and, thus, will not be repeated with respect to this particular method.

The modulation of APP can be demonstrated in a variety of ways. For example, aspartyl protease inhibitors can be evaluated for the ability to modulate generation of Aβ or α-sAPP. In one preferred embodiment, the formation of Aβ is decreased compared to the amount formed in the absence of the aspartyl protease inhibitor. In another preferred embodiment, formation of α-sAPP is increased compared to the amount formed in the absence of the asparty protease inhibitor. In one embodiment, the composition is a body fluid. In a preferred embodiment, the body fluid is cerebral spinal fluid (CSF). Numerous in vitro and in vivo animal models can be used to screen a given aspartyl protease inhibitor for its ability to modulate APP processing. Exemplar assays are set forth below, in the Example Section and in, for example, Hoffman, et al., *Neuroscience Letters*, 250:75–78 (1998); Bahr, et al., *Experimental Neurology*, 129:81–94 (1994); and U.S. Pat. No. 5,872,101, the teachings of which are incorporated herein by reference. In addition, it will be readily apparent to those of skill in the art that a number of commercially available tests can be used to detect Aβ in a composition (e.g., CSF). For instance, the ADmark Assay, which is commercially available from Athena Neurosciences, Inc., can be used to detect Aβ in CSF.

1. In Vitro Assays

The aspartyl protease inhibitors provided herein yield a positive result in one or more in vitro assays that assess the effects of test compounds on processing of APP. In particular, in vitro assay systems for identifying such compounds are provided herein. These assays evaluate the effects of a test compound on processing of APP and use cultured human glioblastoma cell lines that have been transfected with DNA encoding either a wild-type 695 amino acid isoform of APP or a mutein of APP that contains changes (in this case two or three amino acid changes have been made) that appear to make the molecule more susceptible to proteolytic cleavage that results in increased production of Aβ (see, e.g., Mullan, et al., *Nature Genet.*, 1:345–347 (1992)).

In performing these assays, a test compound is added to the culture medium and, after a selected period of time, the culture medium and/or cell lysates are analyzed using immunochemical assays to detect the relative amounts of Aβ, total soluble APP (sAPP), a portion of sAPP designated α-sAPP, and C-terminal fragments of APP. In particular, the culture medium and cell lysates are analyzed by immunoblotting coupled with laser scanning densitometry and ELISAs using several different antibodies. A positive test occurs when: (1) there is a decrease in the approximately equal to 4-kDa amyloid β-protein (Aβ) in the medium relative to control cultures (4-kDa assay); and/or (2) the relative amount of sAPP in the medium increases; and/or (3) there is a decrease in the amount of C-terminal amyloidogenic fragments larger than 9 kDa and smaller than 22 kDa in the cell lysate as a result of differential processing; and/or (4) there is an increase in the amount of α-sAPP in the medium relative to control cultures. Control cultures can be cultures that have not been contacted with the compound. The Aβ assay is done using cells (e.g., HGB 717/Swed) that have been transfected with DNA encoding the mutein APP; the other assays are performed using cells, such as HGB695 cells, that have been transfected with DNA encoding a wild-type APP.

2. The Amount of α-sAPP and the Ratio of α-sAPP to Total sAPP in Cerebral Spinal Fluid (CSF) as an Indicator of Alzheimer's Disease (AD) and the Effectiveness of Therapeutic Intervention The relative amount of α-sAPP and the ratio of α-sAPP to total sAPP in CSF are known to be useful markers in the detection of neurodegenerative disorders characterized by cerebral deposition of amyloid (e.g., AD) and in monitoring the progression of such disease. Furthermore, assay systems incorporating these markers can be used in monitoring therapeutic intervention of these diseases.

The amount of α-sAPP and the ratio of α-sAPP to total sAPP in CSF samples can be used as an indicator of Alzheimer's Disease and other neurodegenerative disorders. For purposes herein, this amount and/or the ratio can also be used to assess the effectiveness of compounds provided herein in treating Alzheimer's Disease and neurodegenerative disorders.

It has been found that patients with suspected Alzheimer's disease (as diagnosed by other indicia, or confirmed by autopsy) have a statistically significant lower ratio of α-sAPP to total sAPP in CSF and also have statistically significant lower levels of α-sAPP. Therefore, by comparison with non-Alzheimer's disease controls or by existence of a ratio lower than a predetermined standard, based, for example, on averages in samples from large numbers of unafflicted individuals, or an amount of α-sAPP lower than a predetermined standard, Alzheimer's disease or, depending upon other indications, another neurodegenerative disease is indicated.

Compounds, such as the aspartyl protease inhibitors provided herein, that alter this ratio or the level of α-sAPP closer to that of individuals who do not have a neurodegenerative disorder characterized by the cerebral deposition of amyloid are considered useful for treating these disorders.

3. In Vivo Assays

The ability of compounds to modulate processing of APP can also be evaulated using in vivo assays (See, e.g., Lamb, et al., *Nature Genet.*, 5:22–29 (1993); Pearson, et al. *Proc. Natl. Acad. Sci. U.S.A.* 90:10578–10582 (1993); Kowall, et al., *Proc. Natl. Acad. Sci. U.S.A.*, 88:7247–7251 (1991)). Compounds can be administered through a canula implanted in the cranium of a rat or other suitable test animal. After a predetermined period of administration the rats are sacrificed. The hippocampi are evaluated in immunoblot assays or other suitable assays to determine the relative level of α-sAPP and C-terminal fragments of APP compared to untreated control animals. Aspartyl protease inhibitors that result in relative increases in the amount of α-sAPP are selected.

In still another embodiment, the present invention provides a method for modulating the processing of a tau-protein (τ-protein), the method comprising contacting a composition containing the τ-protein with an aspartyl protease inhibitor having the general formula:

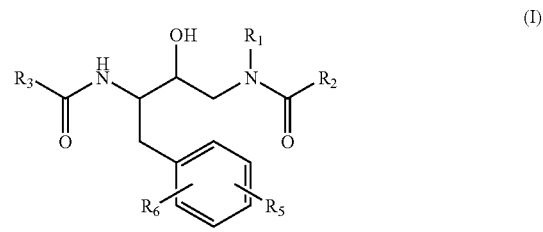

(I)

The prior discussions pertaining to $R_1$, $R_2$, $R_3$, $R_5$ and $R_6$ and their preferred embodiments are fully applicable to the aspartyl protease inhibitors used in this method of the present invention and, thus, will not be repeated with respect to this particular method.

The modulation of τ-protein can be demonstrated in a variety of ways. For example, aspartyl protease inhibitors can be evaluated for the ability to modulate generation of τ-fragments. In one preferred embodiment, the formation of τ-fragments is decreased compared to the amount formed in the absence of the aspartyl protease inhibitor. In one embodiment, the composition is a body fluid. In a preferred embodiment, the body fluid is cerebral spinal fluid (CSF). Numerous in vitro and in vivo animal models can be used to screen a given aspartyl protease inhibitor for its ability to modulate the processing of τ-protein. Exemplar assays are set forth below, in the Example Section and in, for example, Bednarski and Lynch, *J. Neurochem.*, 67(5):1845–1855 (1996); and U.S. Pat. No. 5,492,812, the teachings of which are incorporated herein by reference. In addition, it will be readily apparent to those of skill in the art that a number of commercially available tests can be used to detect τ-fragments in a composition (e.g., CSF). For instance, the ADmark Assay, which is commercially available from Athena Neurosciences, Inc., can be used to detect τ-proteins in CSF.

1. Partial Purification of τ and Proteolytic Assays with Cathepsin D and Test Compound τ-proteins can be partially purified from rat brain by using a modified version of the method reported by Lindwall and Cole, *J. Biol. Chem.*, 259:12241–12245 (1984). Brain tissue (~20 g) is homogenized in buffer A (20 mM MES, 80 mM NaCl, 2 mM EGTA, 0.1 mM EDTA, 1 mM MgCl₂, 1 mM 2-mercaptoethanol, pH 6.75) that additionally contains 0.1 mM GTP. Following configuration for 25 min at 30,000 g (all centrifugation steps described in this method occurred at 4° C.), the supernatant is made to 35% ammonium sulfate and kept on ice for 30 minutes. The slurry is centrifuged for 20 minutes at 10,000 g; supernatant is saved, made to 45% ammonium sulfate, and incubated on ice for 30 minutes. After centrifugation for 20 minutes at 15,000 g, the pellet is resuspended in ~4 mL of buffer A and made to 2.5% perchloric acid. Following a 15 minute incubation on ice, the slurry is centrifuged for 15 minutes at 15,000 g. The supernatant is made to 20% trichloroacetic acid, ice for 25 minutes and centrifuged for 15 minutes at 15,000 g. The pellet is resuspended in 95% ethanol and dried under vacuum.

To measure the ability of the aspartyl protease inhibitors of the present invention to modulate the processing, e.g., degradation, of partially purified τ by cathepsin D, protease, test compound and substrate are combined and incubated at 37° C. for various durations. Partially purified τ is first resuspended in assay buffer (50 mM citric acid/sodium citrate buffer, pH 4.0). Reactions are initiated by the addition of human liver cathepsin D (1 U; Calbiochem, San Diego, Calif., U.S.A.) and test compound to 0.1 mg of τ and terminated by removing aliquots at the designated time, adding SDS and 2-mercaptoethanol, and boiling for 5 minutes. One unit of cathepsin D is defined as the amount of enzyme that generates an increase in absorbance (at 280 nm) of 1.0 per hour when co-incubated with hemoglobin in 10% trichloroacetic acid. The specific activity of the enzyme is 300 U/mg of protein, and its purity is greater than 98% by SDS-PAGE.

2. Assay for the Proteolysis of τ in Cortical Homogenates by Exogenous Cathepsin D and Test Compounds Brains from 3-month-old Sprague-Dawley rats are removed and dissected in artificial cerebrospinal fluid (124 mM NaCl, 20 mM glucose, 5 mM HEPES, 3 mM KCl, 1.25 mM KH$_2$PO$_4$, 2.8 mM MgSO$_4$, 2 mM CaCl$_2$, mM NaHCO$_3$, 0.5 mM ascorbate, Ph 7.4). Frontal cortices are homogenized (Teflon to glass, 10 strokes) in 7 mM HEPES buffer, pH 7.35, additionally containing 135 mM NaCl, 2 mM EDTA, 2 mM EGTA, and 2.0 μM Okadaic acid. Slurries are centrifuged at 1,000 g for five minutes at 4° C. The supernatant is collected, sonicated, and subjected to two freeze/thaw cycles.

Proteolytic assays are conducted by co-incubating 0.1 mg of the supernatant described above with 0.35 U of human liver cathepsin D and the test compound. The enzyme-to-substrate ratio should be about 1:86 (wt/wt). The reaction is allowed proceeded at constant pH for 5 hours at 37° C. and is terminated by adding SDS and 2-mercaptoethanol and boiling the samples for five minutes.

As explained above, aspartyl proteases, e.g., cathepsin D, are enzymes that plays an important role in protein metabolism, catabolism and antigen processing. As a result of their ability to inhibit aspartyl proteases, the compounds of the present invention can be used for a number of therapeutic applications. As such, in yet another embodiment, the present invention provides a method of treating a neurodegenerative disorder, the method comprising: administering to a mammal a therapeutically effective amount of an aspartyl protease inhibitor and a pharmaceutically acceptable carrier or excipient, the aspartyl protease inhibitor having the general formula:

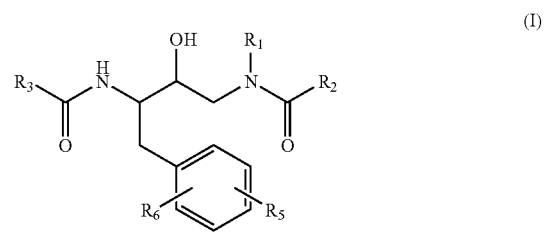

The prior discussions pertaining to $R_1$, $R_2$, $R_3$, $R_5$ and $R_6$ and their preferred embodiments are fully applicable to the aspartyl protease inhibitors used in this method of the present invention and, thus, will not be repeated with respect to this particular method.

In one embodiment, the neurodegenerative disorder is characterized by the accumulation of amyloid plaques. In another embodiment, the neurodegenerative disorder is characterized by the accumulation of τ-fragments. As such, the aspartyl protease inhibitors of the present invention can be used to treat all amyloid-pathology related diseases and all tau pathology-related diseases. Examples of such neurodegenerative diseases include, but are not limited to, the following: Alzheimer's disease, Parkinson's disease, cognition deficits, Downs Syndrome, cerebral hemorrhage with amyloidosis, dementia (e.g., dementia pugilistica) and head trauma.

The compounds, i.e., aspartyl protease inhibitors, of the present invention can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the compounds can be achieved in various ways, including oral, buccal, rectal, parenteral, intraperitoneal, intradermal, transdermal, intracheal, etc., administration. Suitable formulations for use in the present invention are found in *Remington's Pharmaceutical Sciences* (Mack Publishing Company, Philadelphia, Pa., 17th ed. (1985)), which is incorporated herein by reference. In addition, for a brief review of methods for drug delivery, see, Langer, *Science* 249:1527–1533 (1990), which is incorporated herein by reference.

The compounds of the present invention can be administered alone, in combination with each other, or they can be used in combination with other known compounds (e.g., other protease inhibitors). In pharmaceutical dosage forms, the compounds may be administered in the form of their pharmaceutically acceptable salts, or they may also be used alone or in appropriate association, as well as in combination with other pharmaceutically active compounds. The following methods and excipients are merely exemplary and are in no way limiting. It should be noted that since the compounds of the present invention are non-peptidic in nature, they tend to have better pharmacokinetic properties (e.g., better oral availability and increased circulating half-lives) than compounds that are peptidic in nature.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Preferred formulations of the compounds are oral preparations, particularly capsules or tablets containing each from about 10 milligrams up to about 1000 milligrams of active ingredient. The compounds are formulated in a variety of physiologically compatible matrixes or solvents suitable for ingestion or injection.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

I. Example I

A. Specific Approach

One powerful strategy to target an enzyme class is to incorporate a stable mimetic or isostere of the transition state or of an intermediate of the enzyme-catalyzed reaction (R. A. Wiley, et al., Med. Res. Rev. 13, 327–384 (1993)). The libraries for potential cathepsin D inhibitors are based upon the well-known hydroxyethylamine isostere (see, FIG. 1). For the initial libraries, the $P_1$ side chain ($R_4$) is held constant, based on the benzyl substituent, based on the X-ray crystallographic structure of cathepsin D complexed with the natural peptide inhibitor pepstatin (E. T. Baldwin, et al., Proc. Natl. Acad. Sci., U.S.A. 90, 6796–6800 (1993)), and upon inhibition constants of peptide-based inhibitors (R. A. Jupp, et al., Biochem. J. 265, 871–878 (1990); N. S. Agarwal, etc., J. Med. Chem. 29, 2519–2524 (1986)).

In a pilot study both S and R epimers at the hydroxyl-carbon (see, structures 1 and 2 of FIG. 1) were prepared since both diastereomers have been found in potent inhibitors of other aspartic acid proteases (R. A. Wiley, et al., Med. Res. Rev. 13, 327–384 (1993)). Because inhibition at 1 µM was only found with compounds of scaffold 1 in the pilot study, further syntheses of libraries toward cathepsin D used only scaffold 1. Computer modeling (see below) predicted that structure 1 (FIG. 1) would provide the most potent inhibitors. Diversity is introduced in three positions: a primary amine for the $R_1$ substituent and acylating agents for the $R_2$ and $R_3$ substituents (FIG. 2). The optimization of the synthesis sequence was previously reported (E. K. Kick, J. A. Ellman, J. Med. Chem. 38, 1427–1430 (1995)).

The library synthesis was designed to use commercially available compounds for incorporation of the functionality at $R_1$, $R_2$, and $R_3$. Exhaustive combination of available materials would provide a library of over 10 billion compounds. To reduce these possibilities in a sensible way, version 93.2 of the Available Chemical Directory (ACD) from MDL Information Systems (San Leandro, Calif.) was used to search for all amines, carboxylic acids, sulfonyl chlorides and isocyanates with MW<275 daltons. Compounds with functionality obviously incompatible with the synthesis were eliminated. The resulting list included approximately 700 amines and 1900 acylating agents. However, this list still provided access to more than 1 billion compounds. Clearly, additional selection criteria were required, and a computational screening process was turned to in an effort to enhance selection.

B. Directed Library Design

Figure 3:
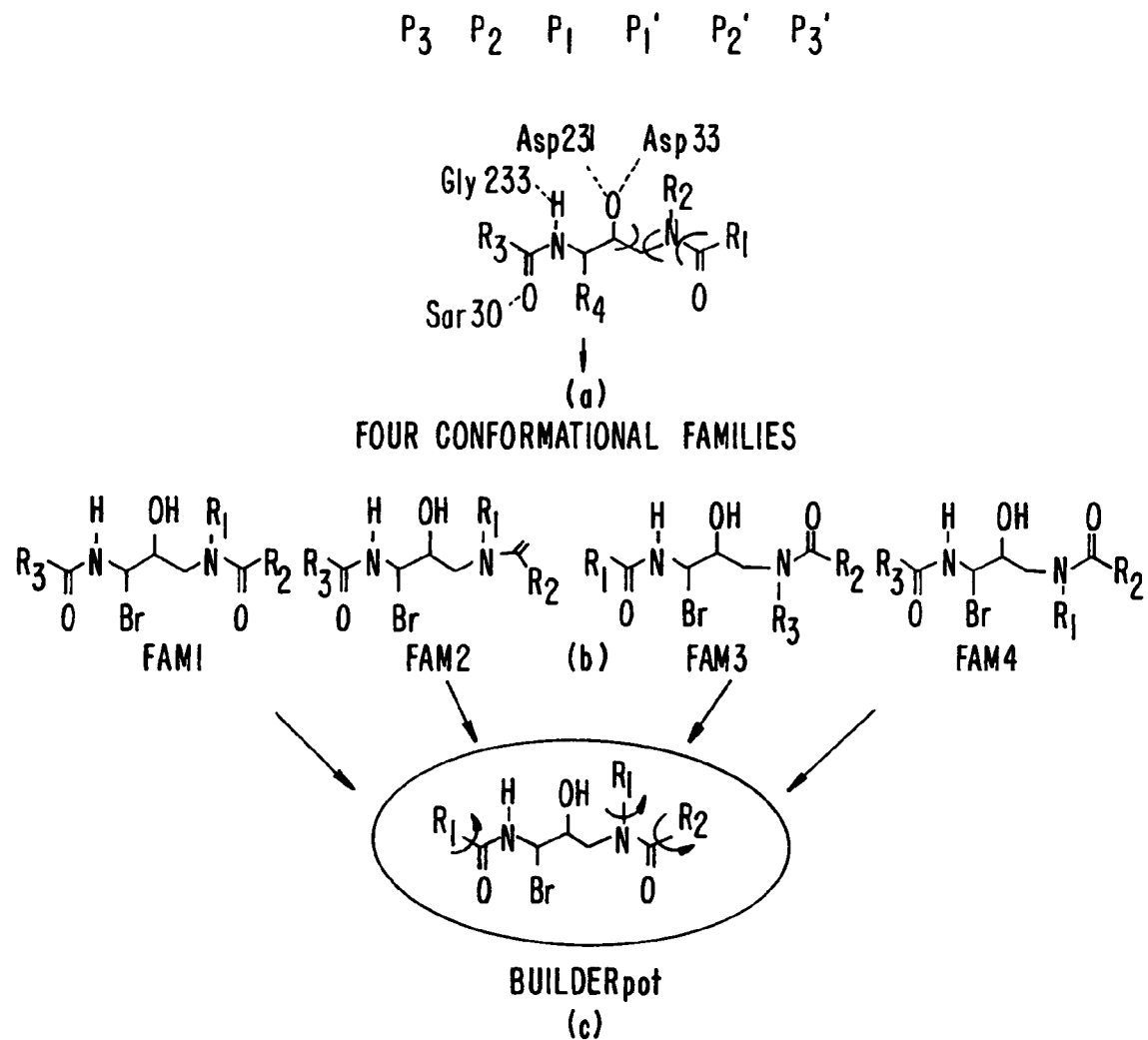
FIG. 3 illustrates the used of BUILDERopt in designing the combinatorial library: (a) Modeling the Scaffold. Coordinates and $P_1$–$P_3$ conformations of the pepstatin inhibitor were used as the starting geometry for hydroxyethylamine scaffold. Methyl groups were placed at each of the scaffold's $R_1$–$R_4$ positions. (b) Scaffold Conformation. A conformational search about the three torsion angles of the scaffold yielded 4 conformational families. A benzyl sidechain (Bn) was added to each of these families at the $R_4$ position. (c) Evaluating library components. The program BUILDERopt performed a limited conformational search on all possible components at each variable position ($R_1$–$R_3$) on each family, and scored the components by their potential interaction with cathepsin D. The top scoring candidates for each family were merged.

The structure-based design process began with coordinates for pepstatin in a complex with cathepsin D (E. T. Baldwin, et al., Proc. Natl. Acad. Sci., U.S.A. 90, 6796–6800 (1993)). The scaffold is identical to pepstatin on the $P_1$–$P_3$ side, but differs on the $B_{1'}$–$P_{3'}$ side and cannot form the same hydrogen bonds with the enzyme (FIG. 3A). Thus, the pepstatin positions for the $P_1$–$P_3$ side were used and the three scaffold torsion angles on the $P_{1'}$–$P_{3'}$ side were systemically rotated. Each rotation was followed by energy minimization within the cathepsin D active site, using the AMBER (S. J. Weiner, et al., J. Am. Chem. Soc. 106, 765–784 (1984)) force field in Sybyl, a molecular modeling software package from Tripos Associates (St. Louis, Mo.). During minimization, the enzyme was kept rigid, but full flexibility of the scaffold was allowed. Both S and R epimers, structures 1 and 2, were modeled using methyl groups for each of the $R_1$–$R_4$ groups.

The conformational energies of the R epimers were generally ca. 2 kcal higher than for S epimers, leading to the prediction that the S epimers would bind more tightly than the R epimers. All minimized conformations of S epimers within a 2 kcal/mol range were collected and clustered into four families based on geometric similarity (FIG. 3B). A benzyl group was added to each family at the $R_4$ position. The processed list of compounds for the ACD was passed through Sybyl to obtain Gasteiger and Marsili partial atomic charges for each component (J. Gasteiger, et al., *Tetrahedron Lett* 36, 3219 (1980); J. Gasteiger, M. Marsili, Organ. Magn. Reson. 15, 353 (1981)). To reduce the computational time for searching the components, compounds with more than 4 torsional bonds were identified and removed. A new feature of the BUILDER molecular modeling program (R. A. Lewis, et al., *J. Mol. Graphics* 10, 66–78 (1992); D. C. Roe, and Kuntz, I. D., *JCAMD* 9, 269–282 (1995)), called BUILDERopt (D. C. Roe, Dissertation, University of California, San Francisco (1995)), was used to position each of the $R_1$, $R_2$, and $R_3$ components onto the scaffold and to perform a full conformational search for the torsion angles of the substituent at 15 degree increments. In order to reduce the combinatoric problem, the $R_1$, $R_2$, and $R_3$ components were examined independently, but a probability-based clash grid was constructed to identify $R_1$ and $R_2$ conformations that might overlap. For example, if an $R_1$ conformation clashed with more than 50% of the $R_2$ components, that conformation was discarded. Each rotation was then examined for intramolecular clashes with the scaffold and overlap with cathepsin D. Each accepted conformation was rigid-body minimized (D. A. Gschwend, et al., *J. Compt-Aided Drug Design* 10, 123–132 (1996)) and scored with a force-field grid (E. C. Meng, et al., *J. Comput. Chem.* 13, 505–524 (1992)). The total computer time required to evaluate all torsion angles for all sidechains attached to four different scaffold conformations was 16 hours on a Silicon Graphics Iris R4400. The fifty best scoring components for all families were merged for each of the three variable positions, and sorted by overall lowest score. Components with cost above $35/gm were removed, leaving 34, 35, and 41 components at $R_1$, $R_2$ and $R_3$, respectively. Each remaining component was structurally fingerprinted (Daylight Clustering Toolkit, Daylight Chemical Information Systems, Inc., Santa Fe, N. Mex.) and hierarchically clustered (similarity cutoff=0.63) (H. C. Romesburg, *Cluster Analysis For Researchers* (Lifetime Learning Publications, Belmont, Calif., 1984)) using the Tanimoto similarity metric (P. Willett, *Similarity and Clustering in Chemical Information Systems* (John Wiley & Sons, New York, N.Y., 1987); P. Willett, et al., *J. Chem. If. Comput. Sci.* 26, 109–118 (1986)). For $R_1$, $R_2$, and $R_3$, the ten best scoring components from unique clusters were selected for the directed library.

C. Diverse Library Design

A diverse library, which was set at the same size as the directed library, was prepared to provide a "hit" rate when structure-based methods were not employed. The diverse library was designed to maximize the variety of functional groups and structural motifs of the library components. The sidechains for this library were selected by clustering the original list of components based on their similarity to each other. Components were clustered with the Jarvis-Patrick algorithm (R. A. Jarvis, et al., *IEEE Comput* C22, 1025–1034 (1973)) using the Daylight connectivity measure of similarity (Daylight Clustering Toolkit, Daylight Chemical Information Systems, Inc., Santa Fe, N. Mex.) and a binary Tanimoto metric (P. Willett, *Similarity and Clustering in Chemical Information Systems* (John Wiley & Sons, New York, N.Y., 1987); P. Willett, et al., *J. Chem. If. Comput. Sci.* 26, 109–118 (1986)). In the Jarvis-Patrick method, two compounds are placed in the same cluster if they: 1) are neighbors of one another, and 2) share at least p neighbors from a list of q nearest neighbors, where p and q are adjustable parameters. The compound nearest the cluster centroid was chosen as the cluster representative.

The $R_1$ (amine) components were clustered directly as the primary amines. The $R_2$ and $R_3$ acylating agents were each attached to a portion of the scaffold before clustering to yield the proper chemical context at the linkage site. The first round of clustering yielded 47, 154, and 162 clusters using p/q=4/11, p/q=4/12, and p/q=4/12 for $R_1$, $R_2$, and $R_3$, respectively. The representative $R_2$ and $R_3$ components were clustered a second time (p/q=4/7 for $R_2$ and p/q=4/7 for $R_3$), resulting in 23 $R_2$ and 35 $R_3$ components. It is noted that it is not practical to condense a large number of compounds into an arbitrarily small number of clusters because the cluster membership can become very diverse. Final selection of ten compounds from each list was based upon: size, cost, availability and synthetic feasibility. Additionally, a balance of functional groups for each set of sidechains was sought. A comparison of the directed and diverse libraries (FIGS. 4 and 5) shows the much greater range of functionality spanned in the diverse library.

D. Library Synthesis and Screening

Figure 4A:
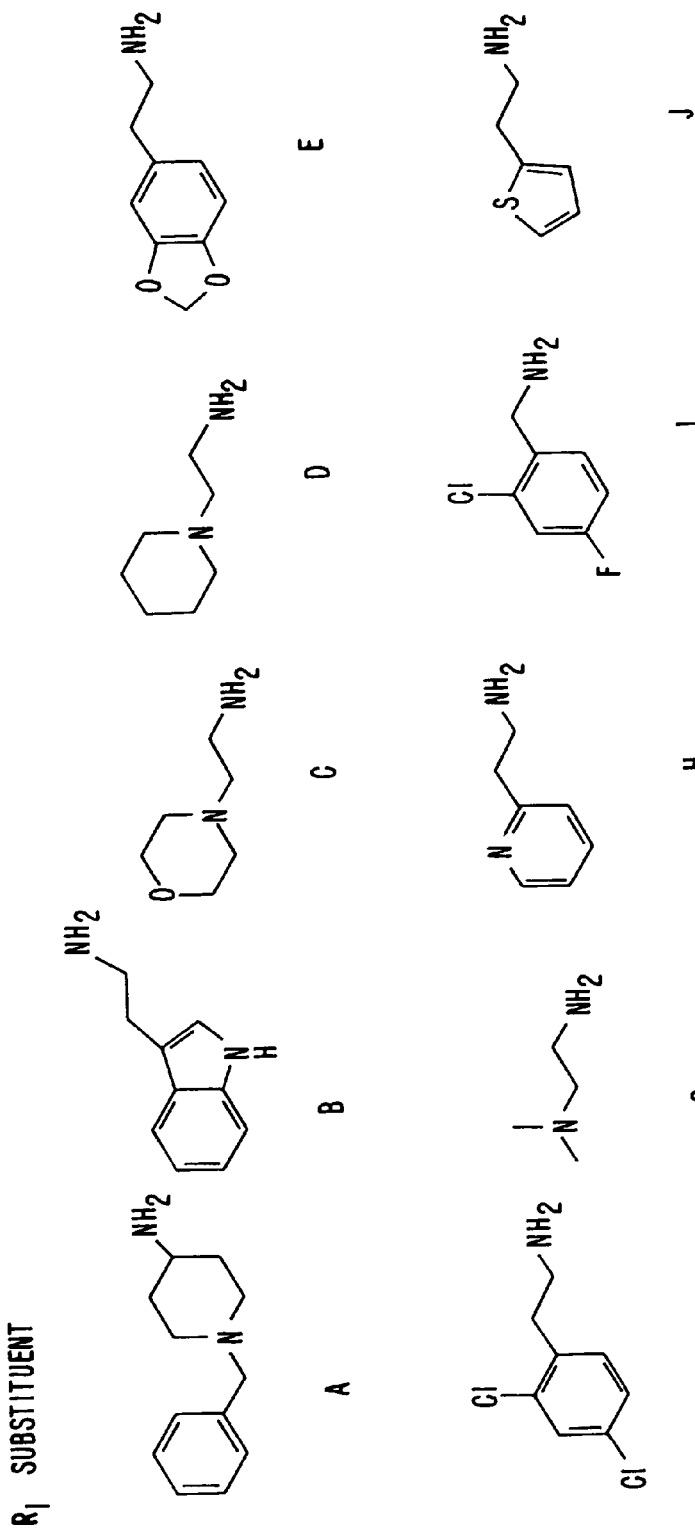
FIGS. 4A–4C illustrate the components used to prepare the Directed Library. Directed library components are labeled with a letter code. EHA is defined as $R_1$=E; $R_2$=H; and $R_3$=A.
Figure 4B:
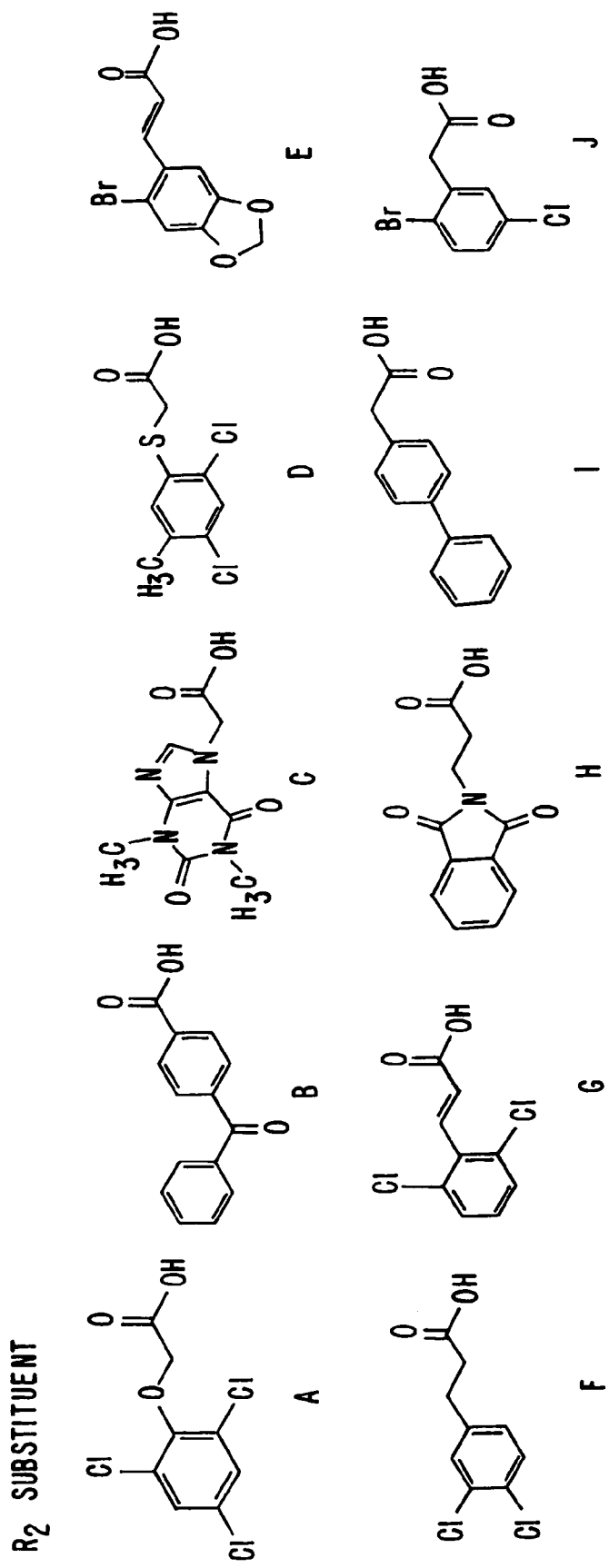
Figure 4C:
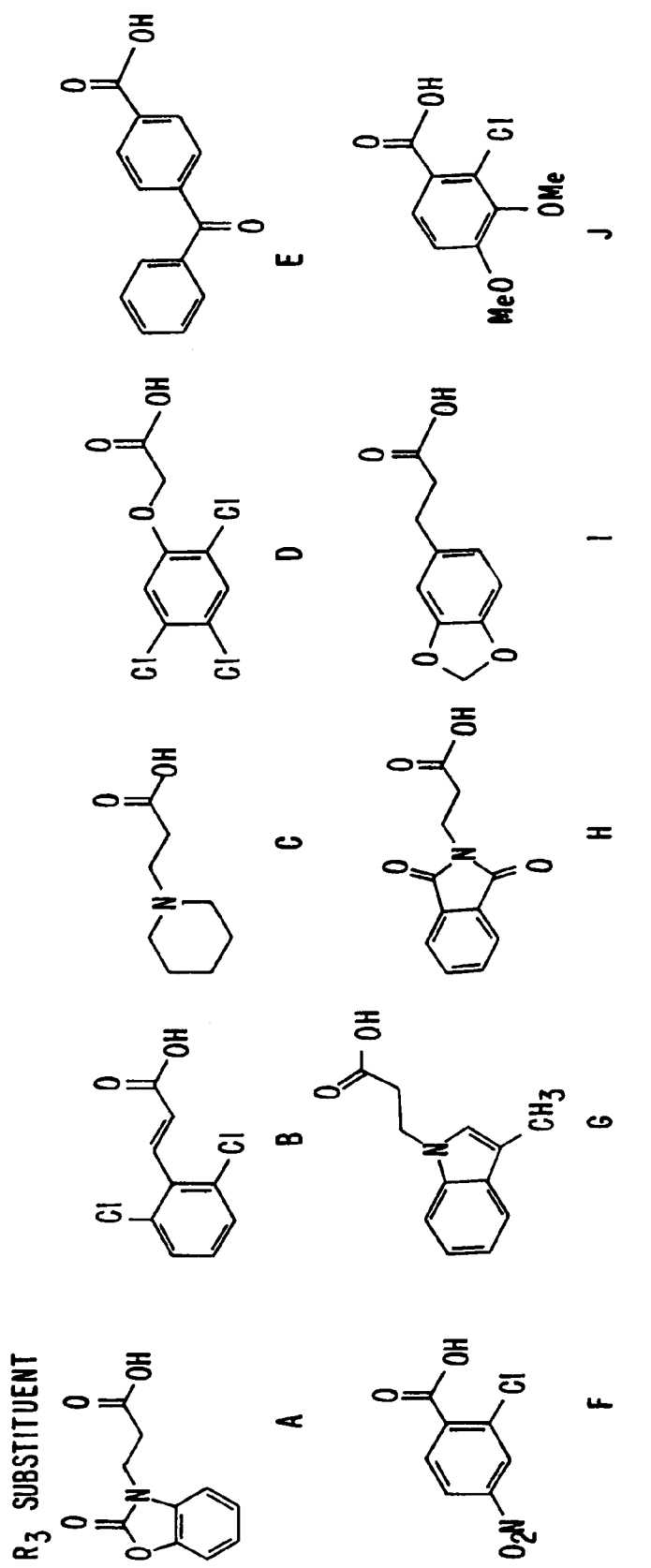
Figure 5A:
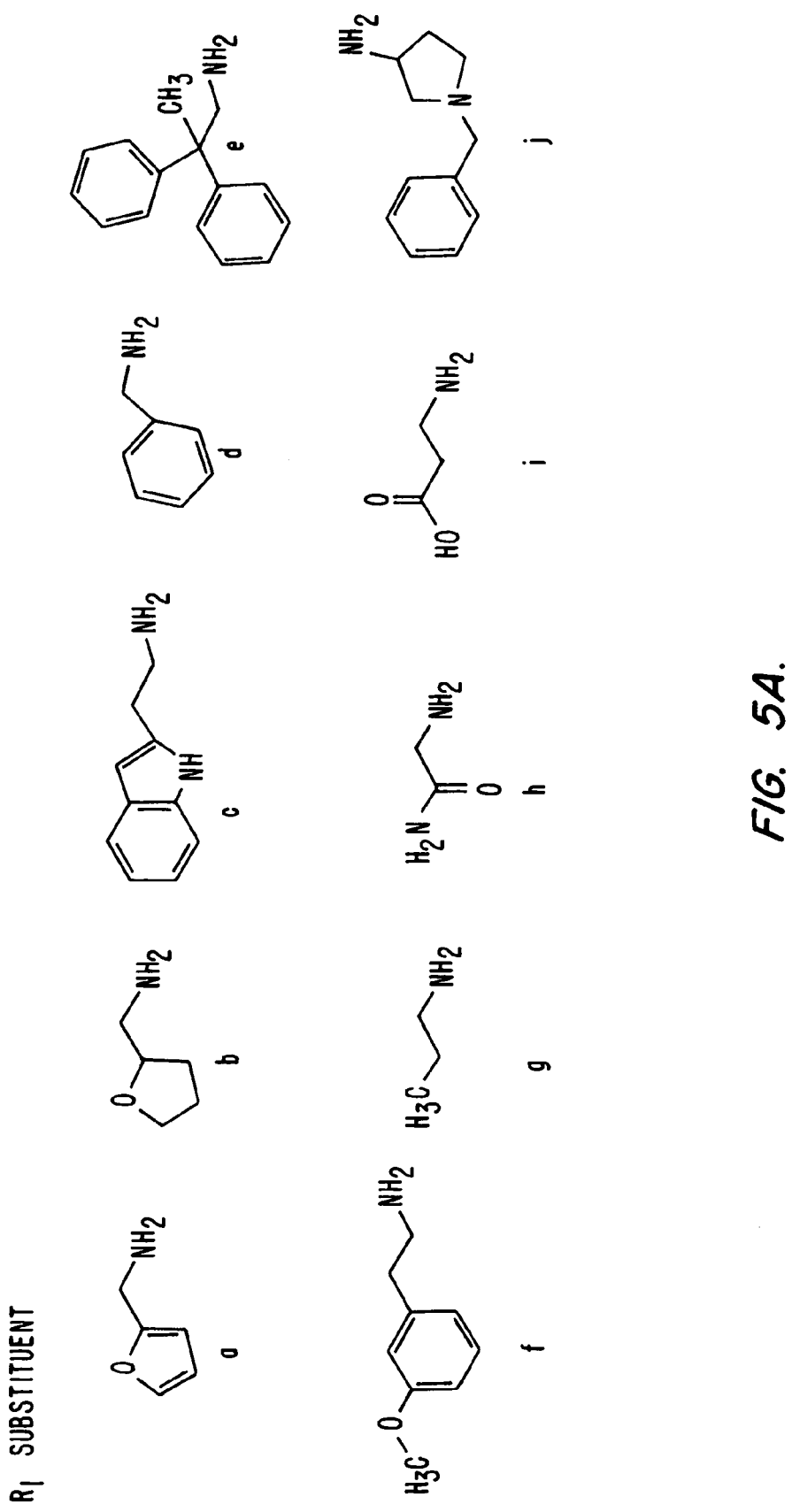
FIGS. 5A–5C illustrates the components used to prepare the Diverse Library. Diverse library components are labeled by lower case letter code as for the directed library.
Figure 5B:
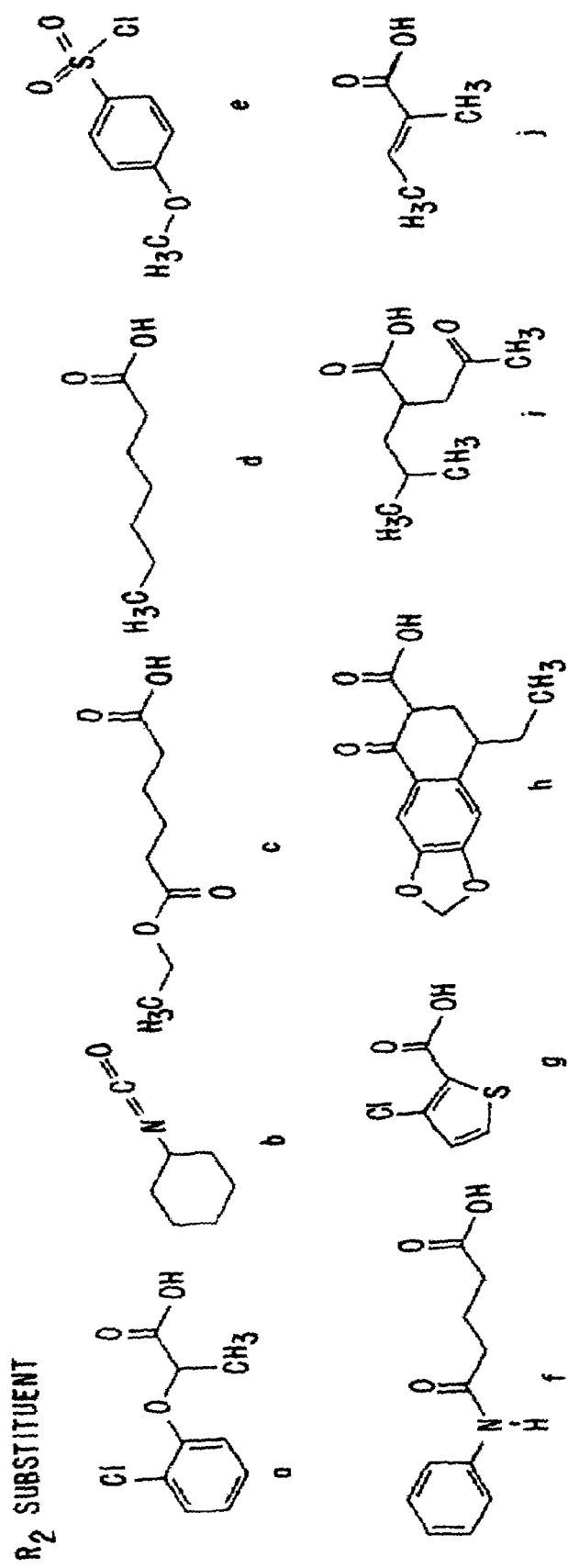
Figure 5C:
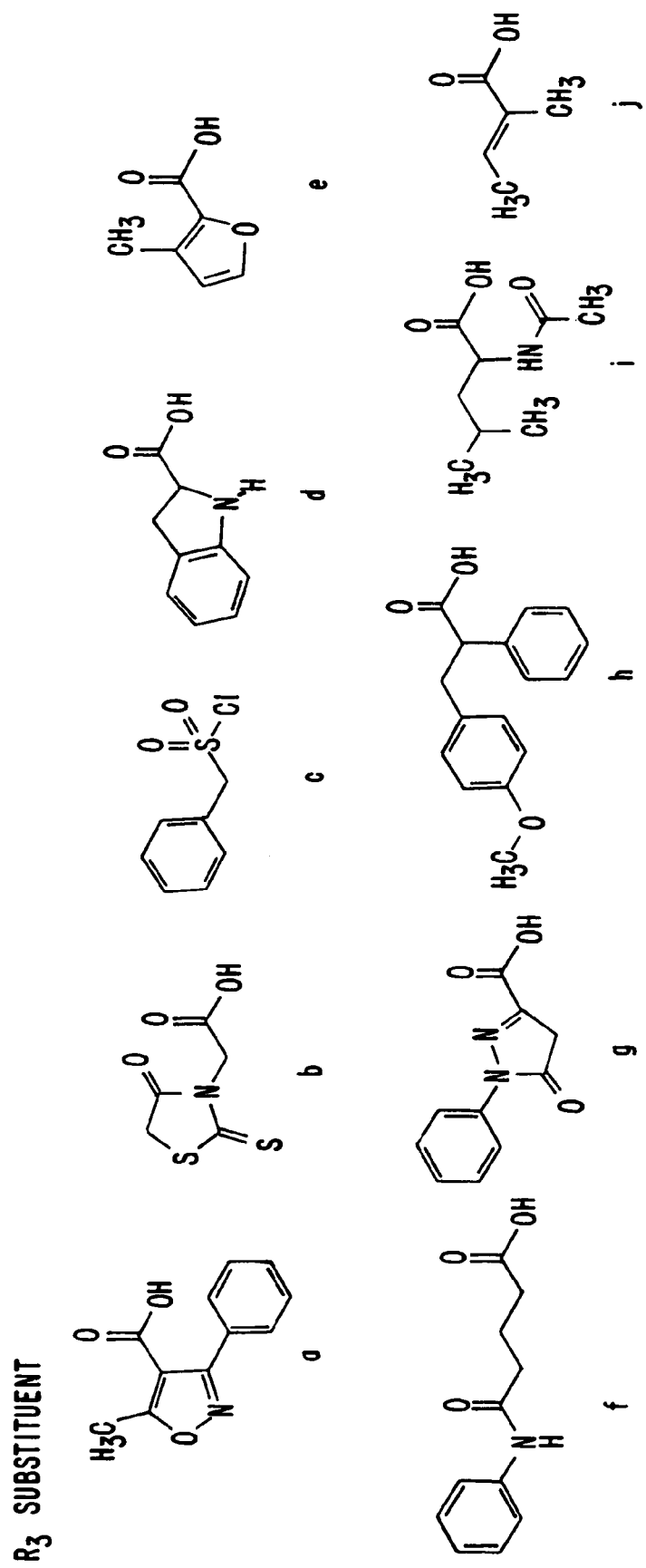
Figure 6A:
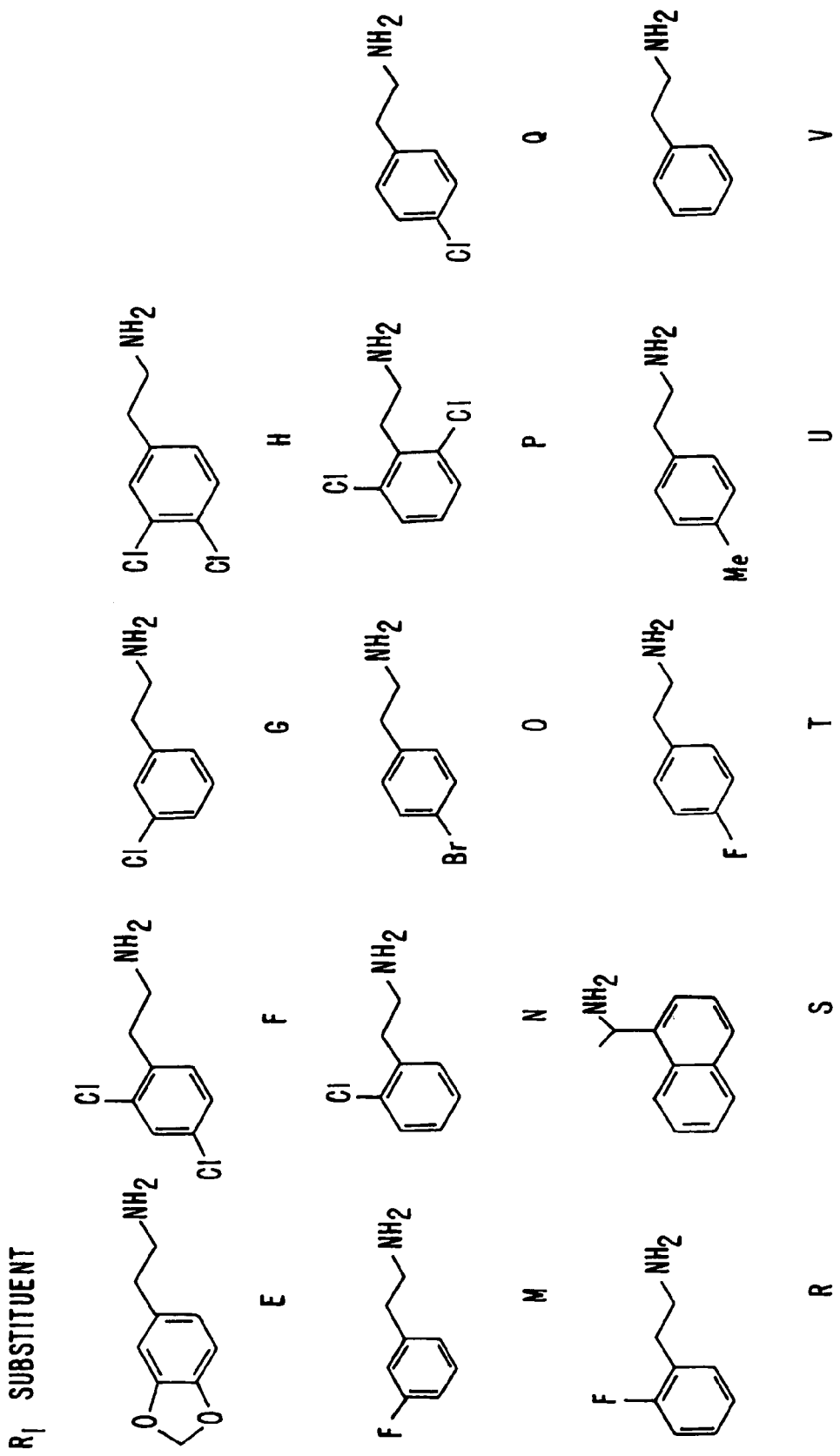
FIGS. 6A–6C illustrates the components in each of the clusters (see Experimental Design) that contained the most active sidechains, $R^1$=E, F; $R^2$=F, H; $R^3$=A, D. J. Thirty-nine compounds incorporating these sidechains were synthesized on resin as described previously, EFD, EHD, FFD, FHD, KFD, KHD, LFD, LHD, MFD, MHD, NFD, NHD, OFD, OHD, PFD, PHD, QFD, QHD, RFD, RHD, SFD, SHD, TFD, THD, UFD, UHD, VFD, VHD, EHA, EHJ, EHK, EHL, EHM, EHN, EHO, EHP, EHQ, EHR, EHS. The compounds were assayed at 333 nM, 100 nM and 33 nM in high-throughput screening. The most active compounds were synthesized on large scale and the $K_i$ values were determined (Table 3).
Figure 6B:
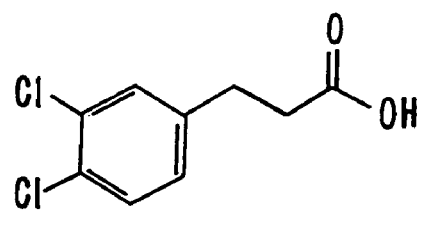
Figure 6B:
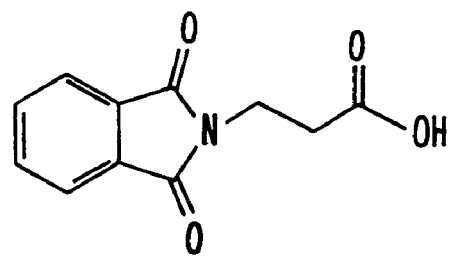
Figure 6C:
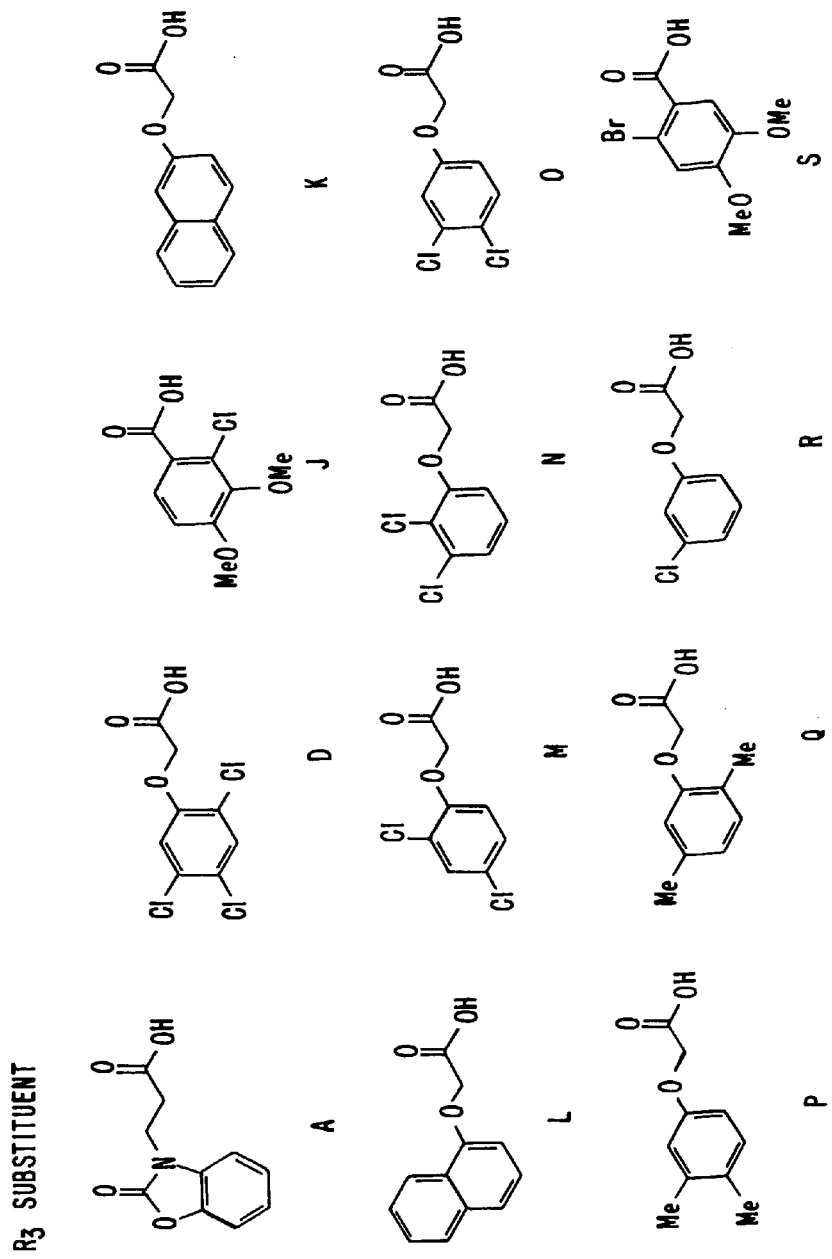

The directed and diverse libraries (1000 compounds each) were prepared using diastereomer 1 of the hydroxyethylamine scaffold with the components used in library syntheses shown in FIGS. 4 and 5, respectively. Because the pilot study with R and S epimers only showed activity at 1 µM inhibitor concentration for the S epimers, only the S epimers of the directed and diverse library were synthesized. All libraries were synthesized in a spatially separate format, and were screened in a high-throughput fluorometric assay for inhibitory activity against cathepsin D (G. A. Krafft, et al., *Methods Enzymol.* 241, 70–86 (1994))

1. Library Synthesis

The optimization of the solid-phase synthesis sequence to prepare the hydroxyethylamine inhibitors and the demonstration of reaction generality was previously reported by E. K. Kick and J. A. Ellman (*J. Med. Chem.* 38, 1427–1430 (1995)). Further testing was performed to establish that the different functionality to be displayed at $R_1$, $R_2$ and $R_3$ would be successfully incorporated into the potential inhibitors. First, all the amines and acylating agents to be incorporated in both the diverse and directed libraries were treated with trifluoroacetic acid for 2 h at room temperature to ensure stability to the support-cleavage conditions, by far the harshest reaction conditions in the synthesis sequence. Second, components that might pose difficulties on chemical or steric grounds were evaluated by trial syntheses. Five amines and four carboxylic acids that did not provide the expected final compound in high yields or purity were discarded. The following amines and acylating agents were successfully tested in the synthesis sequence: $R_1$=B, C, E, F, a, e, h, i, j; $R_2$=B, C, D, E, H, a, e, f; $R_3$=A, D E H, a, b, e, g, h, i (FIGS. 4 and 5). The remaining components were assumed to be compatible with the synthesis sequence.

The library synthesis was performed on polystyrene beads (20–40 mesh). The library was synthesized in a spatially separate array using a 96-well filter apparatus. Transfer of the resin to the individual wells was performed using an isopycnic mixture of N,N-dimethylformamide (DMF) and 1,2-dichloroethane. Incorporation of $R_1$ was carried out using 1.0 M free amine in N-methylpyrrolidinone (NMP) at 80° C. for 36 h. Incorporation of $R_2$ was carried out using stock solutions of 0.3 M carboxylic acid, 0.3 M benzotriazole-1-yl-oxy-tris-pyrrolidino-phosphonium hexafluorophosphate (PyBOP), 0.3 M 7-aza-1-hydroxybenzotriazole (HOAt), and 0.9 M iPr2EtN in NMP overnight. The coupling reactions were performed twice to ensure that complete coupling had occurred. After azide reduction with $SnCl_2$, PhSH and $Et_3N$, incorporation of $R_3$ was carried out as reported above for $R_2$. Carboxylic acid $R_2$=E was coupled using 0-(7-azabenzotriazol-1-yl)-1,1,3,3-tetramethyl-uronium hexafluorophosphate (HATU) instead PyBOP due to formation of a precipitate under the standard coupling procedure. The isocyanate $R_2$=b was coupled at 0.3 M in NMP overnight, and the sulfonyl chlorides $R_2$=e and $R_3$=c were coupled at 0.3 M in NMP that was 0.9 M in $iPr_2EtN$. Cleavage of the material from the support was achieved by subjecting the resin to 95:5 trifluoroacetic acid: $H_2O$ for 30 min. The cleavage mixture was removed from the resin via filtration, followed by rinsing the resin and concentration of the filtrates using a Jouan 10.10 centrifugation concentrator. Toluene was added to form an azeotrope with trifluoroacetic acid during the concentration step. After concentration, the libraries were stored at −20° C.

Compounds from each library, picked by random number generation, were analyzed by mass spectrometry in a matrix of α-cyano cinnamic acid on a Perseptive Biosystems MALDI instrument. For the diverse library the expected molecular ion peaks were observed for 46 of 49 compounds (poor ionization was obtained for the other three). Molecular ion peaks were obtained for 44 of 49 compounds from the directed library. In addition, the synthesis has been validated by the reasonable correlation of the approximate $IC_{50}$ values of the crude material from the libraries with purified material that was synthesized on large scale for a number of compounds (see, Table IV, infra).

2. Screening of the Libraries for Compounds Having Inhibitory Activity Against Cathepsin D Briefly, a fluorometric high through-put assay for activity toward human liver cathepsin D (Calbiochem) was performed in 96-well microtiter plates (G. A. Krafft, et al., Methods Enzymol. 241, 70–86 (1994)). The peptide substrate (Ac-Glu-Glu(Edans)-Lys-Pro-Ile-Cys-Phe-Phe-Arg-Leu-Gly-Lys(Methyl Red)-Glu-$NH_2$) used in the assay has been previously reported ($K_m$=6 μM) (E. T. Baldwin, et al., Proc. Natl. Acad. Sci., U.S.A. 90, 6796–6800 (1993)). The assay was performed in DYNATECH Microfluor fluorescence microtiter plates, and readings were taken on a Perkin-Elmer LS-50B with an attached 96-well plate reader. The excitation wavelength was 340 nm. A 340 nm interference filter (Hoya, U-340) for excitation and a 430 nm cut-off filter for emission were used. For the microtiter-based assays, the substrate concentration was 5 μM and the cathepsin D concentration was 9 nM in a 0.1 M formic acid buffer (pH=3.7). DMSO (10%) was used to ensure complete dissolution of the inhibitors. The fluorescent unit readings were taken at three time points within the linear region of the substrate cleavage, and percent activity of the enzyme was determined by comparing the change of fluorescent units (FU) for each well to the average change in FU for six control wells without inhibitor. Each library was screened at approximately 1 μM inhibitor with the concentration based on the assumption that 50% of the theoretical yield was obtained for each inhibitor. All wells that showed<50% cathepsin D activity were screened at subsequent three-fold dilutions. All active compounds that showed<60% enzyme activity in 1 μM or lower inhibitor concentrations were assayed in duplicate).

E. Assay Results

At approximately 1 μM of crude compound, the directed library yielded 67 compounds that inhibited cathepsin D activity≧50%(G. A. Krafft, et al., Methods Enzymol. 241, 70–86 (1994)). Further dilution of 333 nM and 100 nM inhibitor concentrations afforded 23 and 7 compounds, respectively, that inhibited cathepsin D activity≧50% (see, Table III). The data for the diverse library are also in Table III, infra. There are many uncertainties that can influence the results of a high-throughput fluorescence assay, including the purity of each compound, the concentration of the compounds, and the experimental errors associated with the microtiter fluorescence assay. From repetitive experiments, these errors were estimated to be approximately 30%, expressed as enzyme activity.

TABLE III

Number of Compounds with ≧ 50% Inhibition of Cathepsin D in Library Screen[a]

| [Inhibitor] | Library | |
|---|---|---|
| | Directed | Diverse# |
| 100 nM | 7* | 1§ |
| 330 nM | 23† | 3¶ |
| 1 μM | 67 | 26 |
| 10 μM | 11/95‡ | |

[a]Inhibitors of cathepsin D at respective concentrations:
*EAA, EFA, EHA, EHD, EHI, EHJ, FHA. An additional six compounds provided 40–50% inhibition of cathepsin D.
†EAA, EFA, EHA, FAA, FFA, FHA, EHB, EFD, EHD, EEF, EHF, FHF, EFH, EHH, FAH, FFH, EFI, EHI, EAJ, EFJ, EGJ, EHJ, FHJ. An additional thirty compounds provided 40–50% inhibition of cathepsin D.
‡One hundred compounds were selected by random number generation for testing at 10 μM. Five compounds were highly fluorescent at these concentrations, so that accurate assay data could not be obtained in these cases.
§fbb,
¶fba, fbb, fcb. Four compounds (fca, fdb, fib, hhb) provided 40–50% inhibition of cathepsin D; with the experimental error in the assay, this activity is similar to the activity for the three that are listed.
The diverse library was not tested at 10 μM.

In order to obtain accurate inhibition constants ($K_i$) several of the compounds most likely to be potent inhibitors based on the library screening were synthesized on a larger scale, purified by chromatography, and characterized by NMR and mass spectrometry. The $K_i$ values were calculated from $IC_{50}$ determinations (see, Table IV). From the compounds that were fully characterized, one compound was obtained from the directed library with a $K_i$ below 100 mM, whereas the diverse library contained inhibitors that were 3–4 times less potent.

TABLE IV

Inhibition Constants for a Number of the Compounds That Are Potent Inhibitors[a]

| Cpd Code | Scaffold | $K_i$(nM) |
|---|---|---|
| EHD | 1 | 73 ± 9 |
| EHD | 2 | >5000 |
| EHJ | 1 | 111 ± 8 |
| EHA | 1 | 131 ± 12 |
| EFA | 1 | 171 ± 25 |
| FHA | 1 | 231 ± 31 |
| fbb | 1 | 356 ± 31 |
| fdb | 1 | 595 ± 66 |

TABLE IV-continued

Inhibition Constants for a Number of the Compounds That Are Potent Inhibitors[a]

| Cpd Code | Scaffold | $K_i$(nM) |
| --- | --- | --- |

[a]The cathepsin D assay for "hits" from the directed and diverse libraries was performed in a quartz cuvette with a Perkin-Elmer LS-50B spectrometer. The substrate concentration was 2.5 µM and the cathepsin D concentration was 10 nM. Inhibition constants ($K_i$) were determined from $IC_{50}$ values taken from plots of $V_i/V_0$ versus inhibitor concentration, where $V_0$ is the velocity in absence of the inhibitor and $V_i$ is thevelocity with inhibitor. Since $IC_{50}$ values were converted to $K_i$ by the equation $K_i \approx (IC_{50} - E_t/2)$, where $E_t$ = enzyme concentration (S. Cha, et al., Biochem. Pharmacol., 24, 2187–2197 (1975)).

F. (i) Second Generation Library

In the design of the directed library, derivatives with a high level of structural similarity were selected against by applying a clustering algorithm to the highest scoring components (see Directed Library Design). These clusters were re-examined to explore the important structural elements of the most active compounds from the directed library. In particular, a small second generation library from the clusters for the $R_1$, $R_2$ and $R_3$ positions that provided the most active compounds was synthesized and screened (see, FIG. 6). At 1 µM, 92% of the compounds screened inhibited cathepsin D $\geq$50%, and 18% of the compounds at 100 nM inhibited cathepsin D$\geq$50%. Inhibition constants were determined for selected compounds (see, Table V), providing several potent inhibitors ($K_i \leq$15 nM) of cathepsin D.

TABLE V

Second Generation Assay (see, FIG. 6)[a]

| Cpd. Code | Scaffold | $IC_{50}$ (nM) | $K_i$(nM) |
| --- | --- | --- | --- |
| EHO | 1 | 19 ± 2 | 15 |
| EHO | 2 | >5000 | |
| FHO | 1 | 18 ± 2 | 14 |
| EHM | 1 | 14 ± 2 | 9 |
| EHR | 1 | 20 ± 2 | 15 |
| EHS | 1 | 64 ± 6 | 59 |
| UHD | 1 | 229 ± 44 | 224 |

[a]Assay conditions are reported in Table IV.

F. (ii) Additional Compounds

Known aspartyl protease inhibitors have both (R) and (S) stereocenters about the hydroxyl group in Formula I. Employing α-alkoxy chelation and non-chelation controlled reductions, the following synthetic strategy demonstrates acyclic diastereocontrol on solid support providing access to either desired diastereomer. By exploring different functional groups for $R_5$ and $R_6$ and selecting the $R_1$, $R_2$, and $R_3$ substituents providing the most potent Cathepsin D inhibitors, additional low nanomolar Cathepsin D inhibitors were discovered.

Figure 7:
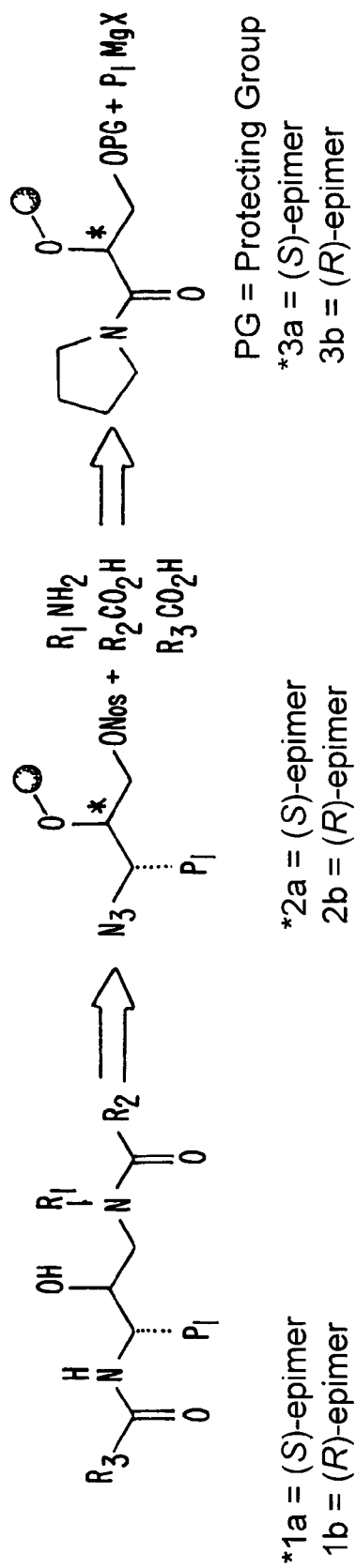
FIG. 7 illustrates structural diversity being introduced via Grignard addition to solid support-bound α-alkoxy pyrrolidine amide.

Structural diversity may be derived through Grignard addition to a solid support-bound α-alkoxy pyrrolidine amide 3 (see, FIG. 7). The source of diversity is derived from aromatic and alkyl Grignard reagents. The Grignard reagents that are not commercially available can be synthesized using activated magnesium turnings, or a magnesium anthracene THF complex and the corresponding aromatic and alkyl halides. Grignard reagents are a suitable source to introduce diversity in the $P_1$ site of potential aspartyl protease inhibitors, since the $S_1$ protease surface tends to be hydrophobic. The resulting ketone is reduced using chelation and non-chelation conditions to provide the desired diastereomer. After several functional group manipulations, known azido-nosylate intermediate 2 is derived and carried through the previously reported synthesis to obtain potential aspartyl protease inhibitor 1 (see E. K. Kick, J. A. Ellman, J. Med. Chem. 38, 1427–1430 (1995)) (see, FIG. 7).

The pyrrolidine amide 4 prepared in 3 steps in an overall 76% yield from commercially available methyl (s)-(-)-2,2-dimethyl-1,3-dioxolane-4-carboxylate, was coupled to benzyloxybenzyl bromide resin 5 using sodium hydride, tetrabutylammonium iodide, and catalytic 18-Crown-6 in THF for 2 hours at 45° C. (see, FIG. 8). Bromide resin 5 was derived from carbon tetrabromide, triphenylphosphine, and commercially available Wang resin.

Figure 8:
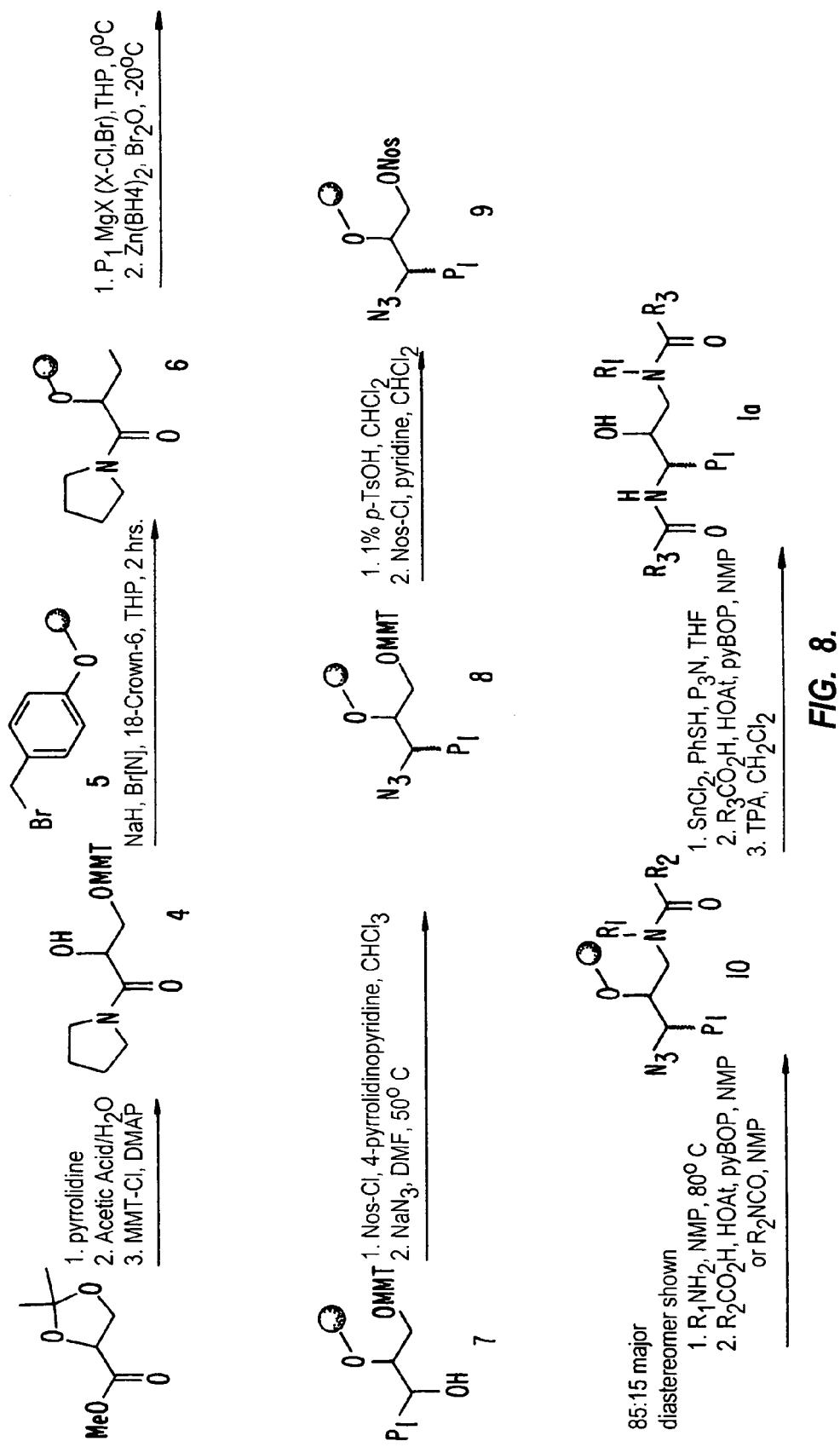
FIG. 8 illustrates synthesis of solid phase aspartyl protease inhibitor synthesis.

Grignard addition in THF at 0° C. to support-bound pyrrolidine amide 6 followed by α-alkoxy chelation controlled reduction of the resulting ketone using zinc borohydride in diethyl ether at −20° C. afforded secondary alcohol 7 in a 85:15 diastereomeric mixture with the major diastereomer shown (see, FIG. 8). A small portion of secondary alcohol 7 was cleaved from the support to provide the corresponding triol product which was converted to the corresponding triacetate using acetic anhydride and DMAP (Dimethyl amino pyridine). Diastereoselectivity was determined from GC analysis of the corresponding triacetates. No over alkylation from the Grignard addition was detected for all components used in the library.

Secondary alcohol 7 was converted to azide 8 through the formation of a secondary nosylate using 4-nitrobenzenesulfonyl chloride and 4-pyrrolidinopyridine in chloroform followed by azide displacement with sodium azide in N,N-dimethylformamide at 50° C. The p-methoxy trityl protecting group was selectively removed using 1% p-toluenesulfonic acid in methylene chloride. Nosylation of the primary alcohol with 4-nitrobenzenesulfonyl chloride and pyridine in chloroform provided azido-nosylate 9.

Amine displacement in N-methylpyrrolidinone (NMP) at 80° C. followed by acylation with the desired carboxylic acid, benzotriazole-1-yl-oxy-tris-pyrrolidino-phosphonium hexafluorophosphate (PyBOP), aza-1-hydroxybenzotriazole (HOAt) or isocyanate in NMP afforded intermediate 10 with the $P_1$, $R_1$, and $R_2$ sites of diversity in place. Reduction of the azide with tin(II) chloride, thiophenol, and triethylamine followed by acylation with the $R_3$ carboxylic acid, PyBOP, and HOAt, and lastly, cleavage from the support using a trifluoroacetic acid:methylene chloride (90:10) mixture provided the desired potential aspartyl protease inhibitor 1a.

Figure 9:
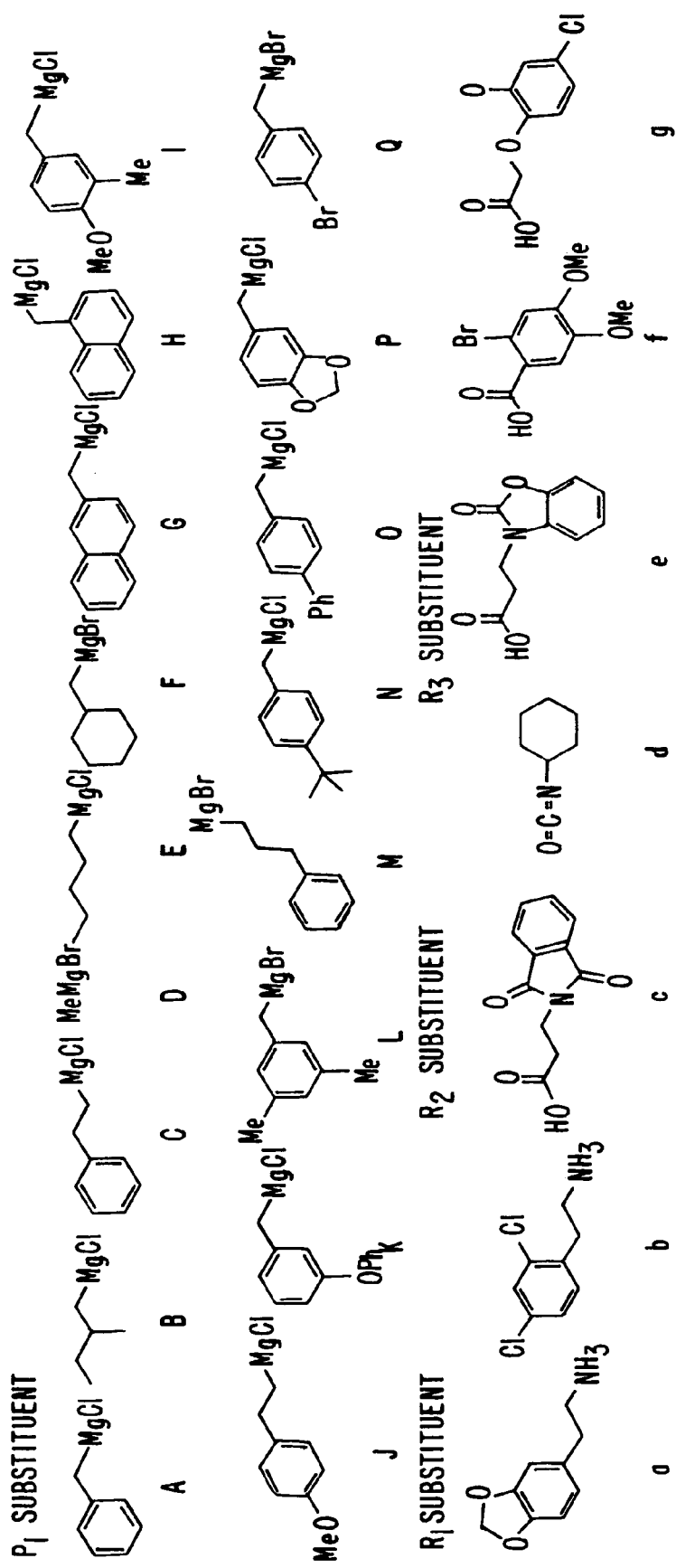
FIG. 9 illustrates components to generate library diversity in a 204 compound library. ////

A library of 204 compounds was derived from the components in FIG. 9. The most potent inhibitors of Cathepsin D were synthesized on a larger scale, purified, and biologically assayed to determine $K_i$ values as detailed in Table VI. Overall yields of these scaled-up inhibitors ranged from 46–48% for the entire 12 step solid-phase synthesis as determined by the mass balance of desired product after column chromatography purification.

TABLE VI

Inhibition constants for selected compounds ($K_i$)

| Inhibitor | Code ($P_1 R_1 R_2 R_3$) | $K_i$ (nM) | Overall Yield (12 steps) |
|---|---|---|---|
| *(structure with 3-phenoxybenzyl P1 group)* | Kbcf | 1.9 ± 0.2 | 46% |
| *(structure with 2-naphthylmethyl P1 group)* | Gbcf | 2.6 ± 0.2 | 48% |
| *(structure with 4-biphenylmethyl P1 group)* | Obcf | 2.6 ± 0.2 | 48% |

TABLE VI-continued

Inhibition constants for selected compounds ($K_i$)

| Inhibitor | Code ($P_1 R_1 R_2 R_3$) | $K_i$ (nM) | Overall Yield (12 steps) |
|---|---|---|---|
| 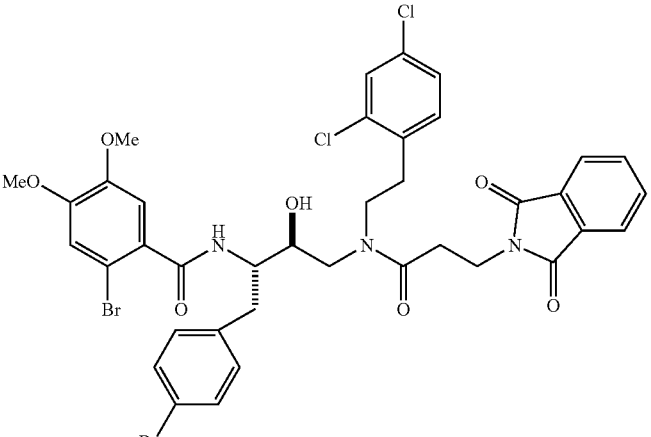 | Qbcf | 6.7 ± 0.7 | 46% |

Synthesis of Inhibitors

Several of the most potent compounds were synthesized on an average of 115 milligram scale on the solid support following the aforementioned method. These compounds were purified by column chromatography and characterized by $^1$H NMR and elemental analysis. Overall yields of the compounds were based on the entire 12 step solid-phase synthesis and determined by the mass balance of desired product after column chromatography purification. The characterization data are listed with the corresponding compound code. The $^1$H NMR data is reported for the major amide rotomer of the major diastereomer for each compound.

Kbcf. (57 mg, 46%) $^1$H NMR (400 MHz, CDCl$_3$) d 2.65 (m, 2H), 2.88 (apparent t, J=7.7, 2H), 3.01 (apparent t, J=6.9, 2H), 3.24 (m, 1H), 3.47 (m, 2H), 3.83–3.96 (m, 4H), 3.85 (s, 3H), 3.89 (s, 3H), 4.34 (apparent q, J=8.3, 1H), 4.66 (br. s, 1H), 6.71 (d, J=9.2, 1H), 6.84 (dd, J=1.7, 8.0, 1H), 6.93–7.00 (m, 5H), 7.05 (m, 1H), 7.05 (s, 1H), 7.07 (s, 1H), 7.16 (dd, J=2.1, 8.1, 1H), 7.23–7.30 (m, 3H), 7.34 (d, J=2.1, 1H), 7.71 (dd, J=3.1, 5.4, 2H), 7.83 (dd, J=3.1, 5.4, 2H). Anal. calc'd for $C_{44}H_{40}N_3O_8Cl_2Br_1$: C, 59.41; H, 4.53; N, 4.72. Found: C, 59.22; H, 4.76; N, 4.52.

Gbcf. (48 mg, 48%) $^1$H NMR (400 MHz, CDCl$_3$) d 2.62 (apparent t, J=7.5, 2H), 2.82 (apparent t, J=7.6, 2H), 3.18–3.25 (m, 3H), 3.40–3.47 (m, 2H), 3.57 (s, 3H) 3.85 (s, 3H), 3.91–3.96 (m, 4H), 4.47 (apparent q, J=8.4, 1H), 4.76 (br. s, 1H), 6.69 (s, 1H), 6.92 (d, J=8.2, 1H), 6.95 (s, 1H), 7.04 (dd, J=2.1, 8.2, 1H), 7.29 (d, J=2.1, 1H), 7.40–7.45 (m, 3H), 7.68 (dd, J=3.0, 5.5, 2H), 7.71–7.80 (m, 6H). Anal. calc'd for $C_{42}H_{38}N_3O_7Cl_2Br_1$: C, 59.52; H, 4.52; N, 4.96. Found: C, 59.63; H, 4.67; N, 4.69.

Obcf. (55 mg, 48%) $^1$H NMR (400 MHz, CDCl$_3$) d 2.65 (m, 2H), 2.85 (apparent t, J=7.3, 2H), 3.08 (apparent t, J=6.7, 2H), 3.23 (m, 1H), 3.44 (m, 1H), 3.57 (m, 1H), 3.75 (s, 3H), 3.86 (s, 3H), 3.94 (m, 4H), 4.39 (apparent q, J=8.3, 1H), 4.73 (br. s, 1H), 6.78 (d, J=9.2, 1H), 6.93 (s, 1H), 6.97 (s, 1H), 7.02 (d, J=8.2, 1H), 7.10 (dd, J=2.1, 8.2, 1H), 7.30 (d, J=2.1, 1H), 7.36–7.42 (m, 5H), 7.51–7.54 (m, 4H), 7.68 (dd, J=3.0, 5.4, 2H), 7.81 (dd, J=3.0, 5.4, 2H). Anal. calc'd for $C_{44}H_{40}N_3O_7Cl_2Br_1$: C, 60.49; H, 4.62; N, 4.81. Found: C, 60.23; H, 4.86; N, 4.58.

Qbcf. (55 mg, 46%) $^1$H NMR (400 MHz, CDCl$_3$) d 2.64 (m, 2H), 2.86 (apparent t, J=7.1, 2H), 2.96 (m, 2H), 3.20 (m, 1H), 3.46 (m, 1H), 3.54 (m, 1H), 3.78 (m, 2H), 3.82 (s, 3H), 3.86 (s, 3H), 3.91 (m, 2H), 4.31 (apparent q, J=8.5, 1H), 4.73 (br. s, 1H), 6.73 (d, J=9.3, 1H), 6.85 (s, 1H), 6.96 (s, 1H), 7.03 (d, J=8.3, 1H), 7.14 (m, 2H), 7.16 (dd, J=2.2, 8.3, 1H), 7.32 (d, J=2.2, 1H), 7.37–7.41 (m, 2H), 7.70 (dd, J=3.0, 5.5, 2H), 7.80 (dd, J=3.0, 5.5, 2H). Anal. calc'd for $C_{38}H_{35}N_3O_7Cl_2Br_2$: C, 52.08; H, 4.03; N, 4.79. Found: C, 52.28; H, 4.09; N, 4.60.

G. Results

Novel low nanomolar inhibitors of cathepsin D were identified rapidly using combinatorial chemistry coupled with two different computational strategies. The diverse and directed libraries together yielded over 90 compounds active at 1 μM and 26 active in the submicromolar range. The "hit rate" for activity at 1 μM is 6–7% for the directed library and 2–3% for the diverse library. Even though both the directed and diverse libraries are based on the "active" epimer of the scaffold, the results from the directed library are clearly superior. At all concentrations ≦ 1 μM, there were more "hits" in the directed library than the diverse library. The most potent inhibitors from the directed library are 3–4 fold better than those in the diverse library. It is clear from the results that the number and quality of the active compounds can be increased by using relevant information about the target.

A strength of the structure-based procedure is that it leads directly to testable geometrical hypotheses. In this study there are three hypotheses: 1) S epimers are predicted to bind better than the R epimers; 2) there are two energetically reasonable scaffold conformations (family 1+2, family 3+4), which place R groups into different pockets; 3) all the inhibitors are assumed to bind in approximately the same orientation as pepstatin.

The first hypothesis was directly tested in pilot experiments where no inhibitors based upon the R epimer had activity at 1 µM. In addition, the R epimer of one of the most potent compounds had a $K_i$ no better than 5 µM while the $K_i$ of the S epimer was 15 nM (see, Table V). This conclusion and the inhibitor orientations in the cathepsin D complex will be examined crystallographically.

Using the methodology described herein, active compounds can be identified and then the activity is optimized. The optimization criteria can include improved potency, selectivity, pharmacokinetic properties, or reduced toxicity. Each of these issues appears amenable to library design. For example, compounds with five-six fold improved potencies were rapidly identified by synthesizing and screening a small second generation library that explored variants of the most active compounds.

The success of the directed library in finding potent inhibitors demonstrates the power of coupling combinatorial libraries with structure-based design. Combinatorial libraries allow a larger area of molecular space to be explored with the functionality selected by the structure-based design, removing the need to identify in advance a single "best" target. Similarly, computational methods allow rapid examination of extremely large virtual regimes>$10^{10}$ compounds) and focus the chemical efforts into productive regimes.

It addition to the above methods, additional methods for synthesizing the aspartyl protease inhibitors of the present invention are disclosed in U.S. patent application Ser. No. 60/079,769, entitled "Nanomolar, Non-Peptide Inhibitors of Plasmepsin," filed on Mar. 27, 1998, the teachings of which are incorporated herein by reference.

II. Example II

A. Assays

1. Preparation and Maintenance of Entorhinohippocampal Slice Cultures

Organotypic entorhinohippocampal cultures were prepared using the technique of Stoppini, et al., *J. Neurosci. Methods*, 37, 173–182 (1991). Briefly, the caudal pole of the cerebral hemisphere containing the entorhinal cortex and hippocampus were harvested from brains of 6–7 days old Sprague-Dawley rat pups under sterile condition. 400 µm horizontal entorhinohippocampal sections cut vertical to the long axes of hippocampus were obtained using a McIlwain tissue chopper in a cutting medium consisting of MEM (with Earle's salts, Gibco), 25 mM HEPES, 10 mM Tris Base, 10 mM Glucose, and 3 mM $MgCl_2$ (pH 7.2). Brain tissue explants were then planted onto 30 mm cell culture inserts (Illicell-CM, Millipore, Bedford, Mass.) that were placed in 6 well culture trays with 1 mL of growth medium (MEM with Hank's salts, Gibco, 20% horse serum, 3 mM glutamine, 25 mM HEPES, 5 mM $NaHCO_3$, 25 mM glucose, 0.5 mM ascorbate, 2 mM $CaCl_2$, 2.5 mM $MgCl_2$, 0.5 mg/L insulin, and penicillin, pH 7.2; Bi, et al., *J. Comp. Neuro.*, 401, 382–394 (1998). The cultures were incubated at 35° C. with a 5% $CO_2$-enriched atmosphere and fed every other day until use.

After 10–14 days in vitro, organotypic cultures were incubated with growth medium containing either 20 µM N-CBZ-L-phenylalanyl-L-alanine-diazomethylketone (ZPAD; BACHEM Bioscience, Torrance, Calif.), a selective inhibitor of cathepsins B and L (Shaw and Dean, 1980), in 0.01% DMSO, 20 µM chloroquine (Sigma) or vehicle alone for days as specified. To test the effect of EA-1 on the generation of hyperphosphorylated tau fragments found in neurofibrillary tangles in Alzheimer's disease and other tau pathology-related diseases, 1 µM of EA-1 or 10 µM of CEL5-172 were applied alone or together with 20 µM ZPAD.

2. Immunoblotting

For western blot, entorhinohippocampal explants were collected and sonicated in 10 mM Tris-HCl buffer (pH 7.4) containing 0.32 M sucrose, 2 mM EDTA, 2 mM EGTA, and 0.1 mM leupeptin. Aliquots of homogenate (80–100 µg protein/lane) were diluted with equal amounts of 2×sample buffer [1× sample buffer consists of 2% sodium dodecyl sulphate (SDS), 50 mM Tris-HCl (pH 6.8), 10% 2-mercaptoethanol, 10% glycerol and 0.1% Bromophenol Blue]. After heating to 90–100° C. for 5 min, proteins were subjected to SDS-PAGE performed according to the method of Laemmli (1970) using 10% polyacrylamide gel; and then transferred on to nitrocellulose membranes as described by Towbin, et al., *Proc. Natl. Acad. Sci. USA*, 76, 4350–4354 (1979). Nitrocellulose membranes were first incubated in 3% gelatin in Tris-buffered saline (TBS) for 1 hour at room temperature, followed by incubation with 1% gelatin in TBS with 0.5% Tween 20 (TTBS) containing antibodies that recognize either the phosphorylated tau protein (AT8; 1:500) or unphosphorylated tau protein (tau 1, PC1 C6; 1:100, Boehringer Mannheim) at room temperature overnight. After two washes with TTBS for 5 min, membranes were incubated with alkaline phosphatase conjugated anti-mouse IgG (1:3000; BioRad) for 2 hr at RT, then visualized with solution containing nitroblue tetrazolium and 5-brom-4-chlor-3-indolyl-phosphate toluidine salt (BioRad) in DMF according to the manufacturer's instruction. Immunoblots were scanned, and the digitized images were quantitatively analyzed by densitometry using the NIH Image analysis system program.

B. Results

1. Effect of CEL5-172

Figure 10:
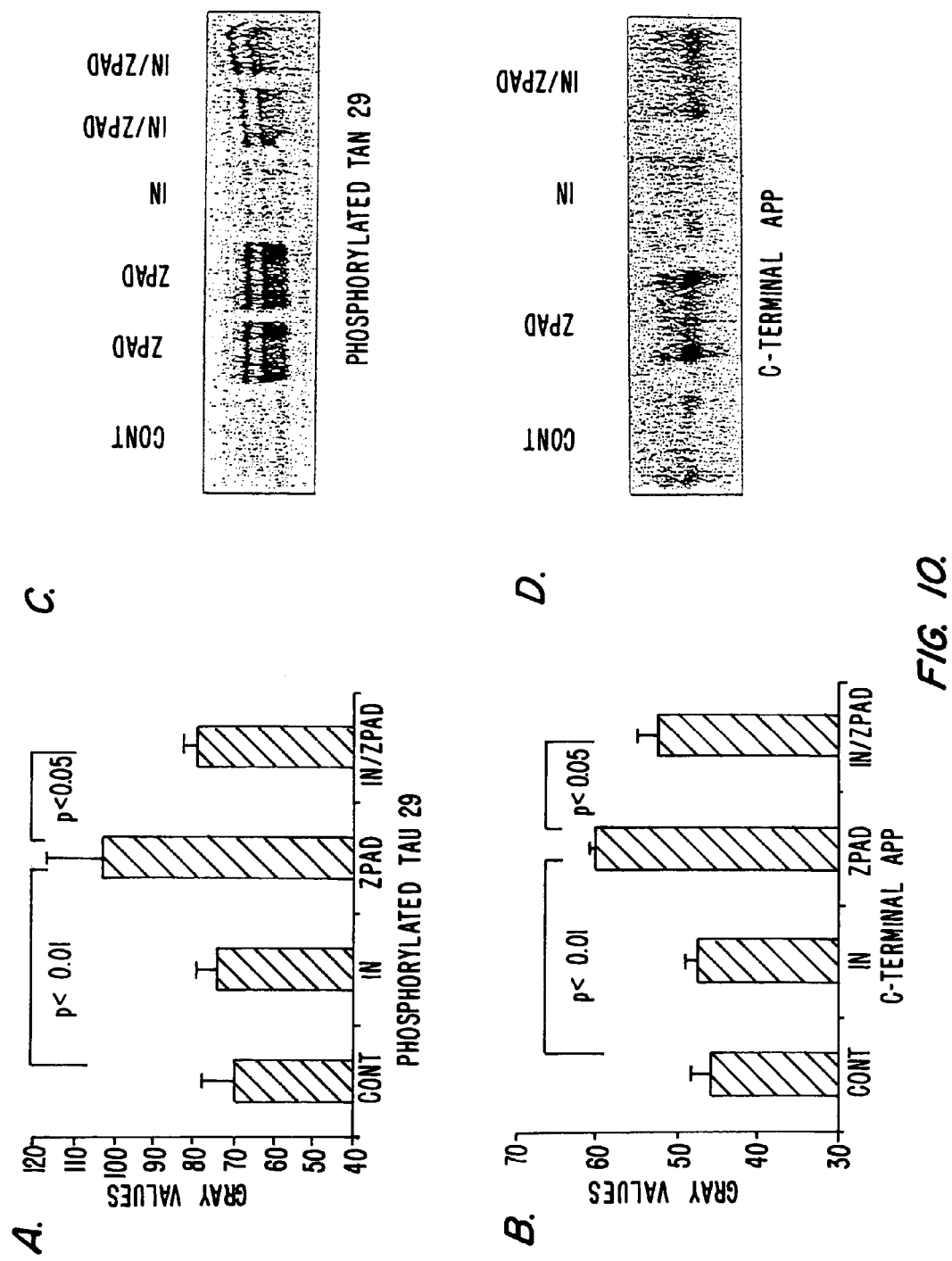
FIG. 10 illustrates that the cathepsin D inhibitor, i.e., CEL5-172, by itself, did not detectably change the concentration of either the tau fragment or the APP fragment, but it did block most, if not all, of the increases in the tau and APP fragments produced by ZDAP.

Four groups of cultured entorhinohippocampal slices were maintained for 14 days and then exposed to one of the following treatments for six additional days: (1) control medium; (2) a selective inhibitor ('ZPAD' at 20 µM) of cathepsins B and L; (3) a selective inhibitor ('CEL5-172' at 10 µM) of cathepsin D; (4) ZPAD combined with CEL5-172. Following this, the slices were homogenized and samples processed for immunoblotting. Antibodies against phosphorylated tau or the carboxyterminal region of the amyloid precursor protein (anti-C $APP_{643-695}$) were used. Previous studies showed that ZPAD alone increases the concentrations of a 27 kDa phosphorylated tau fragment and a 29 kDa APP fragment. Both results were confirmed as shown in the accompanying figure. The cathepsin D inhibitor by itself did not detectably change the concentrations of either antigen (see, FIG. 10). It did, however, block most, if not all, of the increases in tau and APP fragments produced by ZPAD; densiometric values for the combined treatment were close to control values and clearly reduced from those for ZPAD alone.

2. Effect of EA-1

Figure 11:
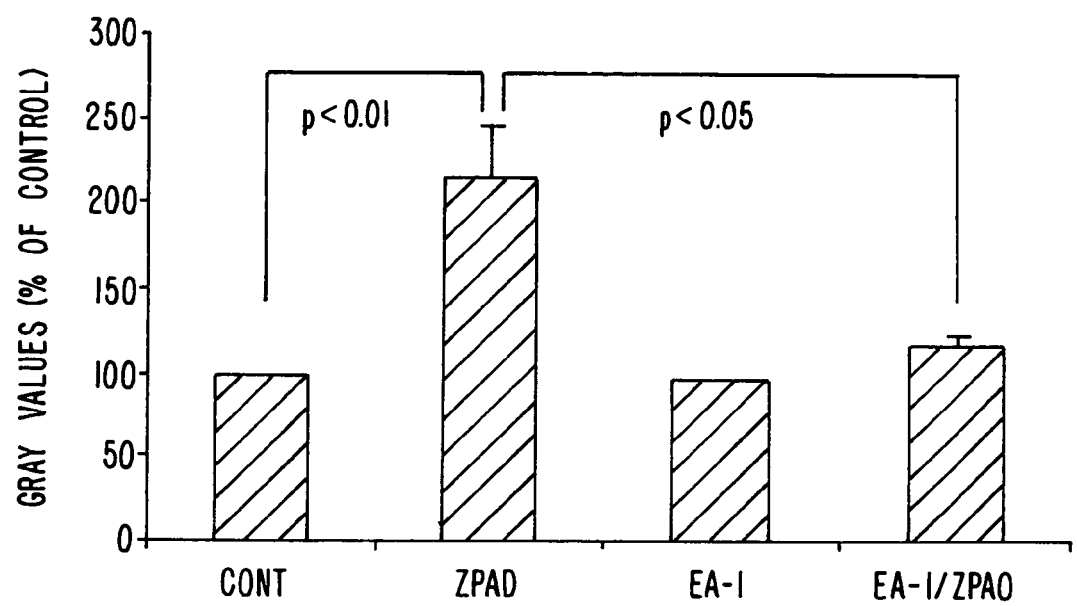
FIG. 11 illustrates that like CEL5-172, the cathepsin D inhibitor EA-1, by itself, did not detectably change the concentration of either the phosphorylated taus fragment, but it exhibited a much higher blocking effect than CEL5-172.

Another four groups of cultured entorhinohippocampal slices were maintained for 14 days and used to test the effect of EA-1: (1) control medium; (2) 20 µM of ZPAD; (3) a new selective inhibitor (EA-1 at 1 µM) of cathepsin D; (4) ZPAD combined with EA-1. Following this, the slices ere homogenized and samples processed for immunoblotting. Like CEL5-172, EA-1 by itself did not detectably change the concentrations of hyperphosphorylated tau fragments (see, FIG. 11); however, it exhibited a much higher blocking effect than CEL5-172. It is noted that EA-1 and CEL5-172 have the following structures, respectively:

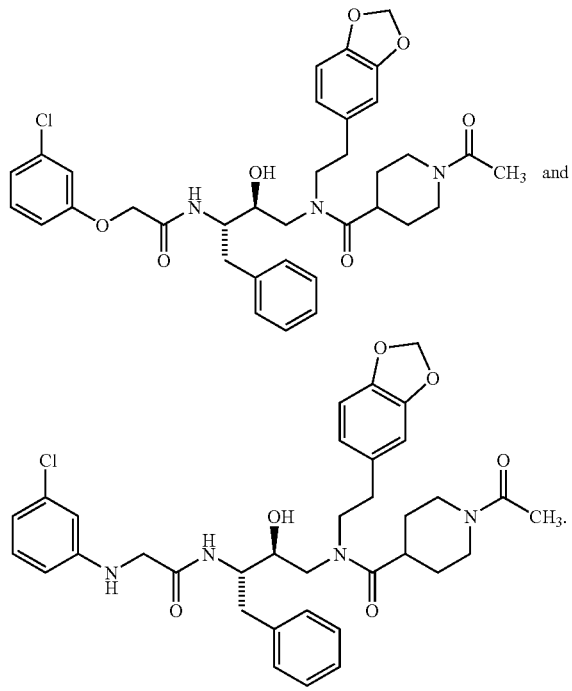

III. Example III

A. Assays and Abbreviations

1. Abbreviations Used

ACSF, artificial cerebrospinal fluid; EDTA, ethylenediaminetetraacetic acid; EGTA, ethyleneglycol bis (β-aminoethylether) N,N,N',N'-tetraacetic acid; PBS, phosphate-buffered saline; SDS, sodium dodecyl sulphate; TBS, Tris-buffered saline; ZPAD, N-CBZ-L-phenylalanyl-L-alanine-diazomethylketone.

2. Preparation and Maintenance of Hippocampal Slice Cultures

Organotypic hippocampal cultures were prepared using the technique of Stoppini, et al. (*J. Neurosci. Meth.*, 37:173–182 (1991)). Briefly, hippocampi were harvested from brains of 9–11 days old Sprague-Dawley rat pups under sterile condition. Horizontal sections vertical to the long axis of hippocampus were cut at 400 μm and collected in a cutting medium consisting of MEM (with Earle's salts, Gibco), 25 mM HEPES, 10 mM Tris Base, 10 mM Glucose, and 3 mM MgCl2 (pH 7.2). Slices were positioned onto 30 mm cell culture inserts (Millicell-CM, Millipore, Bedford, Mass.) that were placed in 6 well culture trays with 1 ml of growth medium (MEM with Hank's salts, Gibco, 20% horse serum, 3 mM glutamine, 25 mM HEPES, 5 mM NaHCO3, 25 mM glucose, 0.5 mM ascorbate, 2 mM $CaCl_2$, 2.5 mM MgCl2, 0.5 mg/l insulin, and penicillin, pH 7.2; 9). The cultures were incubated at 35° C. with a 5% $CO_2$-enriched atmosphere with medium changed every other day until use. Incubations were carried out for 14 days before the start of experiments. This period is sufficient for the slices to take on a variety of adult characteristics (Bahr, *J Neurosci Res.*, 42:294–305 (1995); and Muller, et al., *Dev. Brain Res.*, 71:93–100 (1993)).

Experiments were carried out using a yoked design in which one of the six culture trays was always used as a control and values for experimentally treated slices were expressed as percents of the same plate control. Hippocampal slice cultures were exposed to medium containing one of three cathepsin D inhibitors (see, below) or to 'ZPAD' (N-CBZ-L-phenylalanyl-L-alanine-diazomethylketone), a selective inhibitor of cathepsins B and L (Green, et al., *J. Biol. Chem.*, 256:1923–1928 (1981); Richardson, et al., *J. Cell Biol.*, 107:2097–2107 (1988); and Shaw, et al., *Biochem. J.*, 186:385–390 (1980)). ZPAD was used at 20 μM, and both ZPAD and cathepsin D inhibitors were dissolved first in dimethyl sulfoxide (DMSO), then diluted to the concentrations needed using culture media. Equal amount of DMSO (<0.1%) was also applied to control slices.

3. Recording and Stimulation

Physiology experiments were performed on hippocampal slices kept in vitro for 2 weeks followed by being incubated with cathepsin inhibitors for an additional six days. The slices were placed in a submersion chamber containing artificial cerebrospinal fluid (ACSF) and maintained at room temperature. The flow rate of ACSF through the recording chamber was 1.2 ml/min. Electrodes were positioned 120 min after the slices had been placed in the chamber. Patch-clamp recordings were made from pyramidal neurons in the stratum pyramidale of area CA1. The recording pipettes had resistances of 3–5 MΩ. Holding potentials were −70 mV. Currents were recorded using a patch amplifier with a 4-pole low-pass Bessel filter at 2 kHz and digitized at 10 kHz. Field EPSPs were simultaneously recorded in stratum radiatum using low resistance (2–6 MΩ) microelectrodes. All experiments involved stimulation of the Schaffer collateral/commissural afferents at 0.033 Hz using a bipolar stimulating electrode placed in stratum radiatum and were performed at room temperature.

4. Western Blot Analysis

Hippocampal slices were collected and sonicated in 10 mM Tris-HCl buffer (pH 7.4) containing 0.32 M sucrose, 2 mM EDTA, 2 mM EGTA, and 0.1 mM leupeptin. Aliquots of homogenate (80–100 μg protein/lane) were diluted with equal amount of 2× sample buffer [1× sample buffer consists 2% sodium dodecyl sulphate (SDS), 50 mM Tris-HCl (pH 6.8), 10% 2 mercaptoethanol, 10% glycerol and 0.1% bromophenol blue]. After heated to 90–100° C. for 5 min, proteins were subjected to SDS-PAGE performed according to the method of Laemmli (*Nature*, 227:680–685 (1970)) using 10% polyacrylamide gel; and then transferred on to nitrocellulose membranes as described by Towbin, et al. (*Proc. Natl. Acad. Sci. USA*, 76:4350–4354 (1979)). Nitrocellulose membranes were first incubated in 3% gelatin in Tris-buffered saline (TBS) for 1 hr at room temperature, followed by incubation with 1% gelatin in TBS with 0.5% Tween 20 (TTBS) containing antibodies that recognize either the phosphorylated tau protein (AT8; 1:500; Innogenetics, Belgium), unphosphorylated tau protein (tau 1, PC1 C6; 1:100; Boehringer Mannheim, Indianapolis, Ind.), or anti-cathepsin D antibodies (1:100; Oncogene Science, Cambridge, Mass.) at room temperature overnight. After two washes with TTBS for 5 min, membranes were incubated with alkaline phosphatase conjugated anti-mouse IgG (1:3000; BioRad) for 2 hrs at room temperature, then visualized with solution containing nitroblue tetrazolium and 5-bromo-4-chloro-3-indolyl-phosphate toluidine salt (BioRad) in dimethyl formamide according to the manufacture's instruction. Immunoblots were scanned and the digitized images were quantitatively analyzed by densitometry using the NIH Image analysis system program.

B. Results

Prior work showed that ZPAD and related drugs cause cultured slices to develop several characteristic features of the aged human brain including lysosomal hyperplasia (Bednarski, et al., *J. Neurosci.*, 17:4006–21 (1997); Bi, et al., *Exp Neurol.*, 158:312–327 (1999); Yong, et al., *Exp. Neurol.*, 157:150–160 (1999)), disruptions in the transport of hypothalamic releasing factors (Bi, et al., *J Comp Neurol.*, 401:382–94 (1998)), meganeurites (Bednarski, et al., *J. Neurosci.*, 17:4006–21 (1997); Bi, et al., supra (1999); Yong, et al., supra (1999)), amyloidogenic peptides (Bahr, et al., *Exp Neurol.*, 129:1–14 (1994)), hyperphosphorylated tau fragments (Bednarski, et al., *J. Neurochem.*, 67:1846–1855 (1996); Bi, et al., supra (1999)), and early stage versions of plaques and tangles (Bi, et al., supra (1999)). Importantly, certain of these features occur in regional patterns resembling those found in the aged human brain. No obvious changes in synaptic responses have been found after incubating hippocampal slices with ZPAD for 6–8 days (Fan and Lynch unpublished observation). Whether and to what degree cathepsin D inhibitors block the formation of hyperphosphorylated tau fragments was tested in slices exposed to both ZPAD and the inhibitors. Incubations continued for 2, 4, or 6 days after which the slices were tested for synaptic physiology or processed for histological or biochemical assays.

The three inhibitors used in the below experiments had molecular weights of 650–800 Da and Ki's for cathepsin D between 1–15 nM (see, FIG. 12). They were products of a synthesis program in which the crystal structure of cathepsin D complexed with the peptide-based natural product pepstatin served as a model with which to select building blocks for a combinatorial library. Equivalent energy conformations of a (hydroxyethyl) amine scaffold were grouped into families and computational methods (Lewis, et al., *J. Mol. Graph.*, 10:66–78, 106 (1992); Roe, Application and development of tools for structure-based drug design, University of California, San Francisco, USA (1995a); Roe, et al., *J. Comput. Aided Mol. Des.*, 9:269–82 (1995b)) used to position R1–3 moieties onto the scaffolds. Conformations with overlapping R1–R2 groups were eliminated to reduce the combinatorial problem. A library of 1000 compounds was prepared with parallel synthesis and screened with a fluorometric assay for activity against cathepsin D (Krafft, et al., *Methods Enzymol.*, 241:70–86 (1994)). The clusters for the R1–3 positions that generated the most active compounds were then used to build a small, second generation library (Kick, et al., *Chemistry & Biology*, 4:297–307 (1997)). Lower molecular weight compounds with better likelihood of membrane penetration were identified using additional small, optimization libraries (Haque, et al., *Med. Chem.*, 42:1428–1440 (1999); Lee, et al., *J. Am. Chem. Soc.*, 120: 9735 (1998)). These compounds were prepared in quantities sufficient for use with cultured slices.

Figure 13:
FIG. 13 illustrates the morphological and physiological effects of cathepsin inhibitors. Semi-thin sections through the cell body layer of field CA1 of cultured hippocampal slices given no treatment (A), a 6-day exposure to an inhibitor of cathepsins B and L (B), or a-6 day exposure to an inhibitor of cathepsin D (C). Note the presence in (B) of large numbers of small, dense bodies that in some cases are clustered into torpedo shaped expansions (arrows). These effects are sufficiently robust to be easily detected by naïve observers. The proliferation and expansions (meganeurites) are not found in (C) and there are no obvious morphological differences between this slice and the control. Synaptic responses recorded in field CA1 after 6 days of treatment with the cathepsin D inhibitor (EA-1) are shown in (D). EPSCs collected with whole cell clamp from the pyramidal cell bodies (i) have a rapid onset after stimulation (arrow) of the Schaffer-commissural fibers, are well developed, and have a waveform typically seen in slices tested at room temperature. Field EPSPs in the apical dendrites (ii) are recorded without spikes or after potentials. As in previous reports, the amplitude of extracellular monosynaptic responses is smaller in cultured slices than is the case for acute slices. IPSCs were well developed in treated slices (iii) as can be seen in the Schaffer-commissural responses collected with the membrane potential set to −50 mV. A negative going EPSC recorded at −70 mV is also shown.

Six-day incubations with the inhibitor 'EA-1', in marked contrast to ZPAD or chloroquine, did not produce detectable increases in the number of lysosomes, as can be seen in semi-thin sections through hippocampal field CA1 (see, FIGS. 13A, B and C). Blockade of cathepsin D thus does not reduce protein breakdown to a degree sufficient for triggering lysosomal hyperplasia. This accords with evidence that the enzyme participates in limited proteolysis of biologically active proteins rather than in bulk degradation and that cathepsin D (−/−) mice are viable well into post-natal life (Saftig, et al., *J. Biol. Chem.*, 271:27241–27244 (1996)).

Carboxy-terminal fragments of the amyloid precursor protein are a characteristic feature of slices treated with ZPAD, chloroquine, or exogenous amyloid (Bahr, et al., *Exp Neurol.*, 129:1–14 (1994); Bahr, et al., *J Comp Neurol.*, 397:139–147 (1998)). The cathepsin D inhibitors did not induce these peptides (not shown). The compounds were also without evident effect on inhibitory and excitatory synaptic currents, extracellular field potentials, or postsynaptic responses to repetitive stimulation (FIG. 13D). In all, the new inhibitors are selective in that they do not elicit anatomical and biochemical changes found with inhibitors of cathepsins B and L, or with more generalized lysosomotropic agents, and do not influence sensitive physiological indices.

Figure 14:
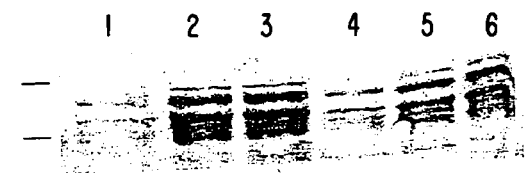
FIG. 14 illustrates the effects of cathepsin inhibitors on concentrations of phosphorylated tau fragments. Cultured slices were incubated for 6 days with an inhibitor of cathepsins B and L (ZPAD), an inhibitor of cathepsin D, or both. Western blots were then prepared from slice homogenates using an antibody against the hyperphosphorylated tau found in human neurofibrillary tangles. The top panels show immunostaining in the 25–35 kDa region of the blots. ZPAD increased the concentrations of phosphorylated bands in this region over the levels found in controls. The cathepsin D inhibitors CEL-5 (A, lane 4) and EA-1 (B, lane 3) had no detectable effect on concentrations of the peptide. Slices treated with ZPAD and a cathepsin D inhibitor (A, lanes 5 and 6;B, lane 4) tended to have greater concentrations than controls (A and B, lane 1) but clearly not to the level found with ZPAD alone (A, lanes 2 and 3;B, lane 2). The bottom panels summarize analysis of AT8 staining from five separate experiments with all values expressed as percent of yoked controls. *, P<0.05; **; P<0.01; error bars, standard errors. C. Western blots showing the native tau proteins probed by tau 1 and AT8 antibodies. Lane 1, control; lane 2, incubated with ZPAD; Lane 3, incubated with EA-1; Lane 4, incubated with EA-1 and ZPAD.
Figure 14:
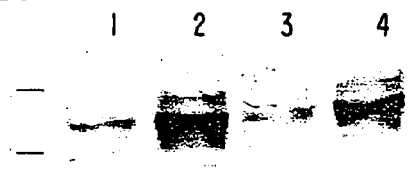
Figure 14:
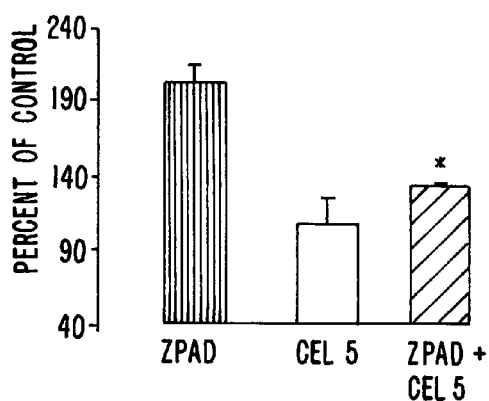
Figure 14:
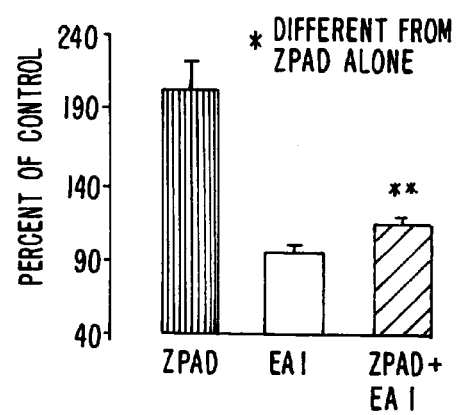
Figure 14:
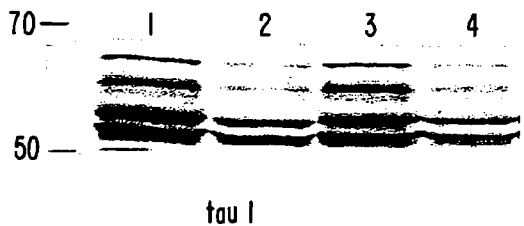
Figure 14:
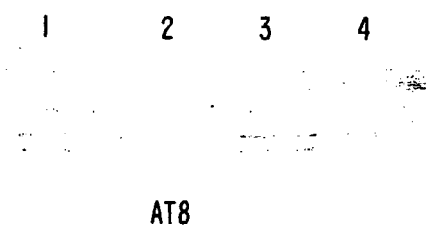

Antibodies (e.g., 'AT8'; Goedert, et al., *Proc. Natl. Acad. Sci. USA*, 90:5066–70 (1993); Greenberg, et al., *Proc. Natl. Acad. Sci. USA*, 87:5827–31 (1990)) against hyperphosphorylated tau or paired helical filaments in human brain variably label a 29 kDa band in western blots from adult rat brains (Bednarski, et al., *J. Neurochem.*, 67:1846–1855 (1996)) or 'mature' cultured slices (Bi, et al., supra (1999)). Antibodies against native tau recognize this peptide to a lesser degree than they do tau itself; AT8, conversely, labels the 29 kDa peptide much more intensely than it does native tau (Bi, et al., supra (1999)). Moreover, the interaction of native tau and the 29 kDa peptide with tau 1 antibody is eliminated by phosphatase inhibitors. These results established that the 29 kDa band consists mainly of hyperphosphorylated tau fragments ('tau 29'). Immunoblots probed with AT8 confirmed earlier reports that a 6-day treatment of hippocampal cultures with inhibitors of cathepsins B and L causes a marked increase in the concentration of tau 29 (FIG. 14A, upper panels; lanes 1 vs 2/3). Six-day incubations with the cathepsin D inhibitor CEL5 at 5 μM (lane 4) had little if any effect in this regard. They did, however, markedly reduce the increase in tau-29 produced by ZPAD (lanes 4,5). The bottom segment of FIG. 14A summarizes results from 5 separate experiments, each involving 6–8 slices per treatment condition. As shown, ZPAD by itself caused a 104±18% (mean±s.e.m.) increase in the hyperphosphorylated tau fragment, a value which was reduced to 34±18% in the presence of the cathepsin D inhibitor. Note that concentrations of the fragment in slices treated with CEL5 by itself were the same as those in control slices. The difference between the two conditions (ZPAD vs. ZPAD+CEL5) was in the predicted direction and statistically significant. Results similar to these were obtained with two small, structurally distinct non-peptide cathepsin D inhibitors. FIG. 14B summarizes the results for EA-1. This compound again had no detectable effects on tau 29 concentrations (lane 3 of FIG. 14B), but virtually eliminated the increase caused by ZPAD (compare lanes 2 and 4). Densitometric measurements for 5 experiments (FIG. 14B, bottom) confirmed that fragment levels were not statistically different from control in slices exposed to ZPAD and the cathepsin D inhibitor. Incubation with ZPAD and cathepsin D inhibitors did not cause detectable changes in native tau when probed with AT8 (FIG. 14C), while a marked decrease was revealed with tau 1 antibodies (FIG. 14C; see, the following section for detailed analysis).

Figure 15A:
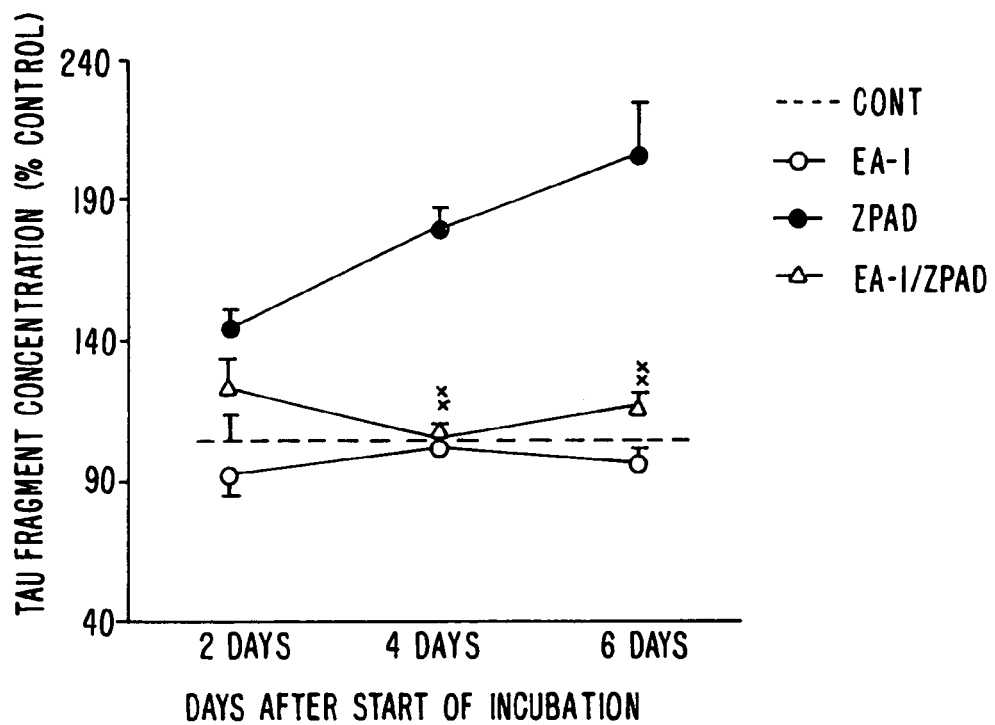
FIGS. 15A and 15B illustrates the time course and dose dependency for suppression of phosphorylated tau fragments by a cathepsin D inhibitor. (A). Cultured hippocampal slices were incubated for 2, 4, or 6 days with the cathepsin B/L inhibitor-ZPAD, the cathepsin D inhibitor-EA-1, or both. Western blot analyses for phosphorylated tau fragments were carried out at the end of the incubation with densitometric values expressed as percent of concentrations in yoked controls. ZPAD induced increases were detectable after 48 hrs and continued to grow thereafter. The cathepsin D inhibitor had no apparent effect but blocked the increases produced by ZPAD at all time points. (B). Slices were incubated with ZPAD, EA-1, or ZPAD plus the indicated concentrations of EA-1 for six days. The cathepsin D inhibitor had no detectable effects on concentrations of phosphorylated tau fragments at the concentrations tested. A dose of 1 µM caused a sizeable decrease in the effect of ZPAD while 5 µM completely suppressed it. *, P<0.05; **, P<0.01; error bars, standard errors.
Figure 15B:
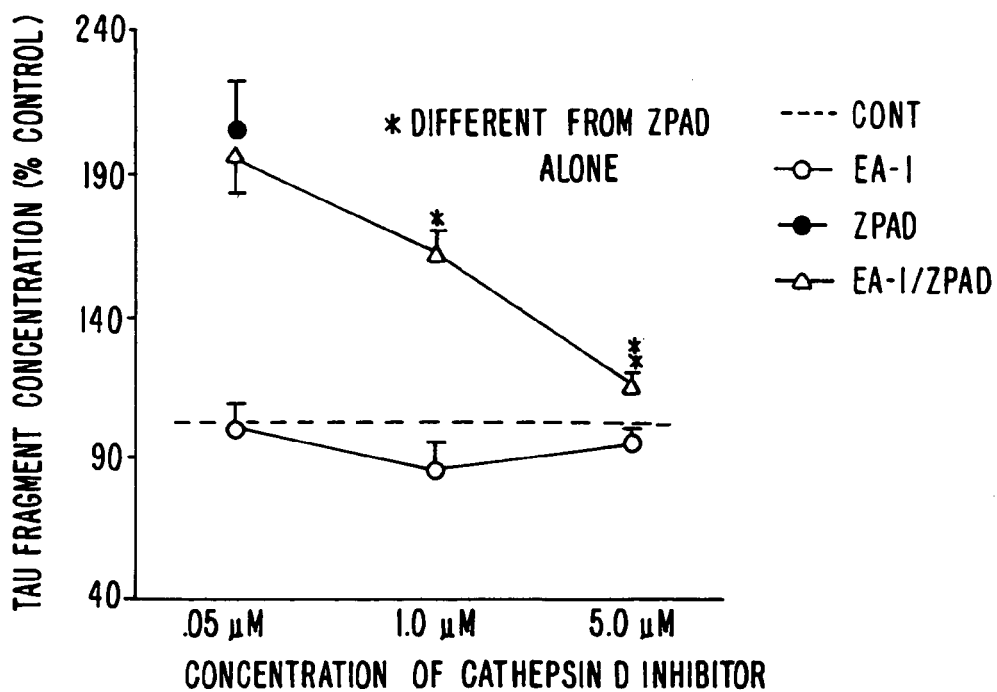

FIG. 15 describes the time and dose dependencies of the interactions between cathepsin inhibitors. ZPAD induced increases in the phosphorylated tau fragment appeared at 48 hrs—the earliest time point tested—and increased steadily thereafter (FIG. 15A). The effect of the cathepsin D inhibitor was evident from the first measurement and resulted in a complete blockade of the ZPAD-elicited changes by 96 hrs. The inhibitor EA-1 had dose dependent effects in slices treated with ZPAD for 6 days (FIG. 15B); threshold concentration appeared to lie between 0.05 (no detectable effect) and 1.0 μM (41% reduction in ZPAD induced fragments). Note that the cathepsin D inhibitor by itself had no effect on tau 29 concentrations at any time point or dosage.

Figure 16A:
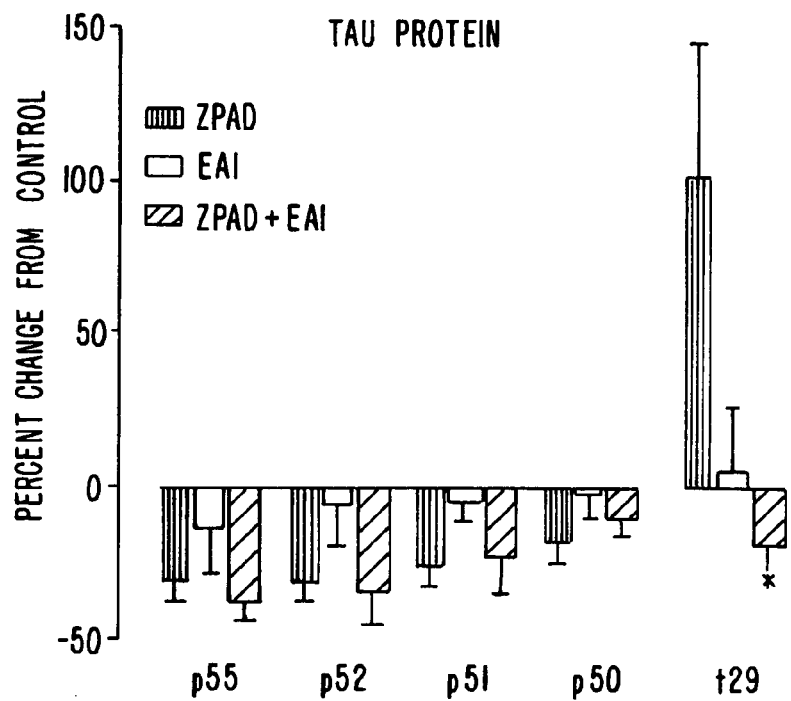
FIGS. 16A and 16B illustrates the effects of cathepsin inhibitors on tau and cathepsin D isoforms. Slices were incubated with ZPAD, EA-1, or both for 6 days after which Western blots were used to assess the concentrations of the target proteins with tau 1 antibodies (A), or anti-cathepsin D antisera (B). Densitometeic values were expressed as percent change from the concentrations in yoked control slices. (A). ZPAD caused sizeable reductions in four unphosphorylated isoforms of native tau; EA-1 was without effect itself and did not block the changes produced by ZPAD. ZPAD also generated a large increase in a 29 kDa tau fragment; this was completely blocked by EA-1. (B). ZPAD resulted in modest increases in procathepsin D and larger increases in the active, heavy chain variant of the protease. EA-1 suppressed the second of these effects.
Figure 16B:
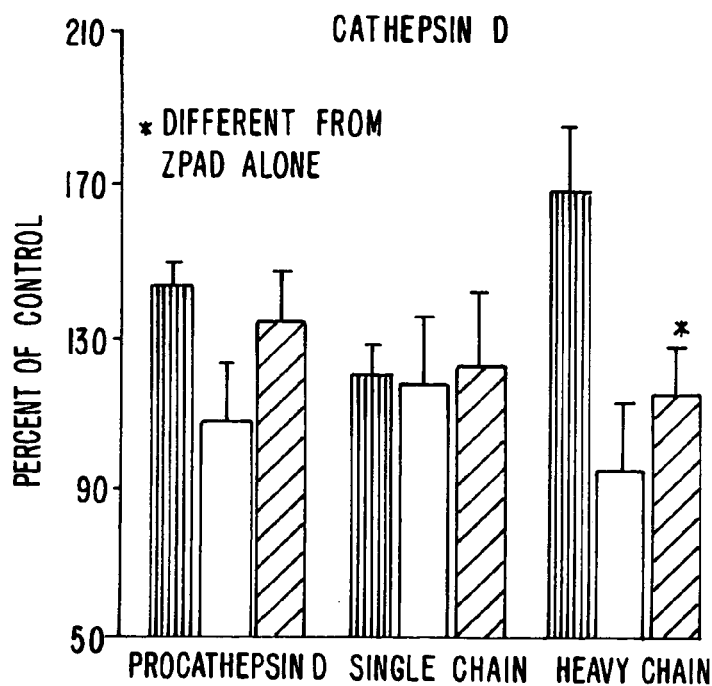

Increases in tau fragments are accompanied by measurable decreases in the concentration of native tau, as shown in the experiment summarized in FIG. 16A. An antibody against native (unphosphorylated) tau was used to measure the effects of six-day treatments with ZPAD on the concentrations of four known tau isoforms. As described in FIG. 16, tau concentrations in the experimental slices (solid bars) were reduced by an average of 19–32% from yoked controls (open bars) (p<0.01, ttest, 2-tail, n=8) and this was accompanied by a large increase (101%) in the weakly labeled 29 kDa fragments. The inhibitor EA-1 blocked the latter effect, but not the former. Conversion of cathepsin D into active forms may involve autocatalysis (Conner, Biochem. J., 263: 601–604 (1989); Conner, et al., Biochem., 28:3530–3533 (1989); and Hasilik, et al., Eur. J. Biochem., 125:317–321 (1982)). If so, then the inhibitors used here could indirectly block the formation of tau fragments by preventing the increases in lysosomal and cytoplasmic cathepsin D that develop within hours of chemically induced lysosomal dysfunction (Bednarski, et al., supra (1998); Hoffman, et al., Neurosci. Lett., 250:75–78 (1998)). To test whether cathepsin D inhibitors have any effect on the biosynthesis and maturation of cathepsin D, cultured hippocampal slices were treated with inhibitor alone or inhibitor plus ZPAD. EA-1 by itself did not detectably alter the levels of cathepsin D isoforms at concentrations from 50 nM to 5 μM (FIG. 16B). When hippocampal cultures were incubated with ZPAD and cathepsin D inhibitor, the levels of procathepsin D and single chain cathepsin D were similar to those observed in cultures treated with ZPAD alone. However, the increase in heavy chain isoform was substantially reduced (70% to 15%, FIG. 16) in the presence of EA-1.

C. Discussion

The above data constitute the first results on the effects of transiently and selectively suppressing cathepsin D in mature brain tissue. The novel inhibitors did not induce a robust lysosomal hyperplasia, an effect typically seen with pharmacological or genetic disturbances of intra-lysosomal functioning (Bednarski, et al., J. Neurosci., 17:4006–21 (1997); Bi, et al., supra (1999); Braak, et al., Acta Neuropathol., 46:79–83 (1979); Purpura, et al., Brain Res., 116: 1–21 (1976); Yong, et al., supra (1999)). The compounds did not cause evident physiological changes over the time courses tested and leave unchanged biochemical measures sensitive to cathepsins B/L inhibitors or to the broad-spectrum inhibitor chloroquine. It appears, then, that inhibition of cathepsin D to a degree sufficient to block specific biochemical reactions (below) has discrete consequences and, in general, is well tolerated by brain tissue for at least several days.

The findings also provide a direct test of the hypothesis that the rapid formation of hyperphosphorylated tau fragments occurring in association with lysosomal dysfunction is due to cathepsin D, or cathepsin D-like aspartyl proteases. Three distinct inhibitors produced near complete suppression of the increases that normally follow pharmacologically induced lysosomal dysfunction. The blocking effects were in evidence from the first appearance of tau fragmentation and had threshold concentrations in the sub-micromolar range. That the inhibitors did not reduce baseline levels may indicate that the fragments have a long half-life, a point of possible significance with regard to the production of tangles. The differential effects of cathepsin D inhibitors on ZPAD-induced tau 29 vs basal level tau 29 demonstrate that the blocking effect is not due to modification of the antigenic epitopes by these non-peptidic compounds. Cathepsin D inhibitors markedly reduced the formation of tau 29, but did not reverse decreases in native tau, suggesting that cathepsin D is not solely responsible for the breakdown of tau protein that occurs following pharmacologically induced lysosomal dysfunction.

Inhibition of cathepsin B and L increases procathepsin D and its maturation into the active, two-chain form (composed of heavy and light chain) within lysosomes, as described earlier (Bednarski, et al., supra (1998); Hoffman, et al., supra (1998)) and confirmed here. These events, in common with other circumstances involving lysosomal impairments (Nakamura, et al., Neurosci. Lett., 97:215–220 (1989); Nakanishi, et al., J. Neurochem., 68:739–739 (1997); Nakanishi, et al., Exp. Neurol., 126:119–128 (1994)) are accompanied by leakage of active cathepsin D into the cytoplasm (Bednarski, et al., NeuroReport, 9:2089–2094 (1998); Nakamura, et al., supra 1989; Nakanishi, et al., supra (1997); Nakanishi, et al., supra (1994)), reductions in the concentration of unphosphorylated tau proteins, and increases in hyperphosphorylated tau fragments. The cathepsin D inhibitors did not significantly affect the increases in pro- or single chain forms of cathepsin D, but blocked that for the heavy chain. This strongly suggests that autocatalysis plays an important role in the maturation of cathepsin D, as previously proposed (Conner, supra (1989); Hasilik, et al., supra (1982)), at least under conditions in which biosynthesis is accelerated. Blockade of heavy chain formation would presumably reduce the active cathepsin D available for leakage and thus for the neutral pH cleavage of tau at amino acids 200–257, the event that results in the 29 kDa product (Bednarski, et al., supra (1996); Kenessey, et al., J. Neurochem., 69:2026–2038 (1997)).

The potent and selective effects described above indicate that the inhibitors have therapeutic value. With longer incubation periods, hyperphosphorylated tau fragments in cultured slices assemble into structures having the appearance, size, and epitopes of early stage neurofibrillary tangles in human brain (Bi, et al., supra (1999)). Accordingly, there is reason to expect that blocking their formation would slow the production of a primary component of AD. Beyond this, extra-lysosomal cathepsin D is one of a collection (see, Murphy, et al., J. Biol. Chem., 274:11914–11923 (1999)) of enzymes that may generate Beta-amyloid (Austen, et al., Biomed. Pept Proteins Nucleic Acids, 1:243–6 (1995); Chevallier, et al., Brain Res., 750:11–9 (1997); Dreyer, et al., Eur. J. Biochem., 224:265–271 (1994); Estus, et al., Ann N Y Acad Sci., 674:148–148 (1992); Mackay, et al., Eur. J. Biochem., 244:414–425 (1997)) and has recently been linked to apoptosis (Isahara, et al., Neuroscience, 91:233–49 (1999); Levy-Strumpf, et al., Oncogene, 17:3331–3340 (1998); Ohsawa, et al., Arch. Histol. Cytol., 61:395–403 (1998); Roberg, et al., Am. J. Pathol., 152:1151–1156 (1988); Shibata, et al., supra (1998)).

Figure 12:
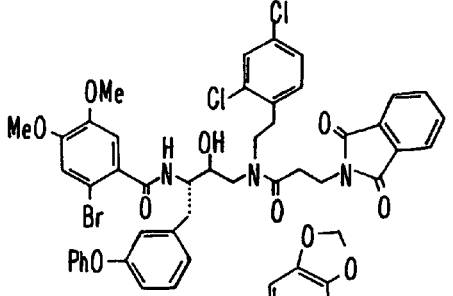
FIG. 12 illustrates the structures of three inhibitors used in the experiments set forth in Example III, all of which have molecular weights of 650–800 Daltons and Ki's for cathepsin D of between 1–15 nM.
Figure 12:
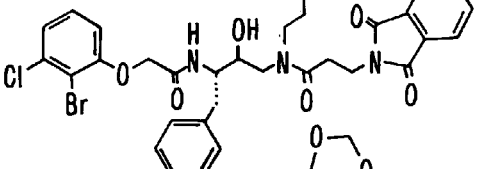
Figure 12:
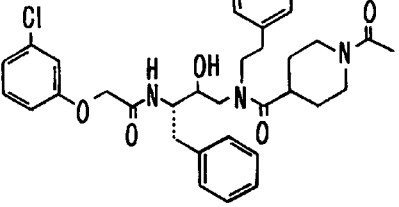

In view of the foregoing results, in a preferred embodiment of the present invention, the cathepsin D inhibitor is a compound selected from the group consisting of CEL5-A, CEL5-G and EA-1, the structures of which are set forth in FIG. 12.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purpose.

What is claimed is:

1. A method for modulating the processing of an amyloid precursor protein (APP), said method comprising contacting a composition containing said APP with an aspartyl protease inhibitor having the general formula:

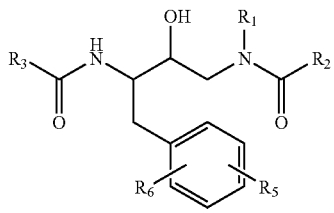

(I)

wherein:
- $R_1$, $R_2$ and $R_3$ are members independently selected from the group consisting of alkyl, substituted alkyl, aryl, substituted aryl, arylalkyl, substituted arylalkyl, aryloxyalkyl, substituted aryloxyalkyl, heteroaryl, substituted heteroaryl, heteroarylalkyl, substituted heteroarylalkyl, heterocycles, substituted heterocycles, heterocyclicalkyl and substituted heterocyclicalkyl; and
- $R_5$ and $R_6$ are independently selected from the group consisting of hydrogen, halogen, alkyl, substituted alkyl, aryl, substituted aryl, arylalkyl, substituted arylalkyl, aryloxyalkyl and substituted aryloxyalkyl; or $R_5$ and $R_6$ and the carbons to which they are bound join to form an optionally substituted carbocyclic or heterocyclic fused ring system having a total of 9- or 10-ring atoms within said fused ring system.

2. The method according to claim 1, wherein:
$R_1$ is a member selected from the group consisting of substituted alkylaryl, substituted aryl, substituted alkyl and substituted heterocyclic groups.

3. The method according to claim 2, wherein:
$R_1$ is a member selected from the group consisting of:

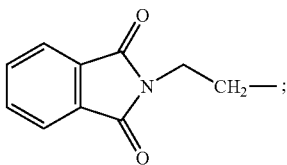

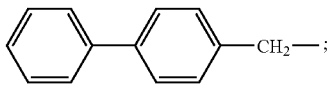

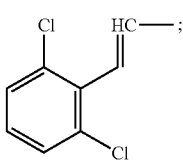

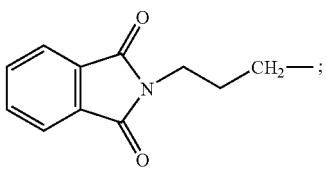

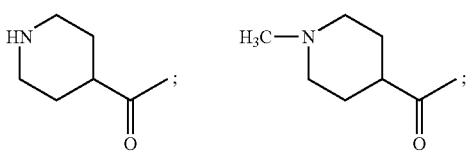

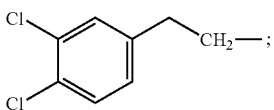

4. The method according to claim 1, wherein:
R2 is a member selected from the group consisting of substituted alkyl, heterocyclic and substituted heterocyclic groups.

5. The method according to claim 4, wherein $R_2$ is a member selected from the group consisting of:

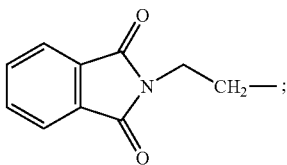

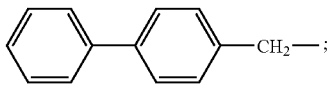

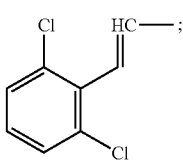

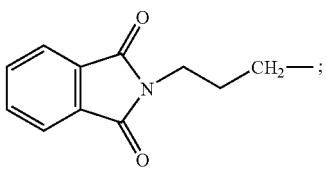

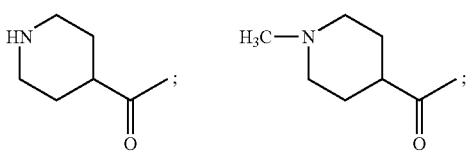

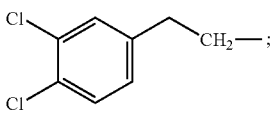

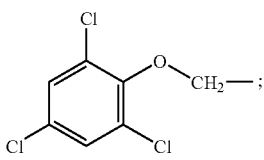

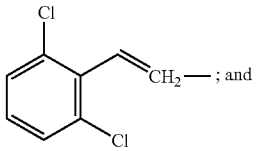

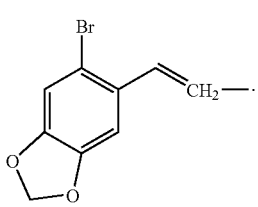

6. The method according to claim 1, wherein:
$R_3$ is a member selected from the group consisting of substituted alkyl and substituted aryl groups.

7. The method according to claim 6, wherein $R_3$ is a member selected from the group consisting of:

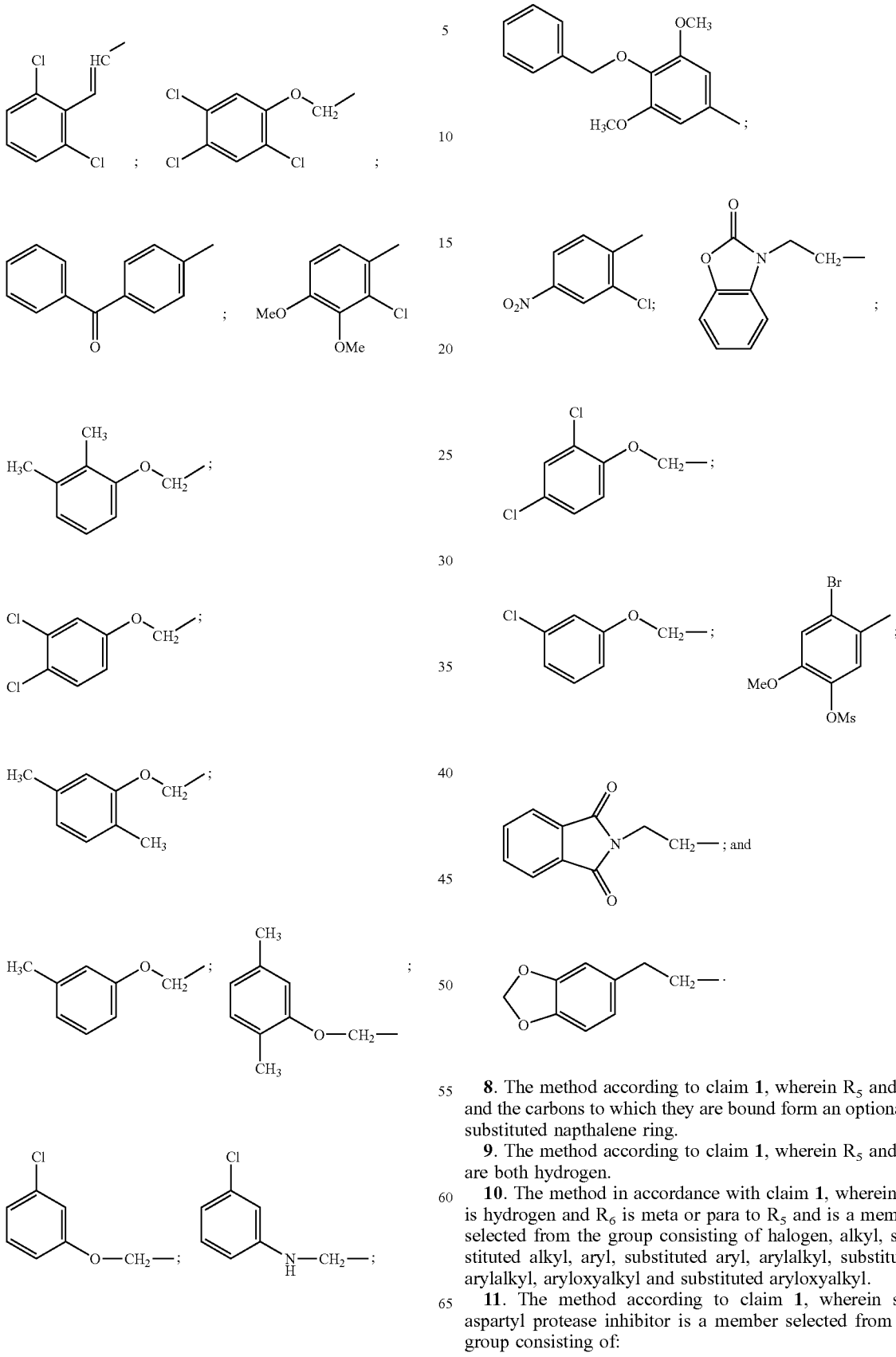

8. The method according to claim 1, wherein $R_5$ and $R_6$ and the carbons to which they are bound form an optionally substituted napthalene ring.

9. The method according to claim 1, wherein $R_5$ and $R_6$ are both hydrogen.

10. The method in accordance with claim 1, wherein $R_5$ is hydrogen and $R_6$ is meta or para to $R_5$ and is a member selected from the group consisting of halogen, alkyl, substituted alkyl, aryl, substituted aryl, arylalkyl, substituted arylalkyl, aryloxyalkyl and substituted aryloxyalkyl.

11. The method according to claim 1, wherein said aspartyl protease inhibitor is a member selected from the group consisting of:

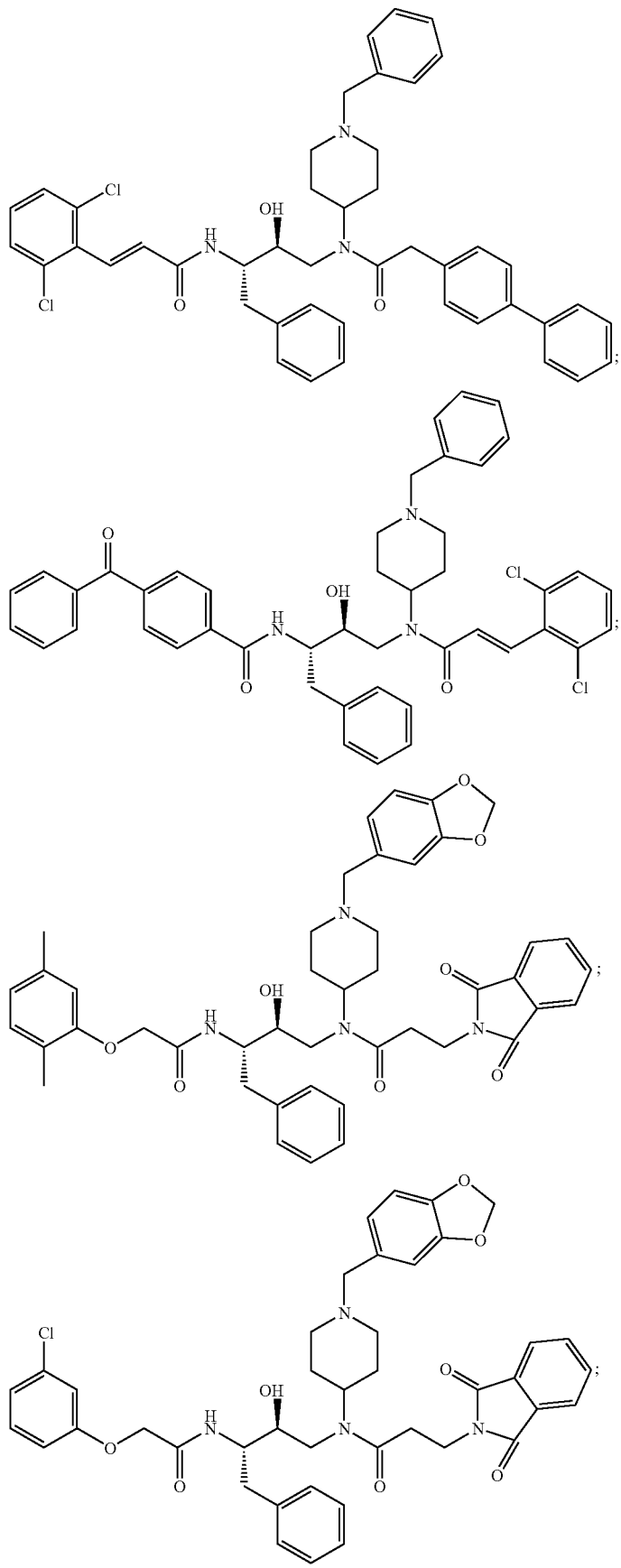

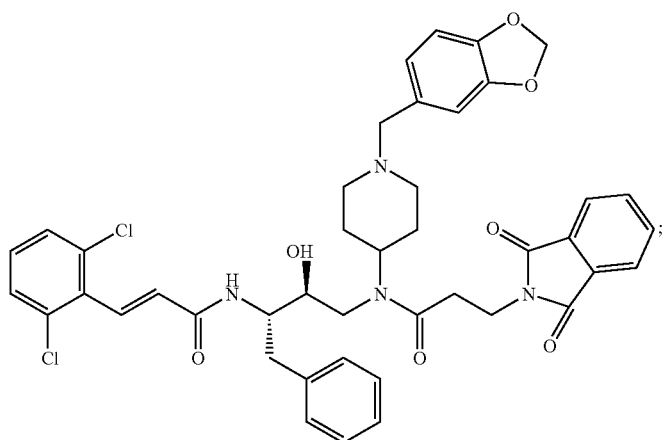
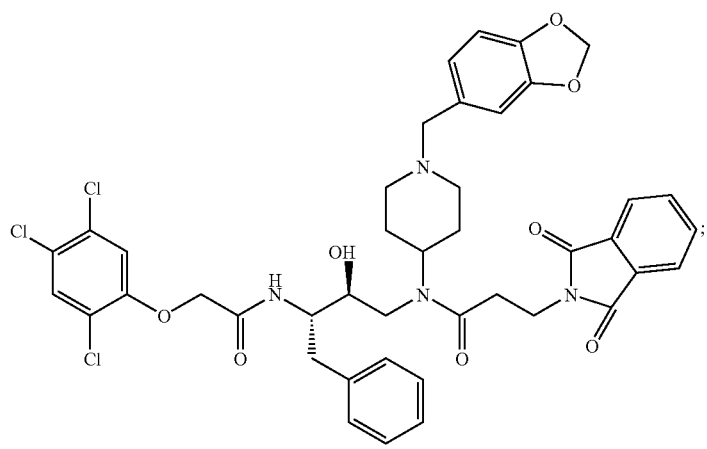
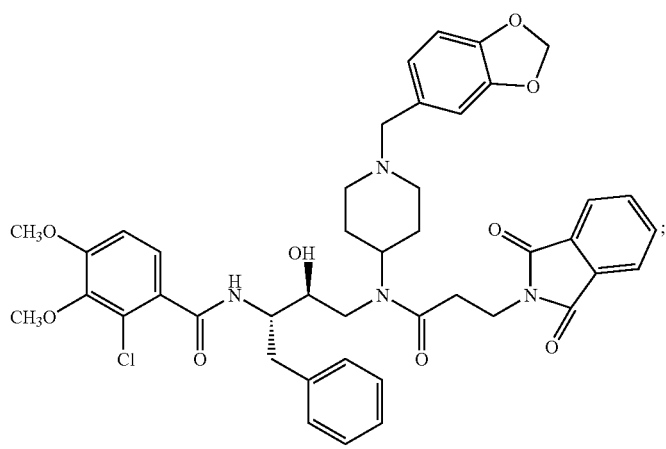

-continued
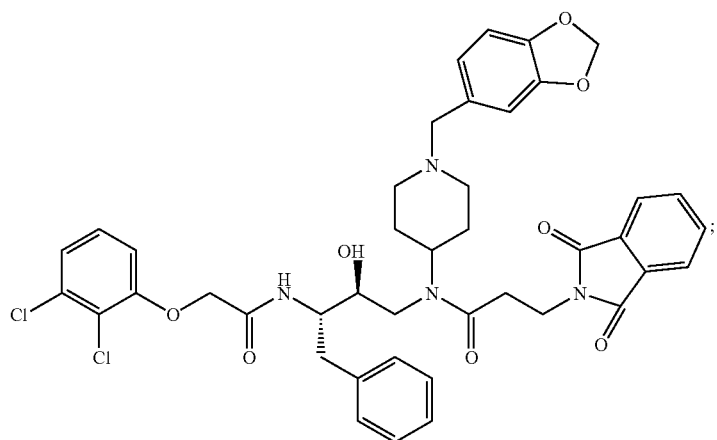
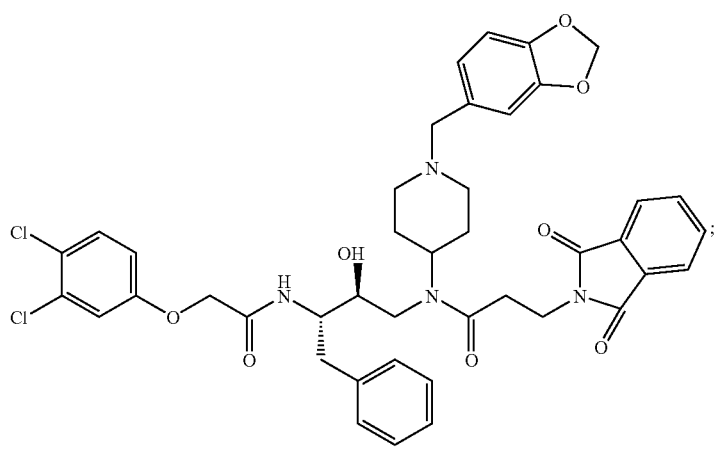
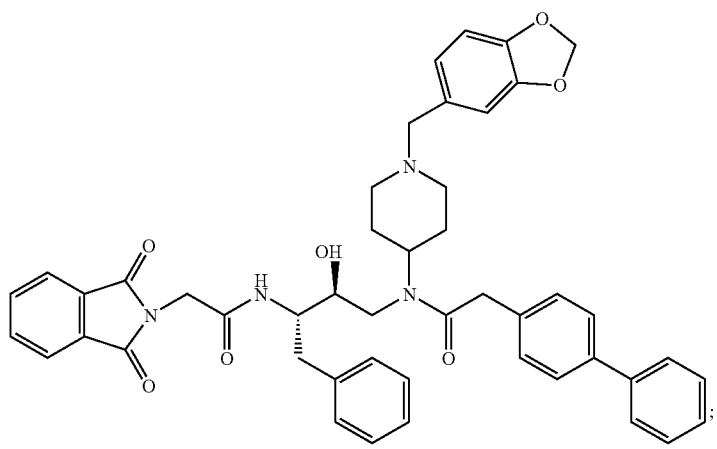

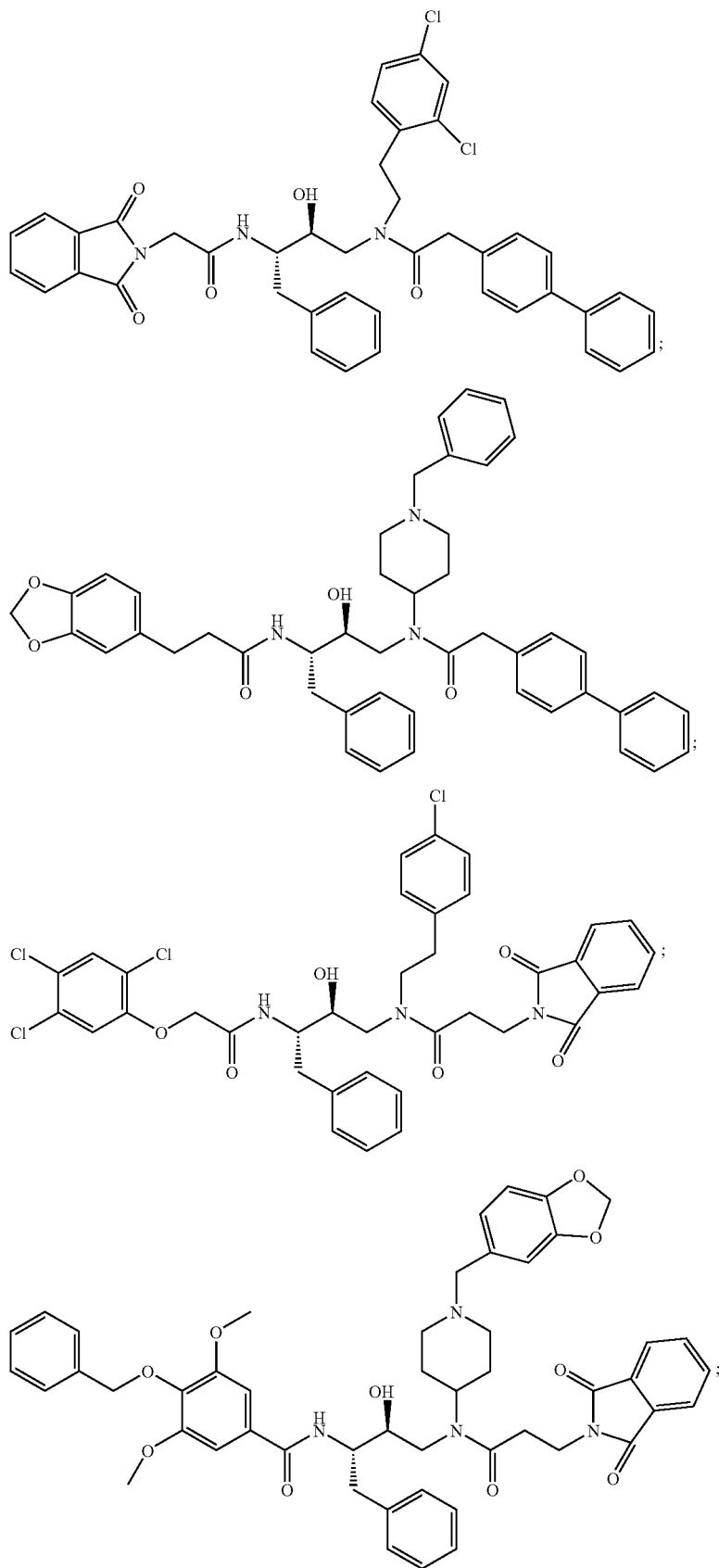

-continued
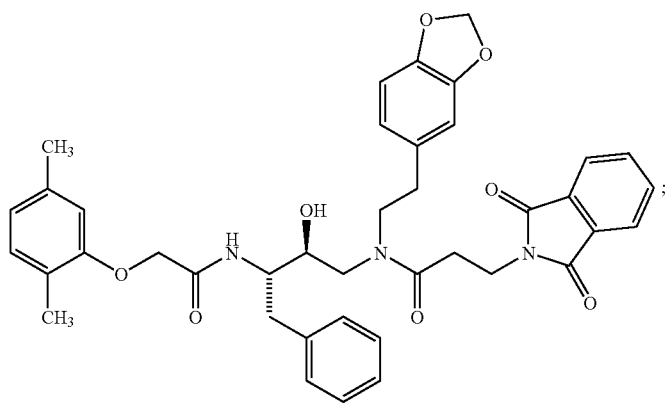
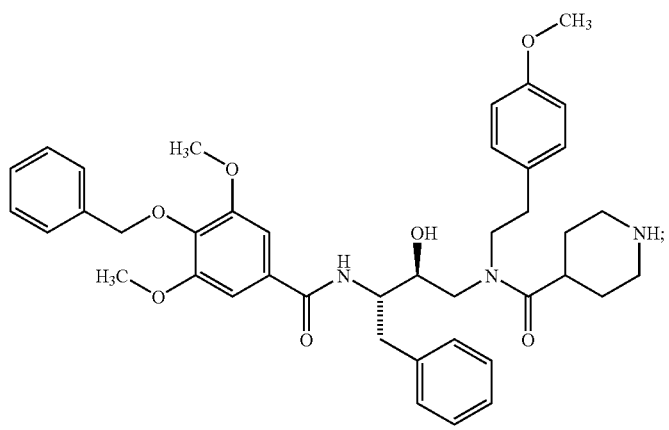
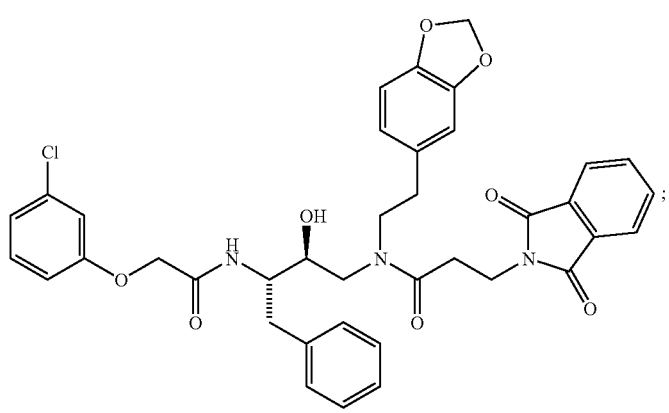
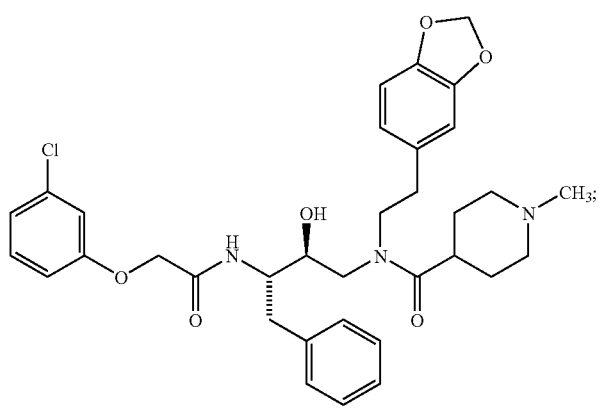

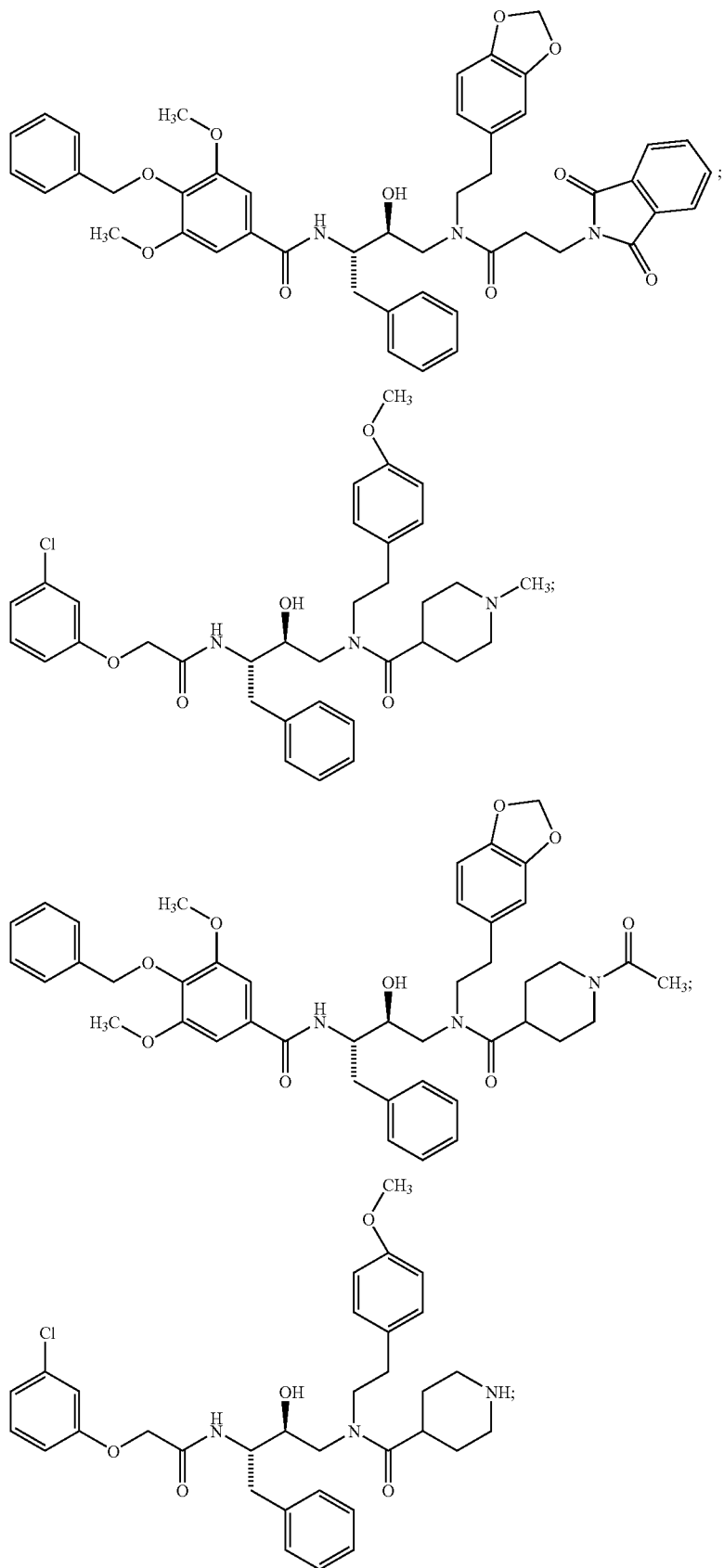

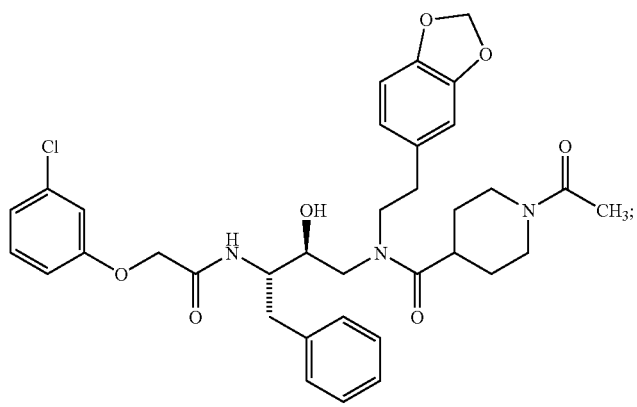
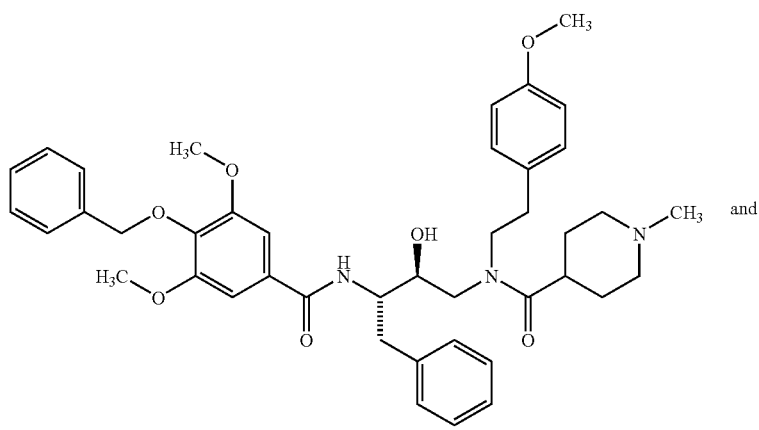
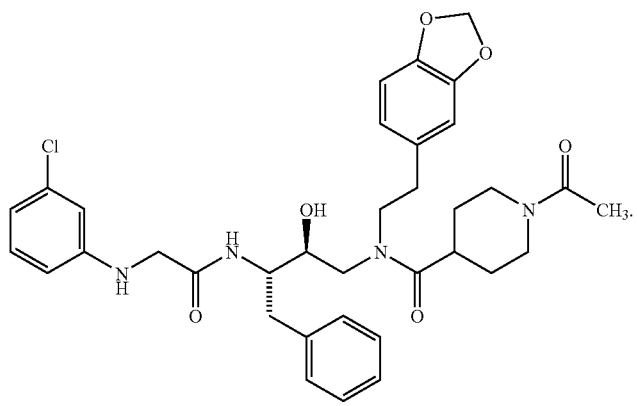

12. The method according to claim 1, wherein said aspartyl protease inhibitor is a member selected from the group consisting of:

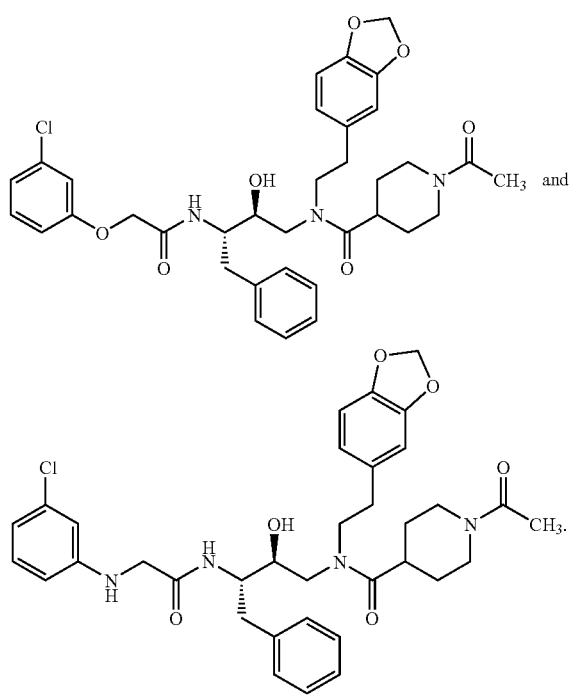

13. The method in accordance with claim 1, wherein said aspartyl protease inhibitor is a member selected from the group consisting of CEL5-A having the following structure:

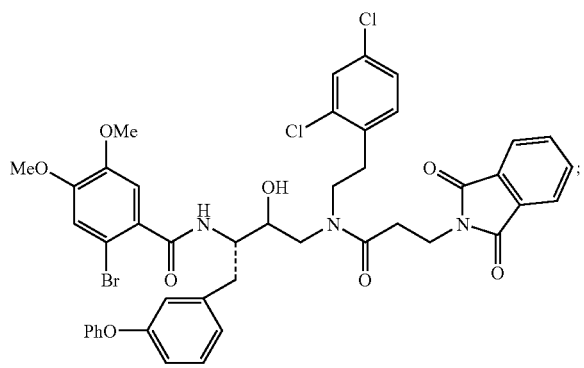

having the following structure: CEL5-G:

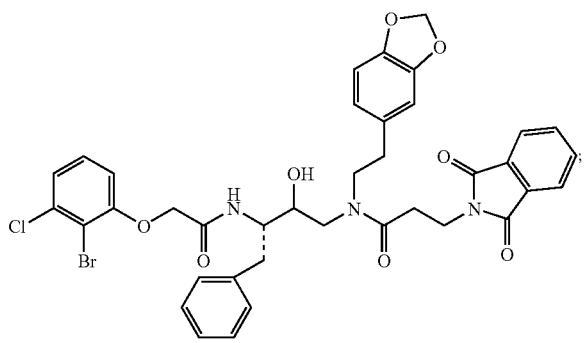

and

EA 1 having the following structure:

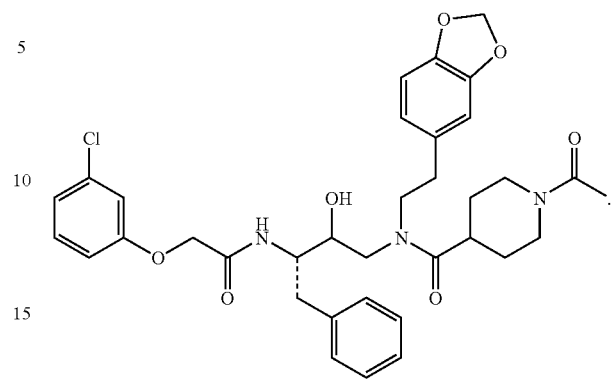

14. The method in accordance with claim 1, where in said composition is a body fluid.

15. The method in accordance with claim 13, 14, wherein said body fluid is cerebral spinal fluid.

16. The method in accordance with claim 1, whereby formation of amyloidogenic Aβ peptides (Aβ) is decreased compared to the amount formed in the absence of said aspartyl protease inhibitor.

17. The method in accordance with claim 1, whereby formation of α-sAPP is increased compared to the amount formed in the absence of said aspartyl protease inhibitor.

18. The method in accordance with claim 1, wherein the modulation is effected by modulating the activity of cathepsin D.

19. A method for modulating the processing of a tau-protein (τ-protein), said method comprising contacting a composition containing said τ-protein with an aspartyl protease inhibitor having the general formula:

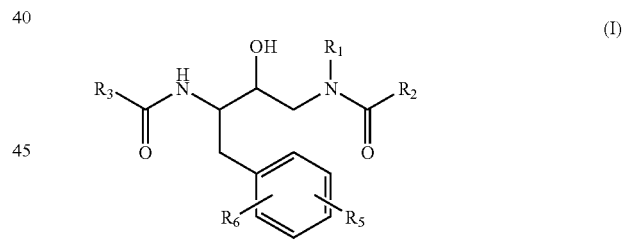

(I)

wherein:

$R_1$, $R_2$ and $R_3$ are members independently selected from the group consisting of alkyl, substituted alkyl, aryl, substituted aryl, arylalkyl, substituted arylalkyl, aryloxyalkyl, substituted aryloxyalkyl, heteroaryl, substituted heteroaryl, heteroarylalkyl, substituted heteroarylalkyl, heterocycles, substituted heterocycles, heterocyclicalkyl and substituted heterocyclicalkyl; and $R_5$ and $R_6$ are independently selected from the group consisting of hydrogen, halogen, alkyl, substituted alkyl, aryl, substituted aryl, arylalkyl, substituted arylalkyl, aryloxyalkyl and substituted aryloxyalkyl; or $R^5$ and $R^6$ and the carbons to which they are bound join to form an optionally substituted carbocyclic or heterocyclic fused ring system having a total of 9- or 10-ring atoms within said fused ring system.

20. The method according to claim 19, wherein:

$R_1$ is a member selected from the group consisting of substituted alkylaryl, substituted aryl, substituted alkyl and substituted heterocyclic groups.

21. The method according to claim 20, wherein:

$R_1$ is a member selected from the group consisting of:

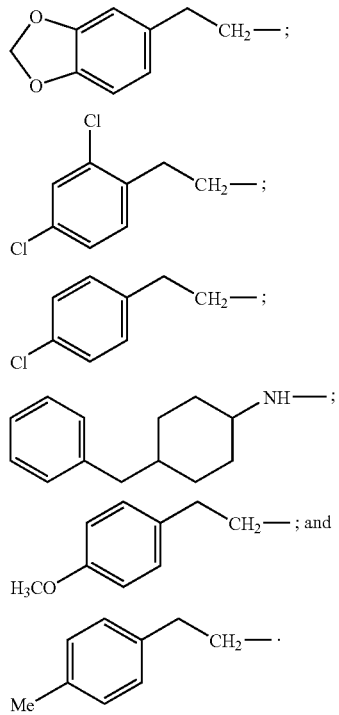

22. The method according to claim 19, wherein:

$R_2$ is a member selected from the group consisting of substituted alkyl, heterocyclic and substituted heterocyclic groups.

23. The method according to claim 22, wherein $R_2$ is a member selected from the group consisting of:

-continued

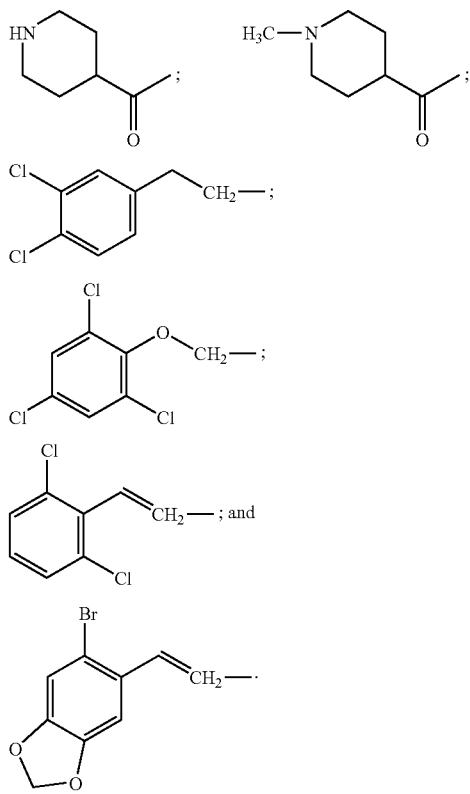

24. The method according to claim 19, wherein:

$R_3$ is a member selected from the group consisting of substituted alkyl and substituted aryl groups.

25. The method according to claim 24, wherein $R_3$ is a member selected from the group consisting of:

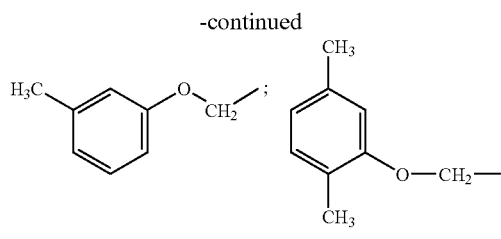
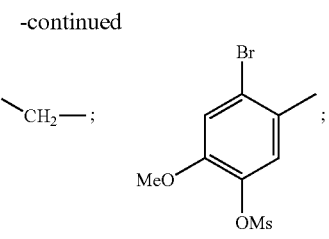

26. The method according to claim 19, wherein $R_5$ and $R_6$ and the carbons to which they are bound form an optionally substituted napthalene ring.

27. The method according to claim 19, wherein $R_5$ and $R_6$ are both hydrogen.

28. The method in accordance with claim 19, wherein $R_5$ is hydrogen and $R_6$ is meta or para to $R_5$ and is a member selected from the group consisting of halogen, alkyl, substituted alkyl, aryl, substituted aryl, arylalkyl, substituted arylalkyl, aryloxyalkyl and substituted aryloxyalkyl.

29. The method according to claim 19, wherein said aspartyl protease inhibitor is a member selected from the group consisting of:

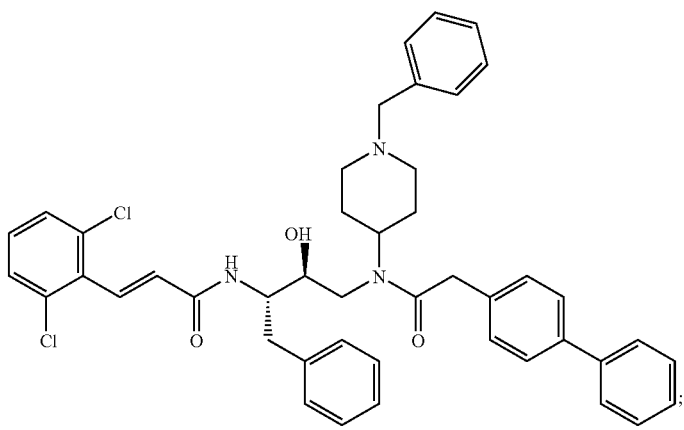

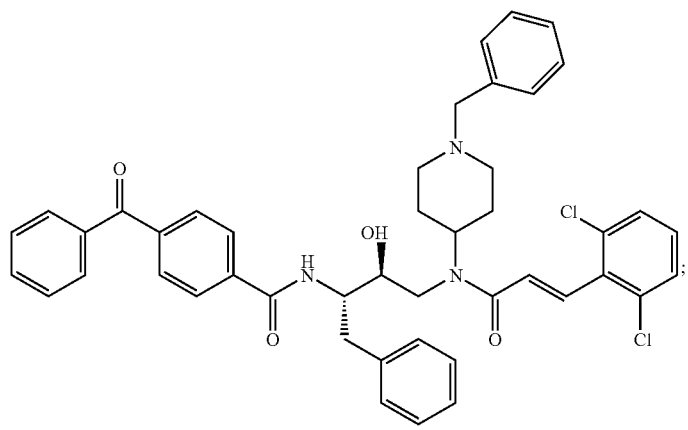
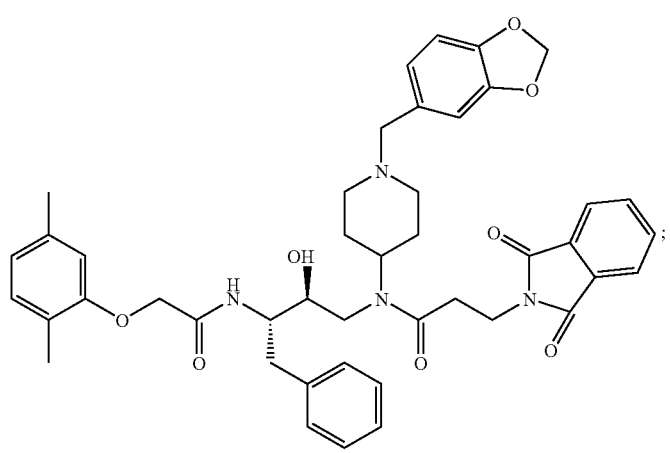
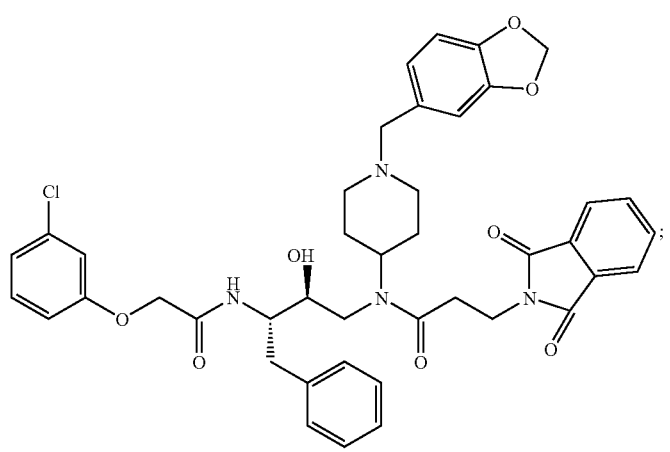

-continued
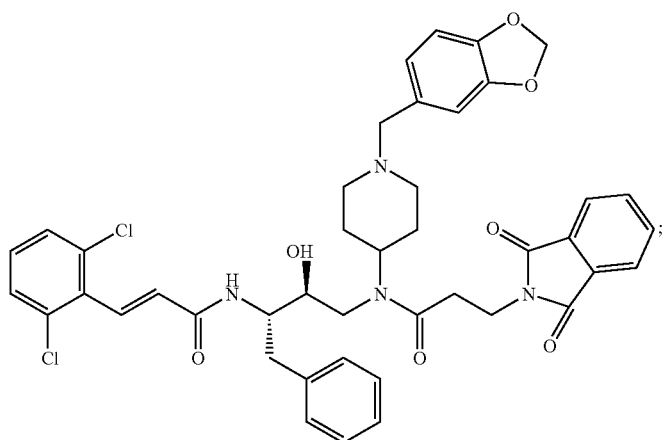
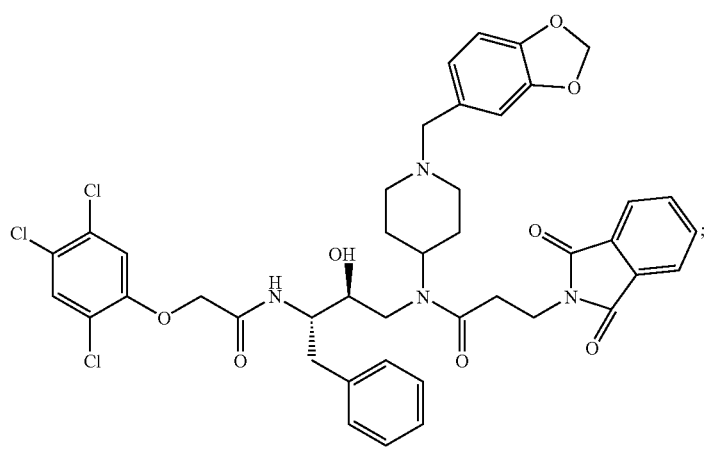
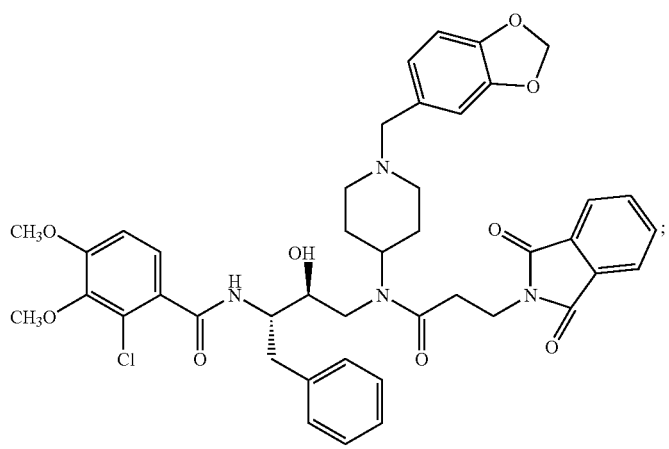

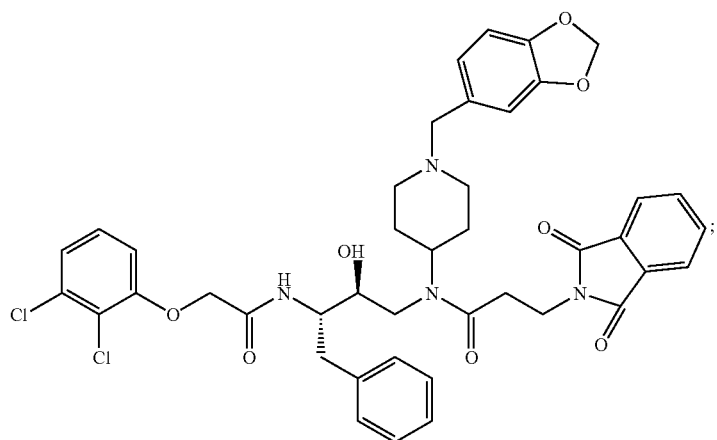
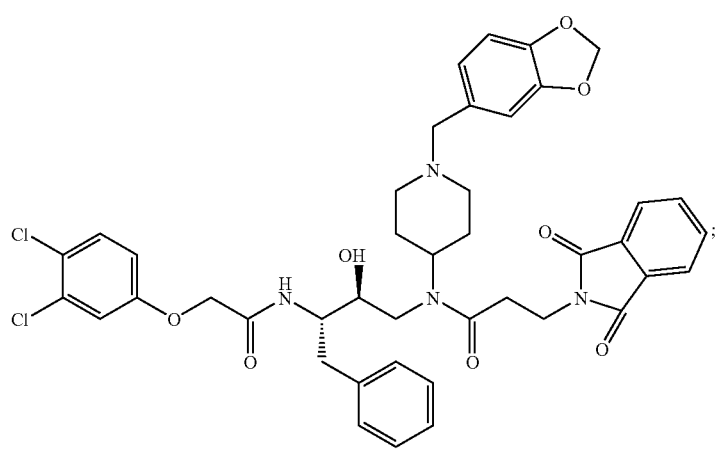
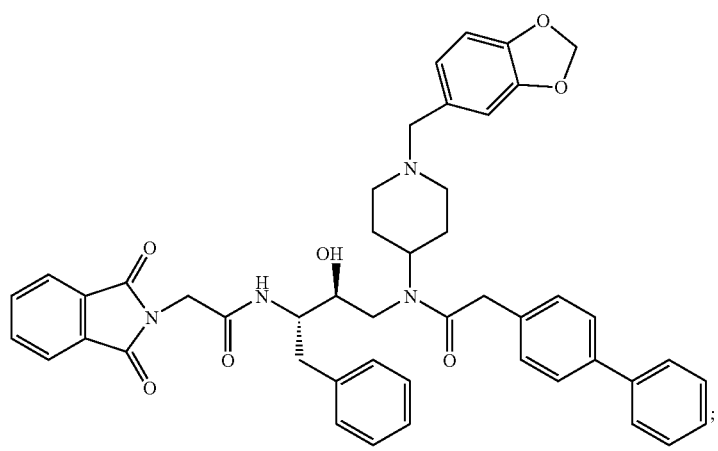

-continued
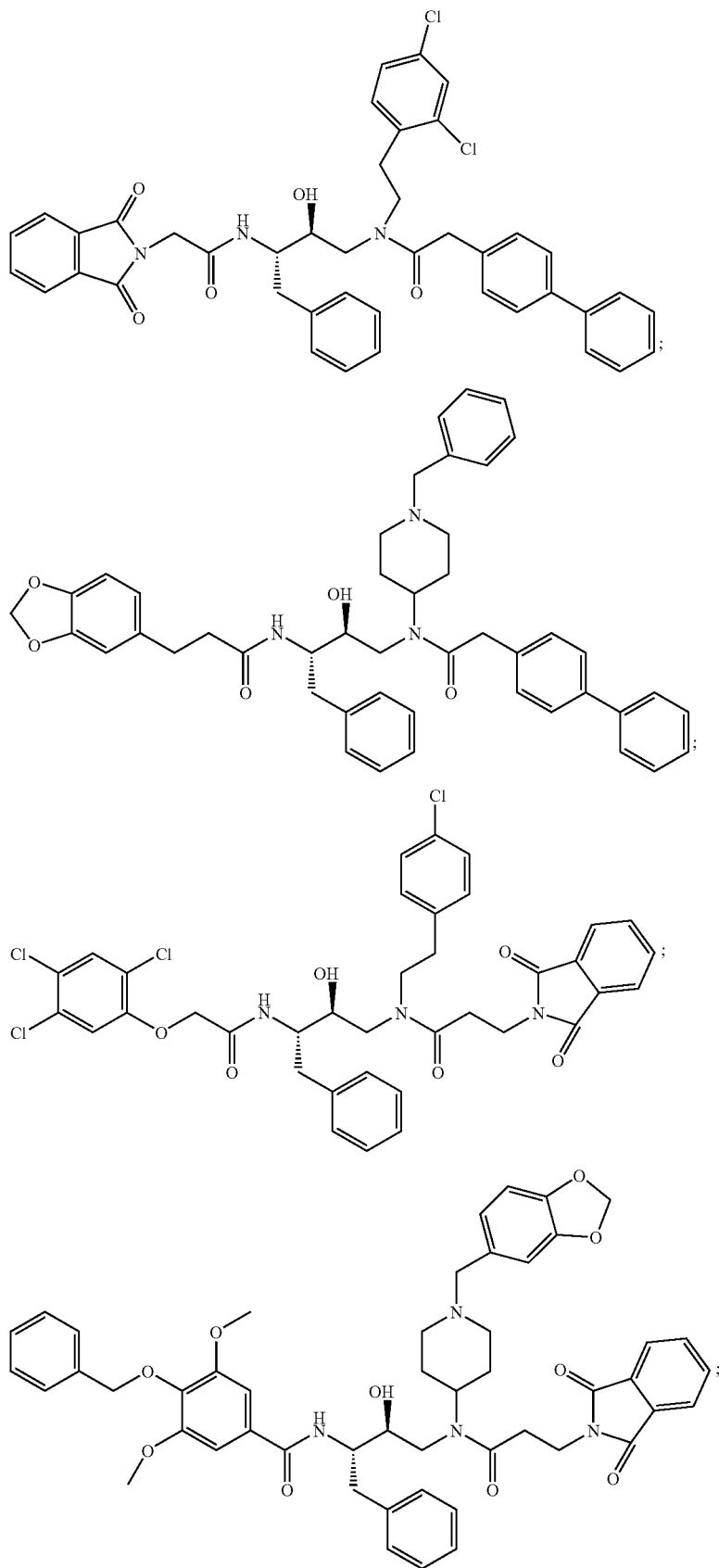

-continued
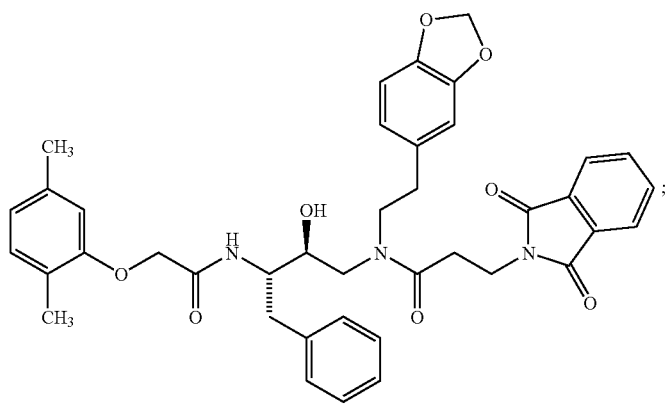
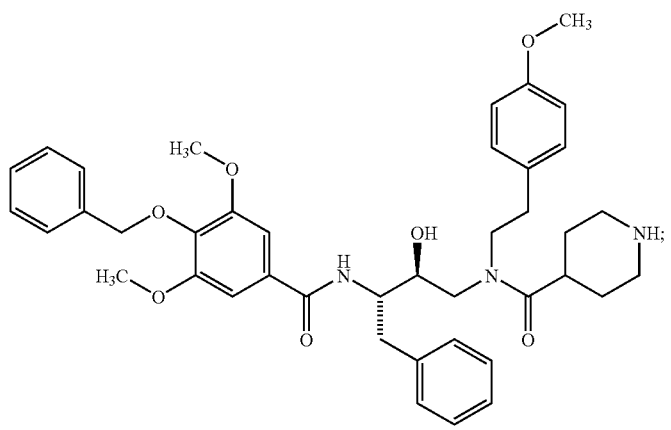
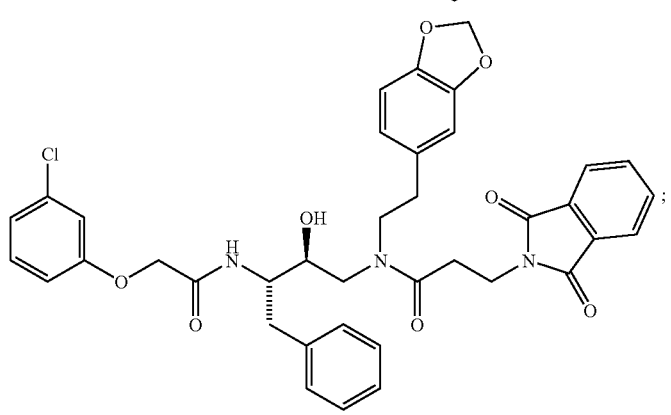
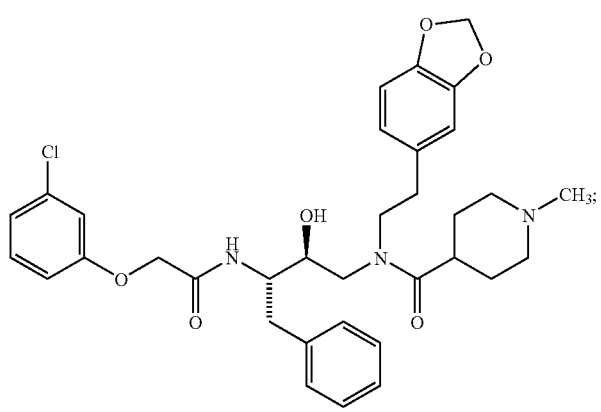

-continued
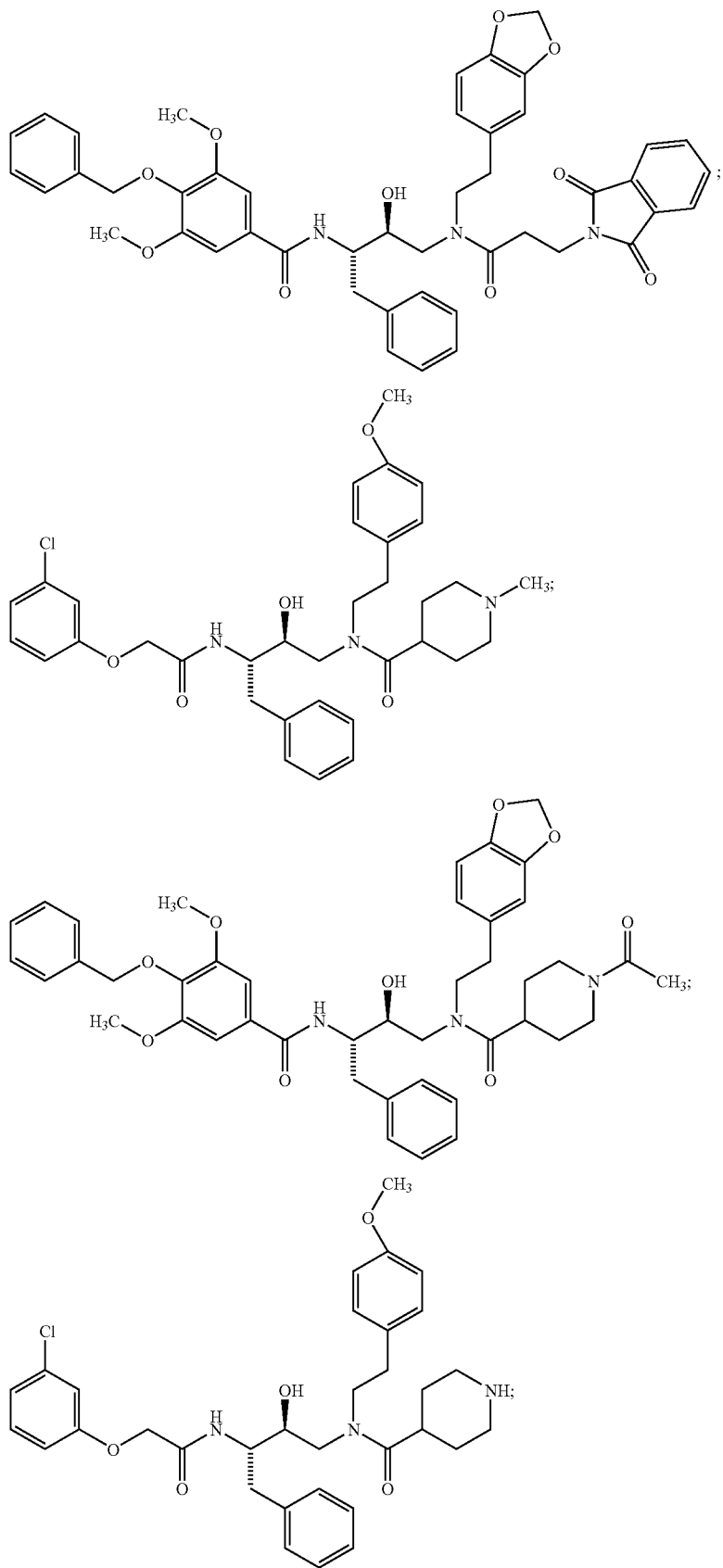

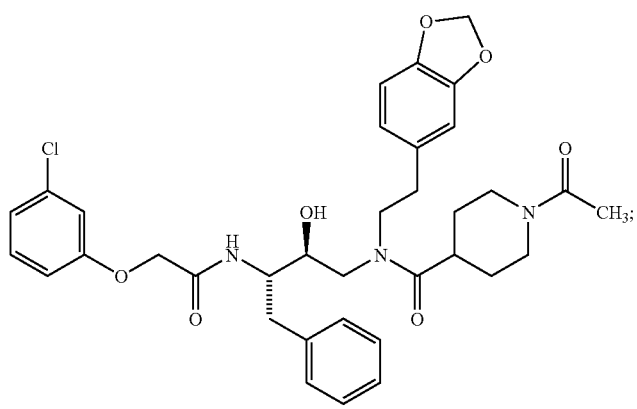
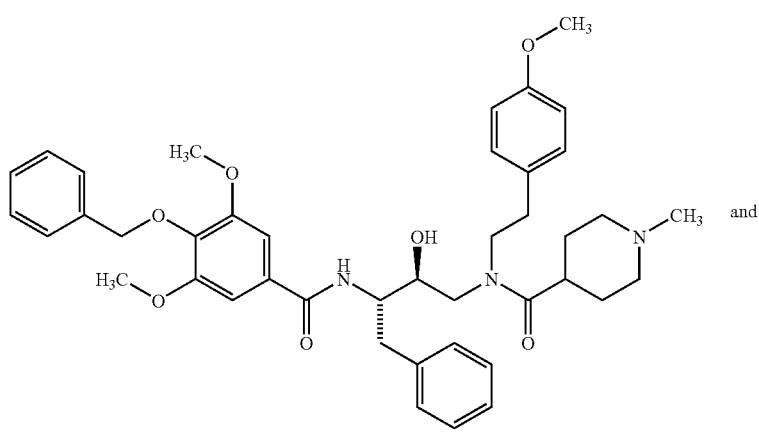
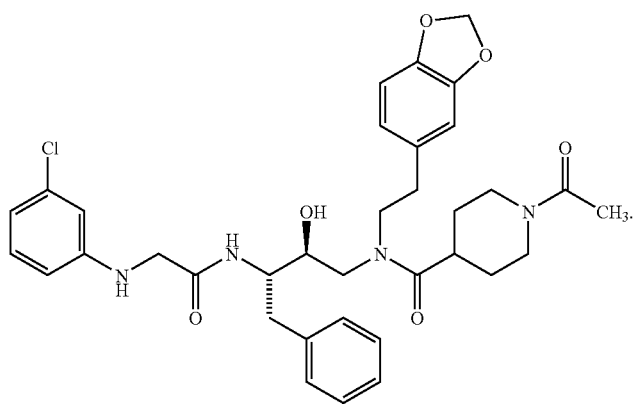

30. The method according to claim 19, wherein said aspartyl protease inhibitor is a member selected from the group consisting of:

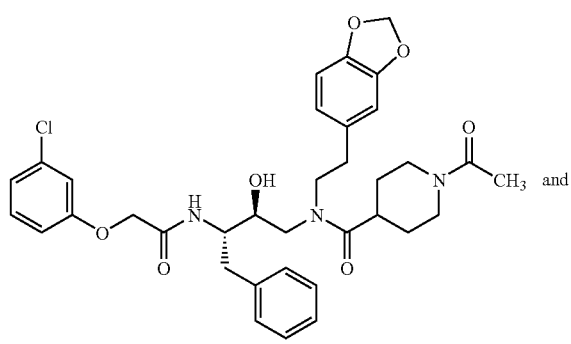

and

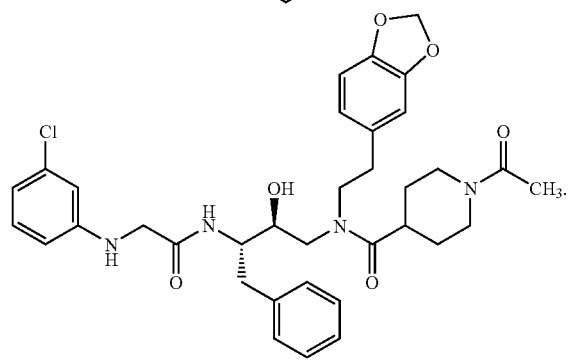

31. The method in accordance with claim 19, wherein said aspartyl protease inhibitor is a member selected from the group consisting of CEL5-A having the following structure:

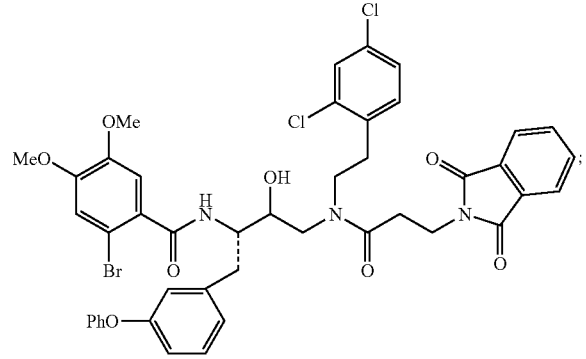

CEL5G having the following structure:

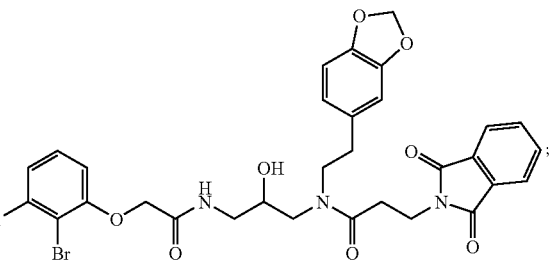

and

EA 1 having the following structure:

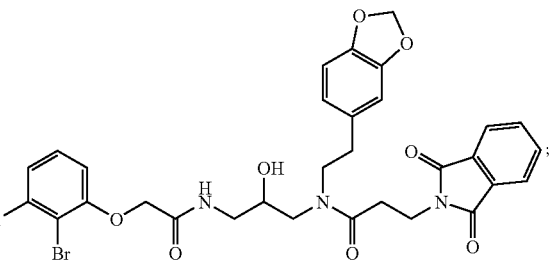

32. The method in accordance with claim 19, wherein said composition is a body fluid.

33. The method in accordance with claim 32, wherein said body fluid is cerebral spinal fluid.

34. The method in accordance with claim 19, whereby formation of τ-fragments is decreased compared to the amount formed in the absence of said aspartyl protease inhibitor.

35. The method in accordance with claim 19, wherein the modulation is effected by modulating the activity of cathepsin D.

* * * * *